United States Patent
Panduwawala et al.

(10) Patent No.: US 11,413,272 B2
(45) Date of Patent: Aug. 16, 2022

(54) INHIBITORS OF METALLO-BETA-LACTAMASES

(71) Applicant: Oxford University Innovation Limited, Oxford (GB)

(72) Inventors: Tharindi Panduwawala, Oxford (GB); Peter Brandt, Oxford (GB); David Wang, Oxford (GB); Mounir Andaloussi, Oxford (GB); Jürgen Brem, Oxford (GB); Christopher J. Schofield, Oxford (GB)

(73) Assignee: OXFORD UNIVERSITY INNOVATION LIMITED

( * ) Notice: Subject to any disclaimer, the term of this patent is extended or adjusted under 35 U.S.C. 154(b) by 15 days.

(21) Appl. No.: 16/616,515

(22) PCT Filed: May 25, 2018

(86) PCT No.: PCT/GB2018/051445
§ 371 (c)(1),
(2) Date: Nov. 25, 2019

(87) PCT Pub. No.: WO2018/215799
PCT Pub. Date: Nov. 29, 2018

(65) Prior Publication Data
US 2021/0137884 A1    May 13, 2021

(30) Foreign Application Priority Data
May 26, 2017   (GB) ..................................... 1708457

(51) Int. Cl.
| | | |
|---|---|---|
| C07D 207/34 | (2006.01) |
| A61K 31/403 | (2006.01) |
| A61P 31/04 | (2006.01) |
| A61K 31/401 | (2006.01) |
| A61K 31/4025 | (2006.01) |
| A61K 31/407 | (2006.01) |
| A61K 31/4164 | (2006.01) |
| C07D 209/42 | (2006.01) |
| C07D 209/70 | (2006.01) |
| C07D 233/90 | (2006.01) |
| C07D 405/04 | (2006.01) |

(52) U.S. Cl.
CPC .......... *A61K 31/403* (2013.01); *A61K 31/401* (2013.01); *A61K 31/407* (2013.01); *A61K 31/4025* (2013.01); *A61K 31/4164* (2013.01); *A61P 31/04* (2018.01); *C07D 207/34* (2013.01); *C07D 209/42* (2013.01); *C07D 209/70* (2013.01); *C07D 233/90* (2013.01); *C07D 405/04* (2013.01)

(58) Field of Classification Search
CPC .................................................... C07D 207/34
See application file for complete search history.

(56) References Cited

U.S. PATENT DOCUMENTS 3,467,755 A    9/1969   Schoen et al.

FOREIGN PATENT DOCUMENTS

| CA | 795352 A | 9/1968 |
| EP | 0 761 658 A1 | 12/1997 |
| EP | 2 305 643 A1 | 4/2011 |
| EP | 2 460 794 A1 | 6/2012 |
| JP | 43-19948 B2 | 8/2009 |
| WO | 2008/089453 A2 | 7/2008 |
| WO | 2011/013752 A1 | 2/2011 |
| WO | 2014/019908 A2 | 2/2014 |
| WO | WO-2014195705 A1 * | 12/2014 ........... C07D 401/12 |
| WO | 2017/093727 A1 | 6/2017 |

OTHER PUBLICATIONS

Khalaf, et al. Document No. 166:395364, retrieved from STN; Sep. 6, 2011.*
Dudfield, et al. Document No. 162:399868, retrieved from STN; Mar. 5, 2015.*
Andreotti, et al. Document No. 137:63420, retrieved from STN; Jun. 27, 2002.*
Gilbert, et al. Document No. 158:474777, retrieved from STN; Mar. 21, 2013.*
Zemribo, et al. Document No. 158:104980 retrieved from STN; Dec. 20, 2012.*
Sinha, et al. Document No. 157:410100 retrieved from STN; Aug. 30, 2012.*
Li, et al. Document No. 153:287035 retrieved from STN; Aug. 12, 2010.*
Jones, et al. Document No. 151:101172, retrieved from STN; Jun. 25, 2009.*
Sun, et al. Document No. 145:188738, retrieved from STN; Aug. 3, 2006.*
Heerding, et al. Document No. 142:219283, retrieved from STN; Feb. 10, 2005.*
International Search Report & Written Opinion for WO2018/215799 (PCT/GB2018/051445), dated Jul. 18, 2018, pp. 1-18.
(Continued)

*Primary Examiner* — Shawquia Jackson
(74) *Attorney, Agent, or Firm* — Thomas|Horstemeyer, LLP

(57) ABSTRACT

The present invention relates to compounds of Formula (I) that function as inhibitors of bacterial metallo-beta-lactamases. The present invention also relates to processes for the preparation of these compounds, to pharmaceutical compositions comprising them, and to their use in the treatment of a bacterial infection. (Formula (I))

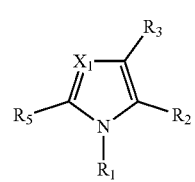

20 Claims, No Drawings

(56) References Cited

OTHER PUBLICATIONS

UK Search Report for GB1708457.5, dated Feb. 28, 2018, pp. 1-6.
International Preliminary Report on Patentability for WO2018/215799 (PCT/GB2018/051445), dated Nov. 26, 2019, pp. 1-10.
Aurora Screening Library, publication date Mar. 27, 2017, CAS Registry No. 2059507-47-8.
Tetrahedron, vol. 56, No. 43, 2000, pp. 8545-8553, Fejes et al. "A new synthesis of 3,5-diarylpyrrole-2-carboxylic acids and esters".
Journal of Materials and Environmental Science, vol. 1, No. 1, 2010, pp. 44-51, Idrissi Taghki et al. "Experimental and theoretical study of the immunoreactivity of 2-methoxy-carbonylpyrrole and derivatives on the lymphocyte T human".
Indian Journal of Chemistry, Section B: Organic Chemistry including Medicinal Chemistry, vol. 27B, No. 12, 1988, pp. 1113-1123, Nagarajan et al. "Synthesis and oral hypoglycemic properties of 4-oxo-4,5,6,7-tetrahydroindole-3—acetic acids".
Journal of Medicinal Chemistry, vol. 56, 2013, pp. 1894-1907, Katane et al. "Identification of novel D-amino acid oxidase inhibitors by in silico screening and their functional characterization in vitro".
Journal of Organic Chemistry, vol. 52, No. 24, 1987, pp. 5395-5400, Gelas-Mialhe et al. "photochemical heterocyclization of functionalized dienamines".
Journal of the Chemical Society, Transactions, vol. 121, 1922, pp. 947-958, Balaban et al. "Bromo derivatives of glyoxaline".
Journal of Medicinal Chemistry, vol. 29, No. 6, 1986, pp. 1065-1080, Baldwin et al. "β1-selective adrenoceptor antagonists: examples of the 2-[4-[3-(substituted amino)-2-hydroxypropoxy]phenyl]imidazole class. II".
Synthetic Communications, vol. 17, No. 12, 1987, pp. 1409-1412, Leone-Bay et al. "An efficient method for the preparation of 4(5)-cyanoimidazoles".
Verniest G et al., "Synthesis of 2-aryl-4-chloropyrroles via ring expansion of 2-aryl-1-chlorocyclopropanecarbaldehydes", Mar. 14, 2005 (Mar. 14, 2005), Tetrahedron, vol. 61, No. 11, p. 2879-2887.
Alfred Treibs et al., "Über einige Pyrrolderivate mit angegliedertem isocyclischem Ring. Bz-Tetrahydrindole und Cyclopentenopyrrole", Justus Liebigs Annalen Der Chemie, vol. 517, No. 1, Jan. 1, 1935 (Jan. 1, 1935), p. 152-169.
Damien Clarisse et al., "Hexafluoroisopropanol: a powerful solvent for the hydrogenation of indole derivatives. Selective access to tetrahydroindoles or cis-fused octahydroindoles", Organic & Biomolecular Chemistry, vol. 10, No. 32, Jan. 1, 2012 (Jan. 1, 2012), p. 6587.
Database Chemical Abstracts, Nagarajan et al., "Synthesis and oral hypoglycemic properties of 4-oxo-4,5,6,7-tetrahydroindole-3-acetic acids", XP002213029, retrieved from Chemical Database accession No. 57475y compound II.
L. N. Sobenina et al., "Synthesis of Pyrrole-2-Carboxylic Acids and Their N.Vinyl Derivatives", Chemistry of Heterocyclic Compounds, vol. 26, No. 5, May 1, 1990 (May 1, 1990), pp. 516-520.
Toney J H et al., "Structure-activity relationships of biphenyl tetrazoles as metallo-β-lactamase inhibitors", Bioorganic & Medicinal Chemistry Let, Pergamon, Amsterdam, NL, vol. 9, No. 18, Sep. 20, 1999 (Sep. 20, 1999), pp. 2741-2746.
Mosaad S Mohamed et al., "Synthesis and kinetic testing of new inhibitors for a metallo-β-lactamase from klebsiella pneumonia and pseudomonas aeruginosa", Oct. 13, 2011 (Oct. 13, 2011), vol. 46, No. 12, p. 6075-6082.

* cited by examiner

INHIBITORS OF METALLO-BETA-LACTAMASES

CROSS-REFERENCE TO RELATED APPLICATIONS

This application is the National Stage of International Application No. PCT/GB2018/051445, filed May 25, 2018, which claims the priority to GB 1708457.5, filed May 26, 2017, which are entirely incorporated herein by reference.

INTRODUCTION

The present invention relates to compounds that function as inhibitors of metallo-beta-lactamases. The present invention also relates to processes for the preparation of these compounds, to pharmaceutical compositions comprising them, and to their use in the treatment of bacterial infections.

BACKGROUND OF THE INVENTION

Infections caused by pathogenic bacteria are common worldwide, and thus antibacterial medicines to treat such infections are highly sought. Currently, β-lactam antibacterials (BLAs) are amongst the most widely used antibacterial treatments. However, the efficacy of BLAs is increasingly threatened by bacterial resistance, most importantly by the widespread dissemination of β-lactamases, which catalyse the hydrolysis and inactivation of BLA.[2]

In combination with a suitable penicillin, Class A β-lactamase inhibitors (BLIs) have been components of highly successful medicines (e.g. as in Augmentin). However, the zinc ion dependent Class B metallo-β-lactamases (MBLs, or carbapenemases), are structurally and mechanistically distinct from Class A, C and D serine β-lactamases (SBLs).[3] There is therefore a need for effective inhibitors of MBLs.

MBLs are particularly concerning because they hydrolyse most known BLAs, including the so called 'last resort' BLAs, such as some carbapenems, and confer resistance to BLAs in many pathogens. No clinically useful MBL inhibitors (MBLIs) are presently available.[4]

Though the problem of BLA resistance is most pronounced in developing countries, the number of cases of antimicrobial resistance (AMR) including Carbapenem-resistant Enterobacteriaceae (CRE) is substantially increasing worldwide.[5] It is notable that the estimates in these reports may under-represent the actual problem of BLA resistance, due to a lack of broad surveillance programs in some countries (many countries have not allocated, or do not have the resources for surveillance programs). A recent report shows NDM-1 is the most relevant MBL in the United Kingdom.[6] Similar reports are also appearing worldwide.

Thus, there remains a need for new treatments to combat MBL mediated antibacterial resistance.

The present invention was devised with the foregoing in mind.

SUMMARY OF THE INVENTION

In one aspect, the present invention provides a compound as defined herein, or a pharmaceutically acceptable salt or solvate thereof.

In another aspect, the present invention provides a compound as defined herein, or a pharmaceutically acceptable salt or solvate thereof, for use in the treatment of a bacterial infection.

In another aspect, the present invention provides a compound as defined herein, or a pharmaceutically acceptable salt or solvate thereof, in combination with a suitable antibacterial agent, for use in the treatment of a bacterial infection.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in the treatment of bacterial infections.

In another aspect, the present invention provides a compound as defined herein, or a pharmaceutically acceptable salt or solvate thereof, or a pharmaceutical composition as defined herein, for use in the production of a metallo-beta-lactamase inhibitory effect.

In another aspect, the present invention provides a method of inhibiting a bacterial metallo-beta-lactamase in vitro or in vivo, said method comprising contacting a cell with an effective amount of a compound as defined herein, or a pharmaceutically acceptable salt or solvate thereof.

In another aspect, the present invention provides a method of treating a bacterial infection in a patient or animal in need of such treatment, said method comprising administering to said patient a therapeutically effective amount of a compound as defined herein, or a pharmaceutically acceptable salt or solvate thereof, or a pharmaceutical composition as defined herein, in combination with a suitable antibacterial agent.

In another aspect, the present invention provides the use of a compound, as defined herein, in combination with a suitable antibacterial agent, for the treatment of a bacterial infection.

In another aspect, the present invention provides the use of a compound, as defined herein, for the inhibition of a metallo-beta-lactamase.

In another aspect, there is provided a kit of parts comprising the following components:
  a compound of Formula I, as defined herein, or a pharmaceutically-acceptable salt thereof, in association with a pharmaceutically acceptable adjuvant, diluent or carrier; and
  a β-lactam antibiotic, or a pharmaceutically-acceptable salt thereof, in association with a pharmaceutically acceptable adjuvant, diluent or carrier,
wherein the components are provided in a form which is suitable for sequential, separate and/or simultaneous administration.

The kit of parts is for the treatment of bacterial infections.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups and analogues thereof. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo [2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo ($=$O) or thioxo ($=$S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, $4^{th}$ Edition, Wiley Interscience, pages 131-133, 1992. Examples of bridged heterocyclyl ring systems include, aza-bicyclo [2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members.

The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

COMPOUNDS OF THE INVENTION

In one aspect, the present invention relates to a compound of Formula I, or a pharmaceutically acceptable salt or solvate thereof, as shown below:

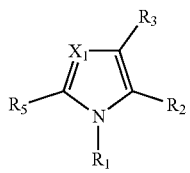

Formula I wherein
R₁ is selected from hydrogen, (1-4C)alkyl or aryl, wherein each (1-4C)alkyl or aryl is optionally substituted by one or more substituent groups selected from oxo, halo, cyano, nitro, hydroxy, carboxy, $NR^{1A}R^{1B}$ or (1-4C)alkoxy, and wherein $R^{1A}$ and $R^{1B}$ are each independently selected from hydrogen or (1-2C)alkyl;

R₂ is selected from:
(i) —C(O)OH;
(ii) —C(O)OR$_{2A}$, wherein R$_{2A}$ is selected from (1-6C)alkyl, (3-8O)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
(iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
(iv) —C(O)NR$_{2D}$NR$_{2B}$R$_{2E}$; wherein R$_{2D}$ is selected from hydrogen or (1-6C)alkyl and R$_{2B}$ and R$_{2C}$ are as defined above;
(v) tetrazolyl;
(vi) triazolyl;
(vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
(viii) trifluoromethylketone; or
(ix) cyano;
(x) —[C(O)]$_v$S(NR$_{2X}$)(O)NR$_{2B}$R$_{2C}$ (where v is 0 or 1), wherein R$_{2X}$ is selected from hydrogen, (1-6C)alkyl, C(O)R$_X$, C(O)OR$_X$, aryl, aryl-(1-2C)alkyl, heteroaryl, heteroaryl-(1-2C)alkyl, heterocyclyl or heterocyclyl-(1-2C)alkyl, wherein R$_X$ is selected from (1-6C)alkyl, aryl or heteroaryl, each of which is optionally substituted with one or more R$_A$, and wherein R$_{2B}$ and R$_{2C}$ are as defined above;
(xi) —[C(O)]$_w$N(R$_{2B}$)S(NR$_{2X}$)(O)R$_X$ (where w is 0 or 1), wherein R$_{2B}$, R$_{2X}$ and R$_X$ are each as defined above; or
(xii) —S(O)$_y$NR$_{2B}$R$_{2C}$ (wherein y is 1 or 2), and wherein R$_{2B}$ and R$_{2C}$ are as defined above,
and wherein $R^A$ is selected from oxo, halo, cyano, nitro or a group of the formula:

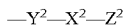—Y²—X²—Z² wherein
Y² is absent or a linker group of the formula —[CR$^{A1}$R$^{A2}$]$_m$— in which m is an integer selected from 1, 2, 3 or 4, and R$^{A1}$ and R$^{A2}$ are each independently selected from hydrogen or (1-2C)alkyl;
X² is absent or —O—, —C(O)—, —C(O)O—, —OC(O)—, —CH(OR$^{A3}$)—, —N(R$^{A3}$)—, —N(R$^{A3}$)—C(O)—, —N(R$^{A3}$)—(O)O—, —C(O)—N(R$^{A3}$)—, —N(R$^{A3}$)C(O)N(R$^{A3}$)—, —S—, —SO—, —SO$_2$—, —S(O)$_2$N(R$^{A3}$)—, or —N(R$^{A3}$)SO$_2$— wherein R$^{A3}$ is selected from hydrogen or methyl; and
Z² is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z² is optionally further substituted by one or more substituent groups independently selected from oxo, halo, cyano, nitro, hydroxy, carboxy, NR$^{A4}$R$^{A5}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{A4}$R$^{A5}$, NR$^{A4}$C(O)R$^{A5}$, NR$^{A4}$S(O)$_2$R$^{A5}$ and S(O)$_2$NR$^{A4}$R$^{A5}$; wherein R$^{A4}$ and R$^{A5}$ are each independently selected from hydrogen, (1-4C)alkyl or (3-6C)cycloalkyl or (3-6C)cycloalkyl(1-2C)alkyl; or R$^{A4}$ and R$^{A5}$ can be linked such that, together with the nitrogen atom to which they are attached, they form a 4-6 membered heterocyclic ring;
and wherein any alkyl, aryl, heterocyclyl or heteroaryl group present in a substituent group on Z² is optionally further substituted by halo, cyano, nitro, hydroxy, caboxy, NR$^{A6}$R$^{A7}$, (1-2)alkoxy, or (1-2C)alkyl; wherein R$^{A6}$ and R$^{A7}$ are selected from hydrogen or (1-2C)alkyl;
R₃ is selected from hydrogen, halo, cyano, hydroxy, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;
R$^B$ is halo, cyano, nitro, hydroxy or a group:

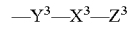—Y³—X³—Z³ wherein
Y³ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
X³ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z³ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z³ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-8O)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$ wherein R$^{B5}$ and R$^{B6}$ are each independently selected from hydrogen, (1-4C)alkyl or (3-6C)cycloalkyl or (3-6C)cycloalkyl(1-2C)alkyl; or R$^{B5}$ and R$^{B6}$ can be linked such that, together with the nitrogen atom to which they are attached, they form a 4-7 membered heterocyclic ring;

and wherein any alkyl, aryl, heterocyclyl or heteroaryl group present in a substituent group on $Z^3$ is optionally further substituted by halo, cyano, nitro, hydroxy, caboxy, $NR^{B7}R^{B8}$, (1-2C)alkoxy, or (1-2C)alkyl; wherein $R^{B7}$ and $R^{B8}$ are selected from hydrogen or (1-2)alkyl;

or $R^{B3}$ and $Z^3$ can be linked such that, together with the nitrogen atom to which they are attached, they form a 4-7 membered heterocyclic ring, which is optionally substituted by oxo, halo, cyano, nitro, hydroxy, carboxy, $NR^{B5}R^{B6}$ (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, $C(O)NR^{B5}R^{B6}$, $NR^{B5}C(O)R^{B6}$, $NR^{B5}S(O)_2R^{B6}$ and $S(O)_2NR^{B5}R^{B6}$;

$X_1$ is selected from N or C—$R_4$;

$R_4$ is selected from halo, cyano, nitro, hydroxy or a group

—$Y^4$—$X^4$—$Z^4$ wherein:
$Y^4$ is absent or a linker group of the formula —$[CR^{4A}R^{4B}]_q$— in which q is an integer selected from 1 or 2 and $R^{4A}$ and $R^{4B}$ are each independently selected from hydrogen or methyl;

$X^4$ is absent or —O—, —C(O)—, —C(O)O—, —OC(O)—, —CH(OR^{4C})—, —N(R^{4C})—, —N(R^{4D})—C(O)—, —N(R^{4D})—C(O)O—, —C(O)—N(R^{4C})—, —S—, —SO—, —SO_2—, —S(O)_2N(R^{4C})—, or —N(R^{4D})SO_2— wherein $R^{4C}$ and $R^{4D}$ are each independently selected from hydrogen or (1-4C)alkyl; and $Z^4$ is hydrogen or (1-4C)alkyl which is optionally further substituted by one or more substituent groups independently selected from oxo, halo, cyano, nitro, hydroxy, carboxy, $NR^{4E}R^{4F}$ or (1-2)alkoxy; wherein $R^{4E}$ and $R^{4F}$ are each independently selected from hydrogen or (1-2C)alkyl;

$R_5$ is selected from hydrogen, halo, cyano, nitro, hydroxy or a group

—$Y^5$—$X^5$-$Q^5$-$Z^5$ wherein
$Y^5$ is absent or a linker group of the formula —$[CR^{5A}R^{5B}]_p$— in which p is an integer selected from 1 or 2, and $R^{5A}$ and $R^{5B}$ are each independently selected from hydrogen or (1-2C)alkyl;

$X^5$ is absent or —O—, —C(O)—, —C(O)O—, —OC(O)—, —CH(OR^{5C})—, —N(R^{5C})—, —N(R^{5D})—C(O)—, —N(R^{5D})—C(O)O—, —C(O)—N(R^{5C})—, —N(R^{5D})C(O)N(R^{5C})—, —S—, —SO—, —SO_2—, —S(O)_2N(R^{5C})—, or —N(R^{5D})SO_2— wherein $R^{5C}$ and $R^{5D}$ are each independently selected from hydrogen or (1-6C)alkyl;

$Q^5$ is absent or a (1-4C)alkylene optionally interrupted by one or more O or S atoms; and $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^5$ is optionally further substituted by one or more substituent groups independently selected from oxo, halo, cyano, nitro, hydroxy, carboxy, $NR^{5E}R^{5F}$, (1-40)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]_3, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; wherein $R^{5E}$ and $R^{5F}$ are each independently selected from hydrogen, (1-4C)alkyl, (1-4C)haloalkyl, (3-6C)cycloalkyl or (3-6C)cycloalkyl(1-2C)alkyl; or $R^{5E}$ and $R^{5F}$ can be linked such that, together with the nitrogen atom to which they are attached, they form a 4-7 membered heterocyclic ring;

and wherein any alkyl, aryl, heterocyclyl or heteroaryl group present in a substituent group on $Z^5$ is optionally further substituted by one or more substituent groups selected from halo, (1-2C)haloalkyl, cyano, nitro, hydroxy, carboxy, $NR^{5G}R^{5H}$, (1-2)alkoxy, or (1-2C)alkyl; wherein $R^{5G}$ and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$, (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; or $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl, (1-4C)haloalkyl, (3-6C)cycloalkyl or (3-6C)cycloalkyl(1-2C)alkyl; or $R^{5I}$ and $R^{5J}$ can be linked such that, together with the nitrogen atom to which they are attached, they form a 4-7 membered heterocyclic ring.

In an embodiment of the present invention, there is provided a compound of Formula I, or a pharmaceutically acceptable salt or solvate thereof, as shown below:

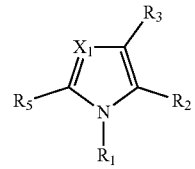

Formula I wherein
$R_1$ is selected from hydrogen, (1-4C)alkyl or aryl, wherein each (1-4C)alkyl or aryl is optionally substituted by one or more substituent groups selected from oxo, halo, cyano, nitro, hydroxy, carboxy, $NR^{1A}R^{1B}$ or (1-4C)alkoxy, and wherein $R^{1A}$ and $R^{1B}$ are each independently selected from hydrogen or (1-2C)alkyl;

$R_2$ is selected from:
(i) —C(O)OH;
(ii) —C(O)OR$_{2A}$, wherein R$_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^A$;
(iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^A$;
(iv) —C(O)NR$_{2D}$NR$_{2B}$R$_{2E}$; wherein R$_{2D}$ is selected from hydrogen or (1-6C)alkyl and R$_{2B}$ and R$_{2C}$ are as defined above;
(v) tetrazolyl;
(vi) triazolyl;
(vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
(viii) trifluoromethylketone; or
(ix) cyano;
(x) —[C(O)]$_v$S(NR$_{2X}$)(O)NR$_{2B}$R$_{2C}$ (where v is 0 or 1), wherein R$_{2X}$ is selected from hydrogen, (1-6C)alkyl, C(O)R$_X$, C(O)OR$_X$, aryl, aryl-(1-2C)alkyl, heteroaryl, heteroaryl-(1-2C)alkyl, heterocyclyl or heterocyclyl-(1-2C)alkyl, wherein R$_X$ is selected from (1-6C)alkyl, aryl or heteroaryl, each of which is optionally substituted with one or more R$_A$, and wherein R$_{2B}$ and R$_{2C}$ are as defined above;
(xi) —[C(O)]$_w$N(R$_{2B}$)S(NR$_{2X}$)(O)R$^X$ (where w is 0 or 1), wherein R$_{2B}$, R$_{2X}$ and R$_X$ are each as defined above; or
(xii) —S(O)$_y$NR$_{2B}$R$_{2C}$ (wherein y is 1 or 2), and wherein R$_{2B}$ and R$_{2C}$ are as defined above,
and wherein R$^A$ is selected from oxo, halo, cyano, nitro or a group of the formula:

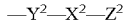

wherein
Y$^2$ is absent or a linker group of the formula —[CR$^{A1}$R$^{A2}$]$_m$— in which m is an integer selected from 1, 2, 3 or 4, and R$^{A1}$ and R$^{A2}$ are each independently selected from hydrogen or (1-2C)alkyl;
X$^2$ is absent or —O—, —C(O)—, —C(O)O—, —OC(O)—, —CH(OR$^{A3}$)—, —N(R$^{A3}$)—, —N(R$^{A3}$)—C(O)—, —N(R$^{A3}$)—C(O)O—, —C(O)—N(R$^{A3}$)—, —N(R$^{A3}$)C(O)N(R$^{A3}$)—, —S—, —SO—, —SO$_2$—, —S(O)$_2$N(R$^{A3}$)—, or —N(R$^{A3}$)SO$_2$— wherein R$^{A3}$ is selected from hydrogen or methyl; and
Z$^2$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^2$ is optionally further substituted by one or more substituent groups independently selected from oxo, halo, cyano, nitro, hydroxy, carboxy, NR$^{A4}$R$^{A5}$, (1-40)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{A4}$R$^{A5}$, NR$^{A4}$C(O)R$^{A5}$, NR$^{A4}$S(O)$_2$R$^{A5}$ and S(O)$_2$NR$^{A4}$R$^{A5}$; wherein R$^{A4}$ and R$^{A5}$ are each independently selected from hydrogen, (1-4C)alkyl or (3-6C)cycloalkyl or (3-6C)cycloalkyl(1-2C)alkyl; or R$^{A4}$ and R$^{A5}$ can be linked such that, together with the nitrogen atom to which they are attached, they form a 4-6 membered heterocyclic ring;
and wherein any alkyl, aryl, heterocyclyl or heteroaryl group present in a substituent group on Z$^2$ is optionally further substituted by halo, cyano, nitro, hydroxy, caboxy, NR$^{A6}$R$^{A7}$, (1-2C)alkoxy, or (1-2C)alkyl; wherein R$^{A6}$ and R$^{A7}$ are selected from hydrogen or (1-2C)alkyl;
$R_3$ is selected from hydrogen, halo, cyano, hydroxy, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;
R$^B$ is halo, cyano, nitro, hydroxy or a group:

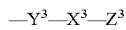

wherein
Y$^3$ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^3$ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-80)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$; wherein R$^{B5}$ and R$^{B6}$ are each independently selected from hydrogen, (1-4C)alkyl or (3-6C)cycloalkyl or (3-6C)cycloalkyl(1-2C)alkyl; or R$^{B5}$ and R$^{B6}$ can be linked such that, together with the nitrogen atom to which they are attached, they form a 4-7 membered heterocyclic ring;
and wherein any alkyl, aryl, heterocyclyl or heteroaryl group present in a substituent group on Z$^3$ is optionally further substituted by halo, cyano, nitro, hydroxy, caboxy, NR$^{B7}$R$^{B8}$, (1-20)alkoxy, or (1-20)alkyl; wherein R$^{B7}$ and R$^{B8}$ are selected from hydrogen or (1-20)alkyl;
or R$^{B3}$ and Z$^3$ can be linked such that, together with the nitrogen atom to which they are attached, they form a 4-7 membered heterocyclic ring, which is optionally substituted by oxo, halo, cyano, nitro, hydroxy, carboxy, NR$^{B5}$R$^{B6}$ (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$;

$X_1$ is selected from N or C—$R_4$;
$R_4$ is selected from halo, cyano, nitro, hydroxy or a group $$-Y^4-X^4-Z^4$$

wherein:
  $Y^4$ is absent or a linker group of the formula —[$CR^{4A}R^{4B}$]$_q$— in which q is an integer selected from 1 or 2 and $R^{4A}$ and $R^{4B}$ are each independently selected from hydrogen or methyl;
  $X^4$ is absent or —O—, —C(O)—, —C(O)O—, —OC(O)—, —CH($OR^{4C}$)—, —N($R^{4C}$)—, —N($R^{4D}$)—C(O)—, —N($R^{4D}$)—C(O)O—, —C(O)—N($R^{4C}$)—, —S—, —SO—, —$SO_2$—, —S(O)$_2$N($R^{4C}$)—, or —N($R^{4D}$)$SO_2$— wherein $R^{4C}$ and $R^{4D}$ are each independently selected from hydrogen or (1-4C)alkyl; and
  $Z^4$ is hydrogen or (1-4C)alkyl which is optionally further substituted by one or more substituent groups independently selected from oxo, halo, cyano, nitro, hydroxy, carboxy, $NR^{4E}R^{4F}$ or (1-2C)alkoxy; wherein $R^{4E}$ and $R^{4F}$ are each independently selected from hydrogen or (1-2C)alkyl;
$R_5$ is selected from hydrogen, halo, cyano, nitro, hydroxy or a group $$-Y^5-X^5-Z^5$$

wherein
  $Y^5$ is absent or a linker group of the formula —[$CR^{5A}R^{5B}$]$_p$— in which p is an integer selected from 1 or 2, and $R^{5A}$ and $R^{5B}$ are each independently selected from hydrogen or (1-2C)alkyl;
  $X^5$ is absent or —O—, —C(O)—, —C(O)O—, —OC(O)—, —CH($OR^{5C}$)—, —N($R^{5C}$)—, —N($R^{5D}$)—C(O)—, —N($R^{5D}$)—C(O)O—, —C(O)—N($R^{5C}$)—, —N($R^{5D}$)C(O)N($R^{5C}$)—, —S—, —SO—, —$SO_2$—, —S(O)$_2$N($R^{5C}$)—, or —N($R^{5D}$)$SO_2$— wherein $R^{5C}$ and $R^{5D}$ are each independently selected from hydrogen or (1-6C)alkyl; and
  $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
    and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, C(O)$R^{5E}$, C(O)O$R^{5E}$, OC(O)$R^{5E}$, C(O)N$R^{5E}R^{5F}$, $NR^{5E}$C(O)$R^{5F}$, $NR^{5E}$S(O)$_2R^{5F}$ and S(O)$_2$N$R^{5E}R^{5F}$; wherein $R^{5E}$ and $R^{5F}$ are each independently selected from hydrogen, (1-4C)alkyl, (1-4C)haloalkyl, (3-6C)cycloalkyl or (3-6C)cycloalkyl(1-2C)alkyl; or $R^{5E}$ and $R^{5F}$ can be linked such that, together with the nitrogen atom to which they are attached, they form a 4-7 membered heterocyclic ring;
    and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-2)alkoxy, or (1-2C)alkyl; wherein $R^{5G}$ and $R^{5H}$ are selected from hydrogen or (1-2C)alkyl;
  or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$ (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, C(O)$R^E$, C(O)O$R^E$, OC(O)$R^E$C(O)N$R^{5E}R^{5F}$, $NR^{5E}$C(O)RIF, $NR^{5E}$S(O)$_2R^{5F}$ and S(O)$_2$N$R^{5E}R^{5F}$; or
  $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, C(O)$R^{5J}$, C(O)O$R^{5J}$, OC(O)$R^{5J}$, C(O)N$R^{5I}R^{5J}$, $NR^{5I}$C(O)$R^{5J}$, $NR^{5I}$S(O)$_2R^{5J}$ and S(O)$_2$N$R^{5I}R^{5J}$, wherein $R^{5i}$ and $R^{5j}$ are each independently selected from hydrogen, (1-4C)alkyl, (1-4C)haloalkyl, (3-6C)cycloalkyl or (3-6C)cycloalkyl(1-2C)alkyl; or $R^{5'}$ and $R^5$ can be linked such that, together with the nitrogen atom to which they are attached, they form a 4-7 membered heterocyclic ring.

Particular compounds of the invention include, for example, compounds of the formula I, or pharmaceutically acceptable salts and/or solvates thereof, wherein, unless otherwise stated, each of $X_1$, $R_1$, $R_2$, $R_3$ and $R_5$ and any associated substituent groups has any of the meanings defined hereinbefore or in any of paragraphs (1) to (63) hereinafter:—

(1) $R_1$ is selected from hydrogen or (1-4C)alkyl, wherein each (1-4C)alkyl is optionally substituted by one or more substituent groups selected from oxo, halo, cyano, nitro, hydroxy, carboxy, $NR^{1A}R^{1B}$ or (1-4C)alkoxy, wherein $R^A$ and $R^B$ are each independently selected from hydrogen or (1-2C)alkyl;

(2) $R_1$ is selected from hydrogen or (1-4C)alkyl which is optionally substituted by one or more substituent groups selected from oxo, halo, cyano, carboxy, $NR^{1A}R^{1B}$ or (1-4C)alkoxy, wherein $R^{1A}$ and $R^{1B}$ are each independently selected from hydrogen or (1-2C)alkyl;

(3) $R_1$ is selected from hydrogen, (1-4C)alkyl or phenyl, wherein each (1-4C)alkyl or phenyl is optionally substituted by one or more substituent groups selected from oxo, halo, cyano, $NR^{1A}R^{1B}$ or (1-20)alkoxy, wherein $R^A$ and $R^B$ are each independently selected from hydrogen or methyl;

(4) $R_1$ is selected from hydrogen or (1-4C)alkyl which is optionally substituted by one or more substituent groups selected from oxo, halo, cyano, $NR^{1A}R^{1B}$ or (1-2C)alkoxy, wherein $R^A$ and $R^B$ are each independently selected from hydrogen or methyl;

(5) $R^1$ is selected from hydrogen, (1-4C)alkyl or phenyl, wherein each (1-4C)alkyl or phenyl is optionally substituted by one or more substituent groups selected from oxo, halo, or (1-2C)alkoxy;

(6) $R_1$ is selected from hydrogen or (1-4C)alkyl which is optionally substituted by one or more substituent groups selected from oxo, halo, or (1-2C)alkoxy;

(7) $R_1$ is selected from hydrogen or (1-4C)alkyl which is optionally substituted by one or more substituent groups selected from oxo, fluoro or chloro;

(8) $R_1$ is selected from hydrogen or (1-4C)alkyl which is optionally substituted by one or more fluoro groups;
(9) $R_1$ is selected from hydrogen or (1-2C)alkyl;
(10) $R_1$ is hydrogen;
(11) $R_2$ is selected from:
  (i) —C(O)OH;
  (ii) —C(O)O$R_{2A}$, wherein $R_{2A}$ is selected from (1-60)alkyl, (3-80)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
  (iii) —C(O)N$R_{2B}R_{2C}$; wherein $R_{2B}$ and $R_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
  (iv) —C(O)N$R_{2D}$N$R_{2B}R_{2C}$; wherein $R_{2D}$ is selected from hydrogen or (1-6C)alkyl and $R_{2B}$ and $R_{2C}$ are as defined above;
  (v) tetrazolyl;
  (vi) triazolyl;
  (vii) —B(O$R_{2F}$)(O$R_{2G}$), wherein $R_{2F}$ and $R_{2G}$ are each independently selected from hydrogen, (1-6C)alkyl or $R_{2F}$ and $R_{2G}$ are linked such that, together with the B and O atoms, they form a 5 or 6-membered heterocyclic ring, which is optionally substituted by (1-2C)alkyl;
  (viii) trifluoromethylketone; or
  (ix) cyano;
  (x) —[C(O)]$_v$S(N$R_{2X}$)(O)N$R_{2B}R_{2C}$ (where v is 0 or 1), wherein $R_{2X}$ is selected from hydrogen, (1-6C)alkyl, C(O)$R_X$, C(O)O$R_X$, aryl, aryl-(1-2C)alkyl, heteroaryl, heteroaryl-(1-2C)alkyl, heterocyclyl or heterocyclyl-(1-2C)alkyl, wherein $R_X$ is selected from (1-6C)alkyl, aryl or heteroaryl, each of which is optionally substituted with one or more $R_A$, and wherein $R_{2B}$ and $R_{2C}$ are as defined above
  (xi) —[C(O)]$_w$N($R_{2B}$)S(N$R_{2X}$)(O)$R_X$ (where w is 0 or 1), wherein $R_{2B}$, $R_{2X}$ and $R_X$ are each as defined above; or
  (xii) —S(O)$_y$N$R_{2B}R_{2C}$ (wherein y is 1 or 2), and wherein $R_{2B}$ and $R_{2C}$ are as defined above,
and wherein $R^A$ is selected from halo, cyano, nitro or a group of the formula:

—Y²—X²—Z² wherein
  Y² is absent or a linker group of the formula —[C$R^{41}R^{42}$]$_m$— in which m is an integer selected from 1 or 2, and $R^{41}$ and $R^{42}$ are each independently selected from hydrogen or (1-2C)alkyl;
  X² is absent or —O—, —C(O)—, —C(O)O—, —OC(O)—, —N($R^{43}$)—, —N($R^{43}$)—C(O)—, —N($R^{43}$)—C(O)O—, —C(O)—N($R^{43}$)—, —N($R^{43}$)C(O)N($R^{43}$), —SO₂—, —S(O)₂N($R^{43}$)—, or —N($R^{43}$)SO₂— wherein $R^{43}$ is selected from hydrogen or methyl; and
  Z² is hydrogen, (1-6C)alkyl, aryl, (3-6C)cycloalkyl, (3-6C)cycloalkenyl, heteroaryl or heterocyclyl;
  and wherein Z² is optionally further substituted by one or more substituent groups independently selected from oxo, halo, cyano, nitro, hydroxy, carboxy, N$R^{44}R^{45}$, (1-40)alkoxy, (1-4C)alkyl, (3-8C)cycloalkyl, (1-4C)alkanoyl, (1-4C)alkylsulphonyl, C(O)N$R^{44}R^{45}$, N$R^{44}$C(O)$R^{45}$, N$R^{44}$S(O)₂$R^{45}$ and S(O)₂N$R^{44}R^{45}$; wherein $R^{44}$ and $R^{45}$ are each independently selected from hydrogen, or (1-4C)alkyl; or $R^{44}$ and $R^{45}$ can be linked such that, together with the nitrogen atom to which they are attached, they form a 4-6 membered heterocyclic ring;
(12) $R_2$ is selected from:
  (i) —C(O)OH;
  (ii) —C(O)O$R_{2A}$, wherein $R_{2A}$ is selected from (1-6C)alkyl, (3-80)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
  (iii) —C(O)N$R_{2B}R_{2C}$; wherein $R_{2B}$ and $R_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;
  (iv) —C(O)N$R_{2D}$N$R_{2B}R_{2C}$; wherein $R_{2D}$ is selected from hydrogen or (1-6C)alkyl and $R_{2B}$ and $R_{2C}$ are as defined above;
  (v) tetrazolyl;
  (vi) triazolyl;
  (vii) —B(O$R_{2F}$)(O$R_{2G}$), wherein $R_{2F}$ and $R_{2G}$ are each independently selected from hydrogen, (1-6C)alkyl or $R_{2F}$ and $R_{2G}$ are linked such that, together with the B and O atoms, they form a 5 or 6-membered heterocyclic ring, which is optionally substituted by (1-2C)alkyl;
  (viii) trifluoromethylketone; or
  (ix) cyano;
  (x) —[C(O)]S(N$R_{2X}$)(O)N$R_{2B}R_{2C}$ (where v is 0 or 1), wherein $R_{2X}$ is selected from hydrogen or (1-6C)alkyl, and wherein $R_{2B}$ and $R_{2C}$ are as defined above.
  (xi) —[C(O)]$_w$N($R_{2B}$)S(N$R_{2X}$)(O)$R_X$ (where w is 0 or 1), wherein $R_{2B}$, $R_{2X}$ and $R_X$ are each as defined above; or
  (xii) —S(O)N$R_{2B}R_{2C}$, and wherein $R_{2B}$ and $R_{2C}$ are as defined above, and wherein $R^A$ is selected from halo, cyano, nitro or a group of the formula:

—X²—Z² wherein
  X² is absent or —C(O)—, —N($R^{43}$)—C(O)—, —C(O)—N($R^{43}$), —SO₂—, wherein $R^{43}$ is selected from hydrogen or methyl; and
  Z² is hydrogen, (1-6C)alkyl, aryl, (3-6C)cycloalkyl, heteroaryl or heterocyclyl;
  and wherein Z² is optionally further substituted by one or more substituent groups independently selected from oxo, halo, cyano, hydroxy, N$R^{44}R^{45}$, (1-4C)alkoxy or (1-4C)alkyl, wherein $R^{44}$ and $R^{45}$ are each independently selected from hydrogen, or (1-2C)alkyl;
(13) $R_2$ is selected from:
  (i) —C(O)OH;
  (ii) —C(O)O$R_{2A}$, wherein $R_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups $R^A$;

(iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^A$;
(iv) —C(O)NR$_{2D}$NR$_{2B}$R$_{2C}$; wherein R$_{2D}$ is selected from hydrogen or (1-6C)alkyl and R$_{2B}$ and R$_{2C}$ are as defined above;
(v) tetrazolyl;
(vi) triazolyl;
(vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
(viii) trifluoromethylketone; or
(ix) cyano

(14) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, (3-8C)cycloalkyl, aryl, heteroaryl or heterocyclyl, each of which is optionally substituted by one or more substituent groups R$^A$;
(iii) —C(O)NR$_{2D}$NR$_{2B}$R$_{2C}$; wherein R$_{2D}$ is selected from hydrogen or (1-2C)alkyl and R$_{2B}$ and R$_{2C}$ are as defined above;
(iv) tetrazolyl;
(v) —B(OR$_2$F)(OR$_{2G}$), wherein R$_{2F}$ and R$_{2G}$ are each independently selected from hydrogen, (1-4C)alkyl or R$_{2F}$ and R$_{2G}$ are linked such that, together with the B and O atoms, they form a 5 or 6-membered heterocyclic ring, which is optionally substituted by (1-2C)alkyl; or
(vi) cyano;
and wherein R$^A$ is selected from halo, cyano, or a group of the formula:

—X$^2$—Z$^2$ wherein
X$^2$ is absent or —C(O)—, —SO$_2$—; and
Z$^2$ is hydrogen, (1-6C)alkyl, aryl, or heteroaryl;
and wherein Z$^2$ is optionally further substituted by one or more substituent groups independently selected from halo, hydroxy, NR$^{44}$R$^{45}$, (1-4C)alkoxy or (1-4C)alkyl, wherein R$^{44}$ and R$^4$S are each independently selected from hydrogen, or (1-2C)alkyl;

(15) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, (3-8C)cycloalkyl, aryl or heteroaryl, each of which is optionally substituted by one or more substituent groups R$^A$;
(iii) —C(O)NR$_{2D}$NR$_{2B}$R$_{2C}$; wherein R$_{2D}$ is selected from hydrogen or (1-2C)alkyl and R$_{2B}$ and R$_{2C}$ are as defined above;
(iv) tetrazolyl;
(v) —B(OR$_{2F}$)(OR$_{2G}$), wherein R$_{2F}$ and R$_{2G}$ are each independently selected from hydrogen, (1-4C)alkyl or R$_{2F}$ and R$_{2G}$ are linked such that, together with the B and O atoms, they form a 5 or 6-membered heterocyclic ring, which is optionally substituted by (1-2C)alkyl; or
(vi) cyano:
and wherein R$^A$ is selected from halo, cyano, or a group of the formula:

—X$^2$—Z$^2$ wherein
X$^2$ is absent or —C(O)—, —SO$_2$—; and
Z$^2$ is hydrogen, (1-6C)alkyl, aryl, or heteroaryl;
and wherein Z$^2$ is optionally further substituted by one or more substituent groups independently selected from halo, hydroxy, NR$^{44}$R$^{45}$, (1-4C)alkoxy or (1-4C)alkyl, wherein R$^{44}$ and R$^{45}$ are each independently selected from hydrogen, or (1-2C)alkyl;

(16) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, aryl or heteroaryl, each of which is optionally substituted by one or more substituent groups R$^A$;
(iii) —C(O)NR$_{2D}$NR$_{2B}$R$_{2C}$; wherein R$_{2D}$ is selected from hydrogen or methyl and R$_{2B}$ and R$_{2C}$ are as defined above;
(iv) tetrazolyl; or
(v) cyano;
and wherein R$^A$ is selected from halo, cyano, or a group of the formula:

—X$^2$—Z$^2$ wherein
X$^2$ is absent or —C(O)—, —SO$_2$—; and
Z$^2$ is hydrogen, (1-4C)alkyl, phenyl, or a 5- or 6-membered heteroaryl;
and wherein Z$^2$ is optionally further substituted by one or more substituent groups independently selected from halo, hydroxyl or (1-4C)alkyl;

(17) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, aryl or heteroaryl, each of which is optionally substituted by one or more substituent groups R$^A$;
(iii) —C(O)NR$_{2D}$NR$_{2B}$R$_{2C}$; wherein R$_{2D}$ is selected from hydrogen or methyl and R$_{2B}$ and R$_{2C}$ are as defined above;
(iv) tetrazolyl; or
(v) cyano;
and wherein R$^A$ is selected from halo, cyano or SO$_2$CH$_3$;
4C)alkyl;

(18) R$_2$ is selected from:
(i) —C(O)OH;
(ii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^A$; or
(iii) tetrazolyl; or
(iv) cyano;
and wherein R$^A$ is selected from halo, cyano, nitro or a group of the formula:

—Y$^2$—X$^2$—Z$^2$ wherein
- Y$^2$ is absent or a linker group of the formula —[CR$^{A1}$R$^{A2}$]$_m$— in which m is an integer selected from 1 or 2, and R$^{A1}$ and R$^{A2}$ are each independently selected from hydrogen or (1-2C)alkyl;
- X$^2$ is absent or —O—, —C(O)—, —C(O)O—, —OC(O)—, —N(R$^{A3}$)—, —N(R$^{A3}$)—C(O), —N(R$^{A3}$)—C(O)O—, —C(O)—N(R$^{A3}$)—, —N(R$^{A3}$)C(O)N(R$^{A3}$), —SO$_2$—, —S(O)$_2$N(R$^{A3}$)—, or —N(R$^{A3}$)SO$_2$— wherein R$^{A3}$ is selected from hydrogen or methyl; and
- Z$^2$ is hydrogen, (1-6C)alkyl, aryl, (3-6C)cycloalkyl, (3-6C)cycloalkenyl, heteroaryl or heterocyclyl;
  and wherein Z$^2$ is optionally further substituted by one or more substituent groups independently selected from oxo, halo, cyano, nitro, hydroxy, carboxy, NR$^{A4}$R$^{A5}$, (1-4C)alkoxy, (1-40)alkyl, (3-80)cycloalkyl, (1-4C)alkanoyl, (1-4C)alkylsulphonyl, C(O)NR$^{A4}$R$^{A5}$, NR$^{A4}$C(O)R$^{A5}$, NR$^{A4}$S(O)$_2$R$^{A5}$ and S(O)$_2$NR$^{A4}$R$^{A5}$; wherein R$^{A4}$ and R$^{A5}$ are each independently selected from hydrogen, or (1-4C)alkyl; or R$^{A4}$ and R$^{A5}$ can be linked such that, together with the nitrogen atom to which they are attached, they form a 4-6 membered heterocyclic ring;

(19) R$_2$ is selected from:
  (i) —C(O)OH;
  (ii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^4$;
  (iii) tetrazolyl; or
  (iv) cyano;
    and wherein R$^4$ is selected from halo, cyano, or a group of the formula:

—X$^2$—Z$^2$ wherein
    X$^2$ is absent or —C(O)—, —SO$_2$—; and
    Z$^2$ is hydrogen, (1-4C)alkyl, phenyl, or a 5- or 6-membered heteroaryl; and wherein Z$^2$ is optionally further substituted by one or more substituent groups independently selected from halo, hydroxyl or (1-4C)alkyl;

(20) R$_2$ is selected from:
  (i) —C(O)OH;
  (ii) —C(O)NR$_{2B}$R$_{2C}$; wherein R$_{2B}$ and R$_{2C}$ are each independently selected from hydrogen, (1-6C)alkyl, aryl or heteroaryl, each of which is optionally substituted by one or more substituent groups R$^4$; or
  (iii) tetrazolyl;
    and wherein R$^4$ is selected from halo, cyano or SO$_2$CH$_3$;

(21) R$_2$ is —C(O)OH, —C(O)NH$_2$, tetrazolyl or cyano;
(22) R$_2$ is —C(O)OH, —C(O)NH$_2$ or tetrazolyl;
(23) R$_2$ is —C(O)OH or —C(O)NH$_2$;
(24) R$_2$ is —C(O)OH or tetrazolyl;
(25) R$_2$ is —C(O)OH;
(26) R$_3$ is selected from hydrogen, halo, cyano, hydroxy, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;
R$^B$ is halo, cyano, nitro, hydroxy or a group:

—Y$^3$—X$^3$—Z$^3$ wherein
- Y$^3$ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
- X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —S—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
- Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
  and wherein Z$^3$ is optionally further substituted by one or more substituent groups independently selected from oxo, halo, cyano, nitro, hydroxy, carboxy, NR$^{B5}$R$^{B6}$, (1-40)alkoxy, (1-4C)alkyl, (3-80)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$ wherein R$^{B5}$ and R$^{B6}$ are each independently selected from hydrogen, (1-4C)alkyl or (3-6C)cycloalkyl or (3-6C)cycloalkyl(1-2C)alkyl; or R$^{B5}$ and R$^{B6}$ can be linked such that, together with the nitrogen atom to which they are attached, they form a 4-7 membered heterocyclic ring;
  and wherein any alkyl, aryl, heterocyclyl or heteroaryl group present in a substituent group on Z$^3$ is optionally further substituted by halo, cyano, nitro, hydroxy, caboxy, NR$^{B7}$R$^{B8}$, (1-20)alkoxy, or (1-2C)alkyl; wherein R$^{B7}$ and R$^{B8}$ are selected from hydrogen or (1-2C)alkyl;

(27) R$_3$ is selected from hydrogen, halo, cyano, hydroxy, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;
R$^B$ is halo, cyano, nitro, hydroxy or a group:

—Y$^3$—X$^3$—Z$^3$ wherein
- Y$^3$ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
- X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
- Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^3$ is optionally further substituted by one or more substituent groups independently selected from oxo, halo, cyano, nitro, hydroxy, carboxy, $NR^{B5}R^{B6}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$ wherein R$^{B5}$ and R$^{B6}$ are each independently selected from hydrogen, (1-4C)alkyl or (3-6C)cycloalkyl or (3-6C)cycloalkyl(1-2C)alkyl; or R$^{B5}$ and R$^{B6}$ can be linked such that, together with the nitrogen atom to which they are attached, they form a 4-7 membered heterocyclic ring;

(28) $R_3$ is selected from hydrogen, halo, cyano, hydroxy, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;

R$^B$ is halo, cyano, nitro, hydroxy or a group:

—Y$^3$—X$^3$—Z$^3$ wherein
Y$^3$ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^3$ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$; wherein R$^{B5}$ andR$^B$ are each independently selected from hydrogen, (1-4C)alkyl or (3-6C)cycloalkyl or (3-6C)cycloalkyl(1-2C)alkyl; or R$^{B5}$ andR$^{B6}$ can be linked such that, together with the nitrogen atom to which they are attached, they form a 4-7 membered heterocyclic ring;

(29) $R_3$ is selected from hydrogen, halo, cyano, hydroxy, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more R$^B$;

R$^B$ is halo, cyano, nitro, hydroxy or a group:

—Y$^3$—X$^3$—Z$^3$ wherein
Y$^3$ is absent or a linker group of the formula —[CR$^{B1}$R$^{B2}$]$_n$— in which n is an integer selected from 1, 2, 3 or 4, and R$^{B1}$ and R$^{B2}$ are each independently selected from hydrogen or (1-2C)alkyl;
X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$), —N(R$^{B4}$)C(O)N(R$^{B3}$)—, —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^3$ is optionally further substituted by one or more substituent groups independently selected from oxo, halo, cyano, nitro, hydroxy, carboxy, NR$^B$R$^{B6}$, (1-4C)alkoxy, (1-4C)alkyl, (1-4C)alkanoyl, (1-4C)alkylsulphonyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$ wherein R$^{B5}$ and R$^{B6}$ are each independently selected from hydrogen, (1-4C)alkyl or (3-6C)cycloalkyl or (3-6C)cycloalkyl(1-2C)alkyl;

(30) $R_3$ is selected from hydrogen, halo, cyano, hydroxy, aryl, (1-6C)alkyl, (2-6C)alkenyl, heteroaryl or heterocyclyl, wherein said aryl, heteroaryl or heterocyclyl is optionally substituted by one or more R$^B$;

R$^B$ is halo, cyano, nitro, hydroxy or a group:

—Y$^3$—X$^3$—Z$^3$ wherein
Y$^3$ is absent or a linker group of the formula —[CR$^{B1}$R$^{B2}$] in which n is an integer selected from 1, 2, 3 or 4, and R$^{B1}$ and R$^{B2}$ are each independently selected from hydrogen or (1-2C)alkyl;
X$^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$), —SO—, —SO$_2$—, —S(O)$_2$N(R$^{B3}$)—, or —N(R$^{B4}$)SO$_2$— wherein R$^{B3}$ and R$^{B4}$ are each independently selected from hydrogen or methyl; and
Z$^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein Z$^3$ is optionally further substituted by one or more substituent groups independently selected from oxo, halo, cyano, nitro, hydroxy, carboxy, NR$^{B5}$B$^{B6}$, (1-4C)alkoxy, (1-4C)alkyl, (1-4C)alkanoyl, (1-4C)alkylsulphonyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$; wherein R$^{B5}$ and R$^{B6}$ are each independently selected from hydrogen, (1-4C)alkyl or (3-6C)cycloalkyl or (3-6C)cycloalkyl(1-2C)alkyl;

(31) $R_3$ is selected from hydrogen, halo, cyano, hydroxy, aryl, (1-6C)alkyl, (2-6C)alkenyl, 5- or 6-membered heteroaryl or 5- or 6-membered heterocyclyl, wherein said aryl, heteroaryl or heterocyclyl is optionally substituted by one or more R$^B$;

R$^B$ is halo, cyano, nitro, hydroxy or a group:

—Y$^3$—X$^3$—Z$^3$ wherein
- $Y^3$ is absent or a linker group of the formula $—[CR^{B1}R^{B2}]_n—$ in which n is an integer selected from 1 or 2, and $R^{B1}$ and $R^{B2}$ are each independently selected from hydrogen or (1-2C)alkyl;
- $X^3$ is absent or —O—, —C(O)—, —C(O)O—, —OC(O)—, —N($R^{B3}$)—, —N($R^{B4}$)—C(O)—, —N($R^{B4}$)—C(O)O—, —C(O)—N($R^{B3}$) —S—, —SO—, or $O_2$—, wherein $R^{B3}$ and $R^{B4}$ are each independently selected from hydrogen or methyl; and
- $Z^3$ is hydrogen, (1-6C)alkyl, (2-6C)alkenyl, (2-6C)alkynyl, aryl, (3-6C)cycloalkyl, (3-6C)cycloalkenyl, 5- or 6-membered heteroaryl or 5- or 6-membered heterocyclyl;
- and wherein $Z^3$ is optionally further substituted by one or more substituent groups independently selected from oxo, halo, cyano, nitro, hydroxy, carboxy, $NR^{B5}R^{B6}$, (1-4C)alkoxy, (1-4C)alkyl, (1-4C)alkanoyl, (1-4C)alkylsulphonyl, C(O)$NR^{B5}R^{66}$, $NR^{B5}C(O)R^{B6}$, $NR^{B5}S(O)_2R^{B6}$ and $S(O)_2NR^{B5}R^{B6}$; wherein $R^{B5}$ and $R^{B6}$ are each independently selected from hydrogen or (1-4C)alkyl;

(32) $R_3$ is selected from hydrogen, halo, cyano, hydroxy, aryl, (1-6C)alkyl, (2-6C)alkenyl, 5- or 6-membered heteroaryl or 5- or 6-membered heterocyclyl, wherein said aryl, heteroaryl or heterocyclyl is optionally substituted by one or more $R^B$;
$R^B$ is halo, cyano, nitro, hydroxy or a group:

$$—Y^3—X^3—Z^3$$

wherein
- $Y^3$ is absent or a linker group of the formula $—[CR^{B1}R^{B2}]_n—$ in which n is an integer selected from 1 or 2, and $R^{B1}$ and $R^{B2}$ are each independently selected from hydrogen or (1-2C)alkyl;
- $X^3$ is absent or —O—, —C(O)—, —C(O)O—, —OC(O)—, —N($R^{B3}$)—, —N($R^{B4}$)—C(O)—, —C(O)—N($R^{B3}$), —SO—, or $SO_2$—, wherein $R^{B3}$ and $R^{B4}$ are each independently selected from hydrogen or methyl; and
- $Z^3$ is hydrogen, (1-6C)alkyl, aryl, (3-6C)cycloalkyl, (3-6C)cycloalkenyl, 5- or 6-membered heteroaryl or 5- or 6-membered heterocyclyl;
- and wherein $Z^3$ is optionally further substituted by one or more substituent groups independently selected from oxo, halo, cyano, nitro, hydroxy, carboxy, $NR^{B5}B^{B6}$, (1-2C)alkoxy, (1-2C)alkyl, (1-2C)alkanoyl, or (1-2C)alkylsulphonyl; wherein $R^{B5}$ and $R^{B6}$ are each independently selected from hydrogen or (1-2C)alkyl;

(33) $R_3$ is selected from hydrogen, halo, cyano, hydroxy, aryl, (1-6C)alkyl, (2-6C)alkenyl, 5- or 6-membered heteroaryl or 5- or 6-membered heterocyclyl, wherein said aryl, heteroaryl or heterocyclyl is optionally substituted by one or more $R^B$;
$R^B$ is halo, cyano, nitro, hydroxy or a group:

$$—Y^3—X^3—Z^3$$

wherein
- $Y^3$ is absent or a linker group of the formula $—[CR^{B1}R^{B2}]_n—$ in which n is an integer selected from 1 or 2, and $R^{B1}$ and $R^{B2}$ are each independently selected from hydrogen or (1-2C)alkyl;
- $X^3$ is absent or —O—, —C(O)—, —C(O)O—, —OC(O)—, —N($R^{B3}$)—, —N($R^{B4}$)—C(O)—, —C(O)—N($R^{B3}$)—, —S—, —SO—, or —$SO_2$—, wherein $R^{B3}$ and $R^{B4}$ are each independently selected from hydrogen or methyl; and
- $Z^3$ is hydrogen, (1-6C)alkyl, aryl or 5- or 6-membered heteroaryl;
- and wherein $Z^3$ is optionally further substituted by one or more substituent groups independently selected from oxo, halo, cyano, nitro, hydroxy, carboxy, amino, (1-2C)alkoxy or (1-2C)alkyl;

(34) $R_3$ is selected from hydrogen, halo, cyano, hydroxy, aryl, (1-6C)alkyl, (2-6C)alkenyl, 5- or 6-membered heteroaryl or 5- or 6-membered heterocyclyl, wherein said aryl, heteroaryl or heterocyclyl is optionally substituted by one or more $R^B$;
$R^B$ is halo, cyano, nitro, hydroxy or a group:

$$—Y^3—X^3—Z^3$$

wherein
- $Y^3$ is absent or a linker group of the formula $—[CR^{B1}R^{B2}]_n—$ in which n is an integer selected from 1 or 2, and $R^{B1}$ and $R^{B2}$ are each independently selected from hydrogen or (1-2C)alkyl;
- $X^3$ is absent or —O—, —C(O)—, —C(O)O—, —OC(O)—, —N($R^{B3}$)—, —N($R^{B4}$)—C(O)—, —(O)—N($R^{B3}$) —S—, —SO—, or $O_2$—, wherein $R^{B3}$ and $R^{B4}$ are each independently selected from hydrogen or methyl; and
- $Z^3$ is hydrogen, (1-6C)alkyl, aryl or 5- or 6-membered heteroaryl;
- and wherein $Z^3$ is optionally further substituted by one or more substituent groups independently selected from oxo, halo, cyano, nitro, hydroxy, carboxy, amino, (1-2C)alkoxy or (1-2C)alkyl;

(35) $R_3$ is selected from hydrogen, halo, aryl or 5- or 6-membered heteroaryl, wherein said aryl or heteroaryl is optionally substituted by one or more $R^B$.
$R^B$ is halo, cyano, nitro, hydroxy or a group:

$$—Y^3—X^3—Z^3$$

wherein
- $Y^3$ is absent or a linker group of the formula $—[CR^{B1}R^{B2}]_n—$ in which n is an integer selected from 1 or 2, and $R^{B1}$ and $R^{B2}$ are each independently selected from hydrogen or methyl;
- $X^3$ is absent or —O—, —C(O)—, —C(O)O—, —N($R^{B3}$)—, —C(O)N($R^{B3}$)—, —S—, —SO—, or —$O_2$—, wherein $R^{B3}$ and $R^{B4}$ are each independently selected from hydrogen or methyl; and
- $Z^3$ is hydrogen, (1-6C)alkyl, aryl or 5- or 6-membered heteroaryl;
- and wherein $Z^3$ is optionally further substituted by one or more substituent groups independently selected from oxo, halo, cyano, nitro, hydroxy, carboxy, amino, (1-2C)alkoxy or (1-2C)alkyl;

(36) $R_3$ is selected from hydrogen, halo, aryl or 5- or 6-membered heteroaryl, wherein said aryl or heteroaryl is optionally substituted by one or more $R^B$;
$R^B$ is halo, hydroxy, (1-4C)alkyl, (1-4C)alkoxy, (1-2C)alkylsulphonyl, sulphonyl, mercapto, amino, carbonyl, carboxy, amido or nitro;

(37) $R_3$ is selected from hydrogen, halo or aryl, wherein said aryl or heteroaryl is optionally substituted by one or more $R^B$;
$R^B$ is halo, hydroxy, (1-4C)alkyl, (1-4C)alkoxy, (1-2C)alkylsulphonyl, sulphonyl, mercapto, amino, carbonyl, carboxy, amido or nitro;

(38) $R_3$ is selected from hydrogen, halo or phenyl, wherein said aryl or heteroaryl is optionally substituted by one or more $R^B$;
$R^B$ is halo, hydroxy, (1-4C)alkyl, (1-4C)alkoxy, (1-2C)alkylsulphonyl, sulphonyl, mercapto, amino, carbonyl, carboxy, amido or nitro;

(39) $R_3$ is selected from hydrogen, bromo or phenyl, wherein said aryl or heteroaryl is optionally substituted by one or more $R^B$;
$R^B$ is halo, hydroxy, (1-2C)alkyl, (1-2C)alkoxy, (1-2C)alkylsulphonyl, sulphonyl, mercapto, amino or carboxy;

(40) $X_1$ is N;

(41) $X_1$ is C—$R_4$;

(42) $R_4$ is selected from halo, cyano, nitro, hydroxy or a group

—$Y^4$—$X^4$—$Z^4$ wherein:
$Y^4$ is absent or a linker group of the formula —$[CR^{4A}R^{4B}]_q$— in which q is an integer selected from 1 or 2 and $R^{4A}$ and $R^{4B}$ are each independently selected from hydrogen or methyl;
$X^4$ is absent or —O—, —C(O)—, —C(O)O—, —OC(O)—, —N($R^{4C}$)—, —N($R^{4D}$)—C(O)—, —C(O)—N($R^{4C}$)—, —S—, —SO—, —SO$_2$—, —S(O)$_2$N($R^{4C}$)—, or —N($R^{4D}$)SO$_2$— wherein $R^{4C}$ and $R^{4D}$ are each independently selected from hydrogen or (1-4C)alkyl; and
$Z^4$ is hydrogen or (1-4C)alkyl which is optionally further substituted by one or more substituent groups independently selected from oxo, halo, cyano, nitro, hydroxy, carboxy, NR$^{4E}$R$^{4F}$ or (1-20)alkoxy; wherein $R^{4E}$ and $R^{4F}$ are each independently selected from hydrogen or (1-2C)alkyl;

(43) $R_4$ is selected from halo, cyano, nitro, hydroxy or a group

—$Y^4$—$X^4$—$Z^4$ wherein:
$Y^4$ is absent or a linker group of the formula —$[CR^{4A}R^{4B}]_q$— in which q is an integer selected from 1 or 2 and $R^{4A}$ and $R^{4B}$ are each independently selected from hydrogen or methyl;
$X^4$ is absent or —O—, —C(O)—, —C(O)O—, —OC(O)—, —N($R^{4C}$)—, —N($R^{4D}$)—C(O)—, —C(O)—N($R^{4C}$)—, —S—, —SO— or —SO$_2$—, wherein $R^{4C}$ and $R^{4D}$ are each independently selected from hydrogen or (1-4C)alkyl; and
$Z^4$ is hydrogen or (1-4C)alkyl which is optionally further substituted by one or more substituent groups independently selected from oxo, halo, cyano, nitro, hydroxy, carboxy, amino or (1-2C)alkoxy;

(44) $R_4$ is selected from halo, cyano, nitro, hydroxy or a group

—$Y^4$—$X^4$—$Z^4$ wherein:
$Y^4$ is absent or a linker group of the formula —[CH$_2$]—;
$X^4$ is absent or —O—, —C(O)—, —C(O)O—, —OC(O)—, —N($R^{4C}$)—, —N($R^{4C}$)—C(O)—, —C(O)—N($R^{4C}$)—, —S—, —SO— or —SO$_2$—, wherein $R^{4C}$ and $R^{4D}$ are each independently selected from hydrogen or (1-2C)alkyl; and
$Z^4$ is hydrogen or (1-4C)alkyl which is optionally further substituted by one or more substituent groups independently selected from oxo, halo, cyano, nitro, hydroxy, carboxy, amino or (1-2C)alkoxy;

(45) $R_4$ is selected from halo, cyano, nitro, hydroxy or a group

—$X^4$—$Z^4$ wherein:
$X^4$ is absent or —O—, —C(O)—, —C(O)O—, —OC(O)—, —N($R^{4C}$)—, —N($R^{4D}$)—C(O)—, —C(O)—N($R^{4C}$)—, —S—, —SO— or —SO$_2$—, wherein $R^{4C}$ and $R^{4D}$ are each independently selected from hydrogen or (1-2C)alkyl; and
$Z^4$ is hydrogen or (1-4C)alkyl which is optionally further substituted by one or more substituent groups independently selected from oxo, halo, cyano, nitro, hydroxy, carboxy, amino or (1-2C)alkoxy;

(46) $R_4$ is selected from halo, cyano, nitro, hydroxy or (1-4C)alkyl, wherein said (1-4C)alkyl is optionally further substituted by one or more substituent groups independently selected from oxo, halo, cyano, nitro, hydroxy, carboxy, amino or (1-2C)alkoxy;

(47) $R_4$ is selected from halo, cyano, nitro, hydroxy or (1-4C)alkyl;

(48) $R_4$ is selected from halo or (1-4C)alkyl;

(49) $R_4$ is (1-4C)alkyl (e.g. methyl or ethyl);

(50) $R_5$ is selected from hydrogen, halo, cyano, nitro, hydroxy or a group of the formula:

—$Y^5$—$X^5$-$Q^5$-$Z^5$ wherein
$Y^5$ is absent or a linker group of the formula —$[CR^{5A}R^{5B}]_p$— in which p is an integer selected from 1 or 2, and $R^{5A}$ and $R^{5B}$ are each independently selected from hydrogen or (1-2C)alkyl;
$X^5$ is absent or —O—, —C(O)—, —C(O)O—, —OC(O)—, —N($R^{5C}$)—, —N($R^{5D}$)—C(O)—, —C(O)—N($R^{5C}$)—, —S—, —SO—, —SO$_2$—, —S(O)$_2$N($R^{5C}$)—, or —N($R^{5D}$)SO$_2$— wherein $R^{5C}$ and $R^{5D}$ are each independently selected from hydrogen or (1-6C)alkyl;
$Q^5$ is absent or a (1-4C)alkylene optionally interrupted by one or more O atoms; and
$Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein $Z^5$ is optionally further substituted by one or more substituent groups independently selected from oxo, halo, cyano, nitro, hydroxy, carboxy, NR$^{5E}$R$^{5F}$, (1-4C)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, C(O)R$^{5E}$C(O)OR$^{5E}$, OC(O)R$^{5E}$, C(O)NR$^{5E}$R$^{5F}$, NR$^{5E}$C(O)R$^{5F}$, NR$^{5E}$S(O)$_2$R$^{5F}$ and S(O)$_2$NR$^{5E}$R$^{5F}$; wherein $R^{5E}$ and $R^{5F}$ are each independently selected from hydrogen, (1-4C)alkyl, (1-4C)haloalkyl or (3-6C)cycloalkyl; or $R^{5E}$ and $R^{5F}$ can be linked such that, together with the nitrogen atom to which they are attached, they form a 4-7 membered heterocyclic ring;

and wherein any alkyl, aryl, heterocyclyl or heteroaryl group present in a substituent group on $Z^5$ is optionally further substituted by one or more substituents selected from halo, (1-2C)haloalkyl, cyano, nitro, hydroxy, caboxy, $NR^{5G}R^{5H}$, (1-2C)alkoxy, or (1-2C)alkyl; wherein RG and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$ (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; or $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituent groups selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl, (1-4C)haloalkyl or (3-6C)cycloalkyl;

(51) $R_5$ is selected from hydrogen, halo, cyano, nitro, hydroxy or a group of the formula:

—$Y^5$—$X^5$—$Z^5$ wherein $Y^5$ is absent or a linker group of the formula —$[CR^{5A}R^{5B}]_p$— in which p is an integer selected from 1 or 2, and $R^{5A}$ and $R^{5B}$ are each independently selected from hydrogen or (1-2C)alkyl;

$X^5$ is absent or —O—, —C(O)—, —C(O)—, —OC(O)—, —N($R^{5C}$)—, —N($R^{5D}$)—C(O), —C(O)—N($R^{5C}$)—, —S—, —SO—, —SO$_2$—, —S(O)$_2$N($R^C$)—, or —N($R^D$)SO$_2$— wherein $R^{5C}$ and $R^D$ are each independently selected from hydrogen or (1-6C)alkyl; and $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, $C(O)R^{5E}$, $C(O)OR^{5E}$, $OC(O)^{5E}$, $C(O)NR^{5E}R^{5F}$, $NR^{5E}C(O)RIF$, $NR^{5E}S(O)_2R^{5F}$ and $S(O)_2NR^{5E}R^{5F}$; wherein $R^{5E}$ and $R^{5F}$ are each independently selected from hydrogen, (1-4C)

alkyl, (1-4C)haloalkyl or (3-6C)cycloalkyl; or $R^{5E}$ and $R^{5F}$ can be linked such that, together with the nitrogen atom to which they are attached, they form a 4-7 membered heterocyclic ring;

and wherein any alkyl, aryl, heterocyclyl or heteroaryl group present in a substituent group on $Z^5$ is optionally further substituted by one or more substituent groups selected from halo, cyano, nitro, hydroxy, caboxy, $NR^{5G}R^{5H}$, (1-2)alkoxy, or (1-2C)alkyl; wherein $R^{5G}$ and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$ (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; or $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl, (1-4C)haloalkyl or (3-6C)cycloalkyl;

(52) $R_5$ is selected from hydrogen, halo, cyano, nitro, hydroxy or a group of the formula:

—$Y^5$—$X^5$-$Q^5$-$Z^5$ wherein $Y^5$ is absent or a linker group of the formula —$[CR^{5A}R^{5B}]_p$— in which p is an integer selected from 1 or 2, and $R^{5A}$ and $R^{5B}$ are each independently selected from hydrogen or (1-2C)alkyl;

$X^5$ is absent or —O—, —C(O)—, —C(O)O—, —OC(O)—, —N($R^{5C}$)—, —N($R^{5D}$)—C(O)—, —(O)—N($R^{5C}$)—, —S—, —SO—, —SO$_2$—, —S(O)$_2$N($R^{5C}$)—, or —N($R^{5D}$)SO$_2$— wherein $R^{5C}$ and $R^{5D}$ are each independently selected from hydrogen or (1-6C)alkyl;

$Q^5$ is absent or a (1-3C)alkylene optionally interrupted by one or more O atoms; and $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^5$ is optionally further substituted by one or more substituent groups independently selected from oxo, halo, cyano, nitro, hydroxy, carboxy, $NR^{5E}R^{5F}$, (1-40)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$ wherein $R^{5E}$ and $R^{5F}$ are each independently selected from hydrogen, (1-4C)alkyl, (1-4C)haloalkyl or (3-6C)cycloalkyl; or $R^{5E}$ and $R^{5F}$ can be linked such that, together with the nitrogen atom to which they are attached, they form a 4-7 membered heterocyclic ring;

and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-2C)alkoxy, or (1-2C)alkyl; wherein $R^{5G}$ and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by one or more substituent groups selected from oxo, halo, (1-2C)haloalkyl, cyano, nitro, hydroxy, carboxy, $NR^{5E}R^{5F}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5E}$, $C(O)OR^{5E}$, $C(O)NR^{5E}R^{5F}$ or $NR^{5E}C(O)R^{5F}$; or $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl or (3-6C)cycloalkyl;

(53) $R_5$ is selected from hydrogen, halo, cyano, nitro, hydroxy or a group of the formula:

—$Y^5$—$X^5$—$Z^5$ wherein $Y^5$ is absent or a linker group of the formula —$[CR^{5A}R^{5B}]_p$— in which p is an integer selected from 1 or 2, and $R^{5A}$ and $R^{5B}$ are each independently selected from hydrogen or (1-2C)alkyl;

$X^5$ is absent or —O—, —C(O)—, —C(O)O—, —OC(O)—, —N($R^{5C}$)—, —N($R^{5D}$)—C(O)—, —C(O)—N($R^{5C}$)—, —S—, —SO—, —SO$_2$—, —S(O)$_2$N($R^{5C}$)—, or —N($R^D$)SO$_2$— wherein $R^{5C}$ and $R^{5D}$ are each independently selected from hydrogen or (1-6C)alkyl; and $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^5$ is optionally further substituted by one or more substituent groups independently selected from oxo, halo, cyano, nitro, hydroxy, carboxy, $NR^{5E}R^{5F}$, (1-40)alkoxy, (1-40)alkyl, (1-40)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, $C(O)R^{5E}$, $C(O)OR^{5E}$, $OC(O)R^{5E}$, $C(O)NR^{5E}R^{5F}$, $NR_{5E}C(O)R^{5F}$, $NR^{5E}S(O)_2R^{5F}$ and $S(O)_2NR^{5E}R^{5F}$; wherein $R^{5E}$ and $R^{5F}$ are each independently selected from hydrogen, (1-4C)alkyl, (1-4C)haloalkyl or (3-6C)cycloalkyl; or $R^{5E}$ and $R^{5F}$ can be linked such that, together with the nitrogen atom to which they are attached, they form a 4-7 membered heterocyclic ring;

and wherein any alkyl, aryl, heterocyclyl or heteroaryl group present in a substituent group on $Z^5$ is optionally further substituted by one or more substituent groups selected from halo, cyano, nitro, hydroxy, caboxy, $NR^{5G}R^{5H}$, (1-2)alkoxy, or (1-2C)alkyl; wherein $R^{5G}$ and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5E}$, $C(O)OR^{5E}$, $C(O)NR^{5E}R^{5F}$ or $NR^{5E}C(O)R^{5F}$; or $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl or (3-6C)cycloalkyl;

(54) $R_5$ is selected from hydrogen, halo, cyano, nitro, hydroxy or a group of the formula:

—$Y^5$—$X^5$-$Q^5$-$Z^5$ wherein $Y^5$ is absent or a linker group of the formula —$[CR^{5A}R^{5B}]_p$— in which p is an integer selected from 1 or 2, and $R^{5A}$ and $R^{5B}$ are each independently selected from hydrogen or (1-2C)alkyl;

$X^5$ is absent or —O—, —C(O)—, —C(O)O—, —OC(O)—, —N($R^{5C}$)—, —N($R^{5D}$)—C(O)—, —C(O)—N($R^{5C}$)—, —S—, —SO—, —SO$_2$—, —S(O)$_2$N($R^{5C}$)—, or —N($R^{5D}$)SO$_2$— wherein $R^{5C}$ and $R^{5D}$ are each independently selected from hydrogen or (1-6C)alkyl;

$Q^5$ is absent or —CH$_2$O—; and $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^5$ is optionally further substituted by one or more substituent groups independently selected from oxo, halo, cyano, nitro, hydroxy, carboxy, $NR^{5E}R^{5F}$, (1-40)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$ wherein $R^{5E}$ and $R^{5F}$ are each independently selected from hydrogen, (1-4C)
alkyl, (1-4C)haloalkyl or (3-6C)cycloalkyl;
and wherein any alkyl, aryl, heterocyclyl or heteroaryl group present in a substituent group on $Z^5$ is optionally further substituted by one or more substituent groups selected from halo, cyano, nitro, hydroxy, caboxy, $NR^{5G}R^{5H}$, (1-2)alkoxy or (1-2)alkyl; wherein $R^{5G}$ and $R^{5H}$ are selected from hydrogen or (1-2C)alkyl;
or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$ (1-4C)alkoxy, (1-4C)alkyl or (1-4C)haloalkyl; or
$R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl or (3-6C)cycloalkyl;

(55) $R_5$ is selected from hydrogen, halo, cyano, nitro, hydroxy or a group of the formula:

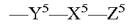
—$Y^5$—$X^5$—$Z^5$ wherein
$Y^5$ is absent or a linker group of the formula —[$CR^{5A}R^{5B}$]$_p$— in which p is an integer selected from 1 or 2, and $R^{5A}$ and $R^{5B}$ are each independently selected from hydrogen or (1-2C)alkyl;
$X^5$ is absent or —O—, —C(O)—, —C(O)O—, —OC(O)—, —N($R^{5C}$)—, —N($R^{5D}$)—C(O)—, —C(O)—N($R^{5C}$)—, —S—, —SO—, —SO$_2$—, —S(O)$_2$N($R^{5C}$)—, or —N($R^{5D}$)SO$_2$— wherein $R^{5C}$ and $R^{5D}$ are each independently selected from hydrogen or (1-6C)alkyl; and
$Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein $Z^5$ is optionally further substituted by one or more substituent groups independently selected from oxo, halo, cyano, nitro, hydroxy, carboxy, $NR^{5E}R^{5F}$, (1-40)alkoxy, (1-40)alkyl, (1-40)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; wherein $R^{5E}$ and $R^{5F}$ are each independently selected from hydrogen, (1-4C)alkyl, (1-4C)haloalkyl or (3-6C)cycloalkyl;
and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-20)alkoxy or (1-2C)alkyl; wherein $R^{5G}$ and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$, (1-4C)alkoxy, (1-4C)alkyl or (1-4C)haloalkyl; or
$R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl or (3-6C)cycloalkyl;

(56) $R_5$ is selected from hydrogen, halo, cyano, nitro, hydroxy or a group of the formula:

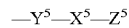
—$Y^5$—$X^5$—$Z^5$ wherein
$Y$ is absent or a linker group of the formula —[$CH_2$]—;
$X^5$ is absent or —O—, —C(O)—, —C(O)O—, —OC(O)—, —N($R^{5C}$)—, —N($R^{5D}$)—C(O)—, —C(O)—N($R^{5C}$)—, —S—, —SO—, —SO$_2$—, —S(O)$_2$N($R^{5C}$)—, or —N($R^{5D}$)SO$_2$— wherein $R^{5C}$ and $R^{5D}$ are each independently selected from hydrogen or (1-6C)alkyl; and
$Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; wherein $R^{5E}$ and $R^{5F}$ are each independently selected from hydrogen, (1-4C)alkyl, (1-4C)haloalkyl or (3-6C)cycloalkyl;
and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-20)alkoxy or (1-20)alkyl; wherein $R^{5G}$ and $R^{5H}$ are selected from hydrogen or (1-2C)alkyl;
or
$R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl or (1-4C)haloalkyl, wherein $R^{5'}$ and $R^5$ are each independently selected from hydrogen or (1-4C)alkyl;

(57) $R_5$ is selected from hydrogen, halo, cyano, nitro, hydroxy or a group of the formula:

$$-Y^5-X^5-Z^5$$

wherein
- $Y^5$ is absent or a linker group of the formula $-[CH_2]-$;
- $X^5$ is absent or $-O-$, $-C(O)-$, $-C(O)O-$, $-OC(O)-$, $-N(R^{5C})-$, $-N(R^{5D})-C(O)-$, $-C(O)-N(R^{5C})-$, $-S-$, $-SO-$, $-SO_2-$, $-S(O)_2N(R^{5C})-$, or $-N(R^{5D})SO_2-$ wherein $R^{5C}$ and $R^{5D}$ are each independently selected from hydrogen or (1-6C)alkyl; and
- $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
  - and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-8C)cycloalkyl, (1-4C)alkanoyl, (1-4C)alkylsulphonyl, aryl, aryloxy, 5- or 6-membered heterocyclyl, 5- or 6-membered heteroaryl, Si[(1-4C)alkyl]$_3$, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; wherein $R^{5E}$ and $R^{5F}$ are each independently selected from hydrogen, (1-4C)alkyl or (1-4C)haloalkyl;
  - and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-20)alkoxy or (1-2C)alkyl; wherein $R^{5G}$ and $R^{5H}$ are selected from hydrogen or (1-2)alkyl;

or
- $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl or (1-4C)haloalkyl, wherein $R^{5'}$ and $R^5$ are each independently selected from hydrogen or (1-4C)alkyl;

(58) $R_5$ is selected from hydrogen, halo, cyano, nitro, hydroxy or a group of the formula:

$$-Y^5-X^5-Z^5$$

wherein
- Y is absent or a linker group of the formula $-[CH_2]-$;
- $X^5$ is absent or $-O-$, $-C(O)-$, $-C(O)O-$, $-N(R^{5C})-$, $-C(O)-N(R^{5C})-$, $-S-$, $-SO-$, $-SO_2-$, $-S(O)_2N(R^{5C})-$, or $-N(R^{5D})SO_2-$ wherein $R^{5C}$ and $R^{5D}$ are each independently selected from hydrogen or (1-6C)alkyl; and
- $Z^5$ is hydrogen, (1-6C)alkyl, (2-6C)alkenyl, (2-6C)alkynyl, aryl, (3-6C)cycloalkyl, (3-6C)cycloalkenyl, 5- or 6-membered heteroaryl or 5- or 6-membered heterocyclyl;
  - and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-6C)cycloalkyl, (1-4C)alkanoyl, (1-4C)alkylsulphonyl, aryl, aryloxy, 5- or 6-membered heterocyclyl, 5- or 6-membered heteroaryl, Si[(1-4C)alkyl]$_3$, $C(O)R^{5E}$, $C(O)OR^{5E}$, $C(O)R^{5E}$, $C(O)NR^{5E}R^{5F}$ or $NR^{5E}C(O)R^{5F}$; wherein $R^{5E}$ and $R^{5F}$ are each independently selected from hydrogen, (1-4C)alkyl or (1-4C)haloalkyl;
  - and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-20)alkoxy or (1-20)alkyl; wherein $R^{5G}$ and $R^{5H}$ are selected from hydrogen or (1-2C)alkyl;

or
- $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl or (1-4C)haloalkyl, wherein $R^{5'}$ and $R^5$ are each independently selected from hydrogen or (1-4C)alkyl;

(59) $R_5$ is selected from hydrogen, halo, cyano, nitro, hydroxy or a group of the formula:

$$-X^5-Z^5$$

wherein
- $X^5$ is absent or $-O-$, $-C(O)-$, $-C(O)O-$, $-N(R^{5C})-$, $-C(O)-N(R^{5C})-$, $-S-$, $-SO-$, $-SO_2-$, $-S(O)_2N(R^{5C})-$, or $-N(R^{5D})SO_2-$ wherein $R^{5C}$ and $R^{5D}$ are each independently selected from hydrogen or (1-6C)alkyl; and
- $Z^5$ is hydrogen, (1-6C)alkyl, aryl, (3-6C)cycloalkyl, (3-6C)cycloalkenyl, 5- or 6-membered heteroaryl or 5- or 6-membered heterocyclyl;
  - and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-6C)cycloalkyl, (1-4C)alkanoyl, (1-4C)alkylsulphonyl, aryl, aryloxy, 5- or 6-membered heterocyclyl, 5- or 6-membered heteroaryl, Si[(1-4C)alkyl]$_3$, $C(O)R^E$, $C(O)OR^{5E}$, $OC(O)R^{5E}$, $C(O)NR^{5E}R^{5F}$ or $NR^{5E}C(O)R^{5F}$; wherein $R^{5E}$ and $R^{5F}$ are each independently selected from hydrogen, (1-4C)alkyl or (1-4C)haloalkyl;
  - and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-20)alkoxy or (1-2C)alkyl; wherein $R^{5G}$ and $R^{5H}$ are selected from hydrogen or (1-2)alkyl;

or
- $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl or (1-4C)haloalkyl, wherein $R^{5'}$ and $R^5$ are each independently selected from hydrogen or (1-4C)alkyl;

(60) $R_5$ is selected from hydrogen, halo, cyano, nitro, hydroxy or a group of the formula:

$$-X^5-Z^5$$

wherein
- $X^5$ is absent or $-N(R^{5C})-$, $-S(O)_2N(R^{5C})-$ or $-N(R^{5D})SO_2-$ wherein $R^{5C}$ is selected from hydrogen or (1-2C)alkyl; and
- $Z^5$ is hydrogen, (1-6C)alkyl, aryl, 5- or 6-membered heteroaryl or 5- or 6-membered heterocyclyl;
  - and wherein $Z^5$ is optionally further substituted by one or more substituent groups independently selected from halo, cyano, nitro, hydroxy, carboxy, $NR^{5E}R^{6F}$, (1-4C)alkoxy, (1-4C)alkyl, (1-4C)haloalkyl, (1-4C)haloalkoxy, ((1-4C)alkylsulphonyl, aryl, 5- or 6-membered heterocyclyl, 5- or 6-membered heteroaryl, $C(O)R^{6E}$, $C(O)OR^{5E}$, $C(O)NR^{5E}R^{5F}$ or $NR^{5E}C(O)R^{5F}$; wherein $R^{5E}$ and $R^{5F}$ are each independently selected from hydrogen, (1-4C)alkyl or (1-4C)haloalkyl;
  - and wherein any alkyl, aryl, heterocyclyl or heteroaryl group present in a substituent group on $Z^5$ is optionally further substituted by halo, cyano, nitro, hydroxy, amino, (1-2C)alkoxy or (1-2C)alkyl; or
- $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl or (1-4C)haloalkyl, wherein $R^{5'}$ and $R^5$ are each independently selected from hydrogen or (1-4C)alkyl;

(61) $R_5$ is selected from hydrogen, halo, cyano, nitro, hydroxy or a group of the formula:

$$-X^5-Z^5$$

wherein
- $X^5$ is absent or $-N(R^{5C})-$, $-S(O)_2N(R^{5C})-$ or $-N(R^{5D})SO_2-$ wherein $R^{5C}$ is selected from hydrogen or (1-2C)alkyl; and
- $Z^5$ is hydrogen, (1-6C)alkyl, aryl, 5- or 6-membered heteroaryl or 5- or 6-membered heterocyclyl;
  - and wherein $Z^5$ is optionally further substituted by one or more substituent groups independently selected from halo, cyano, nitro, hydroxy, carboxy, $NR^{5E}R^{5F}$, (1-4C)alkoxy, (1-4C)alkyl, (1-4C)haloalkyl, (1-4C)haloalkoxy, ((1-4C)alkylsulphonyl, aryl, 5- or 6-membered heterocyclyl, 5- or 6-membered heteroaryl, $C(O)R^{5E}$, $C(O)OR^{5E}$, $C(O)NR^{5E}R^{5F}$ or $NR^{5E}C(O)R^{5F}$; wherein $R^{5E}$ and $R^{5F}$ are each independently selected from hydrogen, (1-4C)alkyl or (1-4C)haloalkyl;
  - and wherein any alkyl, aryl, heterocyclyl or heteroaryl group present in a substituent group on $Z^5$ is optionally further substituted by halo, cyano, nitro, hydroxy, amino, (1-2C)alkoxy or (1-2C)alkyl;

(62) $R_5$ selected from hydrogen, halo, cyano, nitro, hydroxy or a group of the formula:

$$-X^5-Z^5$$

wherein
- $X^5$ is absent or $-N(R^{5C})-$, $-S(O)_2N(R^{5C})-$ or $-N(R^{5D})SO_2-$ wherein $R^{5C}$ is selected from hydrogen or (1-2C)alkyl; and
- $Z^5$ is hydrogen, (1-6C)alkyl, aryl, 5- or 6-membered heteroaryl or 5- or 6-membered heterocyclyl;
  - and wherein $Z^5$ is optionally further substituted by one or more substituent groups independently selected from halo, cyano, hydroxy, carboxy, amino, (1-2C)alkoxy, (1-2C)alkyl, (1-2C)haloalkyl, (1-2C)haloalkoxy, (1-2C)alkylsulphonyl, phenyl, $C(O)R^{5E}$, $C(O)OR^{5E}$, $C(O)NR^{5E}R^{5F}$ or $NR^{5E}C(O)R^{5F}$; wherein $R^{5E}$ and$R^{5F}$ are each independently selected from hydrogen, (1-2C)alkyl or (1-2C)haloalkyl;
  - and wherein any alkyl or phenyl group present in a substituent group on $Z^5$ is optionally further substituted by halo, cyano, hydroxy, amino, (1-2C)alkoxy or (1-2C)alkyl;

(63) $R_5$ is selected from halo or a group of the formula:

$$-X^5-Z^5$$

wherein
- $X^5$ is absent or $-N(R^{5C})-$, $-S(O)_2N(R^{5C})-$ or $-N(R^{5D})SO_2-$ wherein $R^{5C}$ is selected from hydrogen or (1-2C)alkyl; and
- $Z^5$ is hydrogen, (1-4C)alkyl, aryl, 5- or 6-membered heteroaryl or 5- or 6-membered heterocyclyl;
  - and wherein $Z^5$ is optionally further substituted by one or more substituent groups independently selected from halo, cyano, hydroxy, carboxy, amino, (1-2C)alkoxy, (1-2C)alkyl, (1-2C)haloalkyl, (1-2C)haloalkoxy, (1-2C)alkylsulphonyl, phenyl or $C(O)R^{5E}$; wherein $R^{5E}$ is selected from hydrogen, methyl or $CF_3$;
  - and wherein any phenyl group present in a substituent group on $Z^5$ is optionally further substituted by halo, cyano, hydroxy, amino, (1-2C) alkoxy or (1-2C)alkyl.

Suitably, a heteroaryl or heterocyclyl group as defined herein is a monocyclic or bicyclic heteroaryl or heterocyclyl group comprising one, two or three heteroatoms selected from N, O or S. More suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5-, 6- or 7-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

Suitably, $R_1$ is as defined in any one of paragraphs (1) to (10) above. Most suitably, $R_1$ is as defined in paragraph (10) above.

Suitably, $R_2$ is as defined in any one of paragraphs (11) to (25) above. More suitably, $R_2$ is as defined in any one of paragraphs (19) to (25) above. Most suitably $R_2$ is as defined in paragraph (25) above.

Suitably, $R_3$ is as defined in any one of paragraphs (26) to (39) above. More suitably, $R_3$ is as defined in any one of paragraphs (35) to (39) above. Most suitably, $R_3$ is as defined in paragraph (39) above.

Suitably, $X_1$ is as defined in any one of paragraphs (40) to (41) above. Most suitably, $X_1$ is as defined in paragraph (41) above.

Suitably, $R_4$ is as defined in any one of paragraphs (42) to (49) above. Most suitably, $R_4$ is as defined in paragraphs (49) above.

Suitably, $R_5$ is as defined in any one of paragraphs (50) to (63) above. Most suitably $R_5$ is as defined in paragraph (63) above.

In a particular embodiment of the compounds of Formula I, when $R_1$ and $R_4$ are hydrogen, $R_2$ is COOH and $R_5$ is hydrogen or methyl, $R_3$ is not phenyl, 3-methylphenyl or 3,5-dimethylphenyl.

In another particular embodiment, the compound of Formula I is not one of the following:
3,6,6-Trimethyl-4-oxo-4,5,6,7-tetrahydro-1H-indole-2-carboxylic acid;
5-Methyl-3-phenyl-1H-pyrrole-2-carboxylic acid;
3-Phenyl-1H-pyrrole-2-carboxylic acid;
3-(3'-Methylphenyl)-1H-pyrrole-2-carboxylic acid;
3-(3',5'-Dimethylphenyl)-1H-pyrrole-2-carboxylic acid; or
2,4-Dibromo-1H-imidazole-5-carboxylic acid.

In a particular group of compounds of the invention, $R_1$ is H, i.e. the compounds have the structural formula Ia (a sub-definition of formula I) shown below:

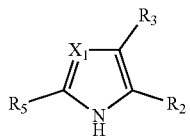

Formula Ia wherein, $R_2$, $R_3$, $X_1$ and $R_5$ each have any one of the meanings defined herein; or a pharmaceutically acceptable salt, hydrate and/or solvate thereof.

In an embodiment of the compounds of Formula Ia:
$R_2$ is as defined in any one of paragraphs (11) to (25) above;
$R_3$ is as defined in any one of paragraphs (26) to (39) above;
$X_1$ is as defined in any one of paragraphs (40) to (41) above; and
$R_5$ is as defined in any one of paragraphs (50) to (63) above.

In another embodiment of the compounds of Formula Ia:
$R_2$ is as defined in any paragraph (25) above;
$R_3$ is as defined in paragraph (39) above;
$X_1$ is as defined in paragraph (41) above; and
$R_5$ is as defined in paragraph (63) above.

In another group of compounds of the invention, $R_1$ is H, $X_1$ is C—$R_4$ and $R_4$ is as defined below, i.e. the compounds have the structural formula Ib (a sub-definition of formula I) shown below:

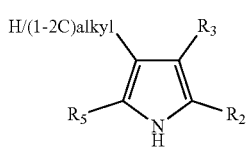

Formula Ib wherein, $R_2$, $R_3$ and $R_5$ each have any one of the meanings defined herein; or a pharmaceutically acceptable salt, hydrate and/or solvate thereof.

In an embodiment of the compounds of Formula Ib:
$R_2$ is as defined in any one of paragraphs (11) to (25) above;
$R_3$ is as defined in any one of paragraphs (26) to (39) above; and
$R_5$ is as defined in any one of paragraphs (50) to (63) above.

In another embodiment of the compounds of Formula Ib:
$R_2$ is as defined in any paragraph (25) above;
$R_3$ is as defined in paragraph (39) above; and
$R_5$ is as defined in paragraph (63) above.

In another group of compounds of the invention, $R_1$ is H, $R_2$ is COOH and $X_1$ is C—$R_4$, with $R_4$ being as defined below, i.e. the compounds have the structural formula Ic (a sub-definition of formula I) shown below:

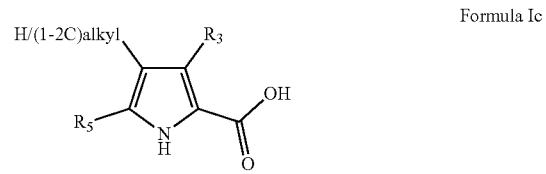

Formula Ic wherein, $R_3$ and $R_5$ each have any one of the meanings defined herein; or a pharmaceutically acceptable salt, hydrate and/or solvate thereof.

In an embodiment of the compounds of Formula Ic:
$R_3$ is as defined in any one of paragraphs (26) to (39) above; and
$R_5$ is as defined in any one of paragraphs (50) to (63) above.

In another embodiment of the compounds of Formula Ic:
$R_3$ is as defined in paragraph (39) above; and
$R_5$ is as defined in paragraph (63) above.

In another group of compounds of the invention, $X_1$ is C—$R_4$, and $R_4$ and $R_5$ are linked such that they form Ring A, as shown below, i.e. the compounds have the structural formula Id (a sub-definition of formula I) shown below:

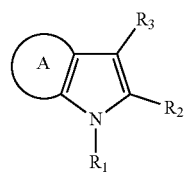

Formula Id wherein, $R_1$, $R_2$ and $R_3$ each have any one of the meanings defined herein; and Ring A is a 5 to 8-membered non-aromatic carbocyclic or heterocyclic ring, which is optionally substituted by one or more substituents selected from oxo, halo, cyano, nitro, hydroxy, carboxy, $NR^{5I}R^{5J}$, (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5J}$, $C(O)OR^{5J}$, $OC(O)R^{5J}$, $C(O)NR^{5I}R^{5J}$, $NR^{5I}C(O)R^{5J}$, $NR^{5I}S(O)_2R^{5J}$ and $S(O)_2NR^{5I}R^{5J}$, wherein $R^{5i}$ and $R^{5j}$ are each independently selected from hydrogen, (1-4C)alkyl, (1-4C)haloalkyl, (3-6C)cycloalkyl or (3-6C)cycloalkyl(1-2C)alkyl; or $R^{5I}$ and $R^{5J}$ can be linked such that, together with the nitrogen atom to which they are attached, they form a 4-7 membered heterocyclic ring;
or a pharmaceutically acceptable salt, hydrate and/or solvate thereof.

In an embodiment of the compounds of Formula Id:
$R_1$ is as defined in any one of paragraphs (1) to (10) above;
$R_2$ is as defined in any one of paragraphs (11) to (25) above;
$R_3$ is as defined in any one of paragraphs (26) to (39) above; and
Ring A is 5 to 8-membered non-aromatic carbocyclic or heterocyclic ring, which is optionally substituted by one or more substituents selected from oxo, halo, cyano, nitro, hydroxy, carboxy, $NR^{5i}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5i}R^{5J}$, $NR^{5i}C(O)R^{5J}$, $NR^{5i}S(O)_2R^{5J}$ and $S(O)_2NR^{5i}R^{5J}$, wherein $R^{5i}$ and $R^{5j}$ are each independently selected from hydrogen, (1-4C)alkyl or (3-6C)cycloalkyl.

In another embodiment of the compounds of Formula Id:
$R_1$ is as defined in paragraph (10) above;
$R_2$ is as defined in paragraph (25) above;
$R_3$ is as defined in paragraph (39) above; and
Ring A is 6-membered non-aromatic carbocyclic, which is optionally substituted by one or more substituents selected from oxo, halo, cyano, nitro, hydroxy, carboxy, amino, (1-2C)alkoxy, (1-2C)alkyl or (1-2C)haloalkyl.

In another group of compounds of the invention, $R_1$ is hydrogen, $R_2$ is COOH, $X_1$ is C—$R_4$, and $R_4$ and $R_5$ are linked such that they form Ring A, as shown below, i.e. the compounds have the structural formula Ie (a sub-definition of formula I) shown below:

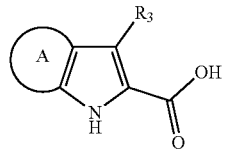

Formula Ie wherein, $R_1$, $R_2$ and $R_3$ each have any one of the meanings defined herein; and Ring A is a 5 to 8-membered non-aromatic carbocyclic or heterocyclic ring, which is optionally substituted by one or more substituents selected from oxo, halo, cyano, nitro, hydroxy, carboxy, $NR^{5i}R^{5J}$, (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5J}$, $C(O)OR^{5J}$, $OC(O)R^{5J}$, $C(O)NR^{5i}R^{5J}$, $NR^{5i}C(O)R^{5J}$, $NR^{5i}S(O)_2R^{5J}$ and $S(O)_2NR^{5i}R^{5J}$, wherein $R^{5i}$ and $R^{5j}$ are each independently selected from hydrogen, (1-4C)alkyl, (1-4C)haloalkyl, (3-6C)cycloalkyl or (3-6C)cycloalkyl(1-2C)alkyl; or $R^{5I}$ and $R^{5J}$ can be linked such that, together with the nitrogen atom to which they are attached, they form a 4-7 membered heterocyclic ring;
or a pharmaceutically acceptable salt, hydrate and/or solvate thereof.

In an embodiment of the compounds of Formula Ie:
$R_3$ is as defined in any one of paragraphs (26) to (39) above; and
Ring A is 6 to 8-membered non-aromatic carbocyclic or heterocyclic ring, which is optionally substituted by one or more substituents selected from oxo, halo, cyano, nitro, hydroxy, carboxy, $NR^{5i}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5i}R^{5J}$, $NR^{5i}C(O)R^{5J}$, $NR^{5i}S(O)_2R^{5J}$ and $S(O)_2NR^{5i}R^{5J}$, wherein $R^{5i}$ and $R^{5j}$ are each independently selected from hydrogen, (1-4C)alkyl or (3-6C)cycloalkyl.

In another embodiment of the compounds of Formula If:
$R_3$ is as defined in paragraph (39) above; and
Ring A is 6-membered non-aromatic carbocyclic, which is optionally substituted by one or more substituents selected from oxo, halo, cyano, nitro, hydroxy, carboxy, amino, (1-2C)alkoxy, (1-2C)alkyl or (1-2C)haloalkyl.

Particular compounds of the present invention include any of the compounds exemplified in the present application, or a pharmaceutically acceptable salt or solvate thereof, and, in particular, any of the following:

3-Phenyl-4,5,6,7-tetrahydro-1H-indole-2-carboxylic acid;

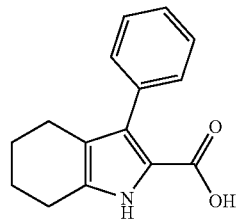 [SMILES: O=C(O)c1[nH]c2c(c1-c1ccccc1)CCCC2]

7-Methyl-3-phenyl-4,5,6,7-tetrahydro-1H-indole-2-carboxylicacid;

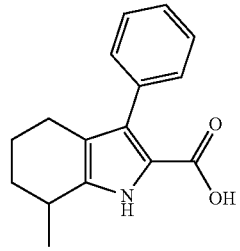 [SMILES: CC1CCCc2c1[nH]c(C(=O)O)c2-c1ccccc1]

7,7-Dimethyl-3-phenyl-4,5,6,7-tetrahydro-1H-indole-2-carboxylicacid;

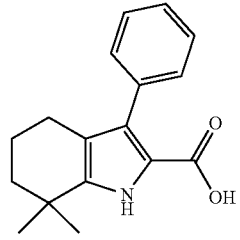 [SMILES: CC1(C)CCCc2c1[nH]c(C(=O)O)c2-c1ccccc1]

3,6,6-Trimethyl-4-oxo-4,5,6,7-tetrahydro-1H-indole-2-carboxylicacid;

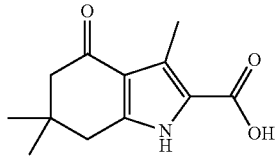 [SMILES: Cc1c(C(=O)O)[nH]c2c1C(=O)CC(C)(C)C2]

3,5,5-Trimethyl-4-oxo-4,5,6,7-tetrahydro-1H-indole-2-carboxylicacid;

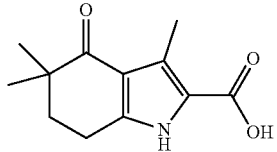 [SMILES: Cc1c(C(=O)O)[nH]c2c1C(=O)C(C)(C)CC2]

3-(3,5-Dichlorophenyl)-4-methyl-5-phenyl-1H-pyrrole-2-carboxylicacid;

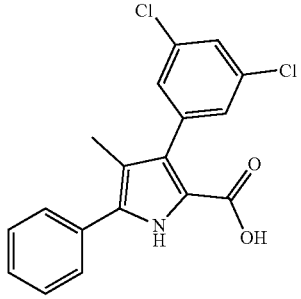 [SMILES: Cc1c(-c2ccccc2)[nH]c(C(=O)O)c1-c1cc(Cl)cc(Cl)c1]

5-(5-(3,5-Dichlorophenyl)furan-2-yl)-4-methyl-1H-pyrrole-2-carboxylicacid;

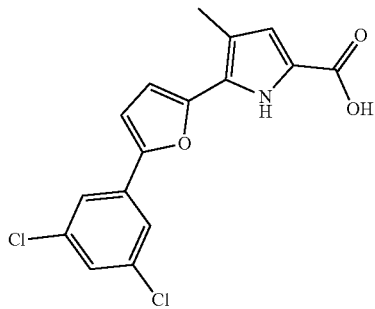 [SMILES: Cc1cc(C(=O)O)[nH]c1-c1ccc(-c2cc(Cl)cc(Cl)c2)o1]

3-(3-Chloro-4-((methysulfonyl)methyl)phenyl)-4-ethyl-5-(2-(trifluoromethyl)phenyl)-1H-pyrrole-2-carboxylicacid;

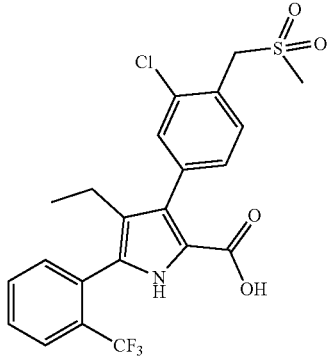 [SMILES: CCc1c(-c2ccccc2C(F)(F)F)[nH]c(C(=O)O)c1-c1ccc(CS(C)(=O)=O)c(Cl)c1]

3-(4-(Carboxymethyl)phenyl)-4-methyl-5-phenyl-1H-pyrrole-2-carboxylicacid

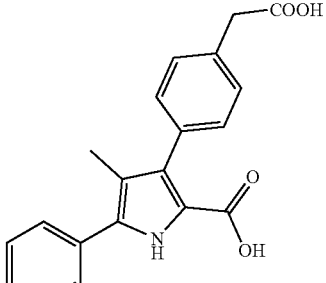

3-(4-Hydroxyphenyl)-4-methyl-5-phenyl-1H-pyrrole-2-carboxylic acid;

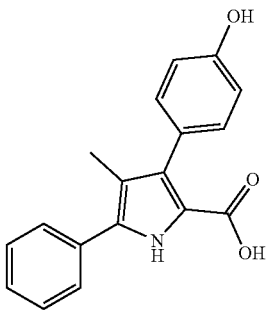 [SMILES: Cc1c(-c2ccccc2)[nH]c(C(=O)O)c1-c1ccc(O)cc1]

3-(4-((N,N-Dimethylsulfamoyl)methyl)phenyl)-4-methyl-5-phenyl-1H-pyrrole-2-carboxylic acid;

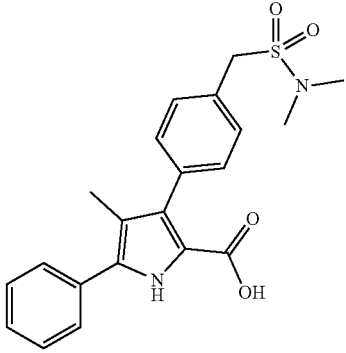 [SMILES: Cc1c(-c2ccccc2)[nH]c(C(=O)O)c1-c1ccc(CS(=O)(=O)N(C)C)cc1]

3-(3,5-Dichlorophenyl)-4-ethyl-5-phenyl-1H-pyrrole-2-carboxylic acid;

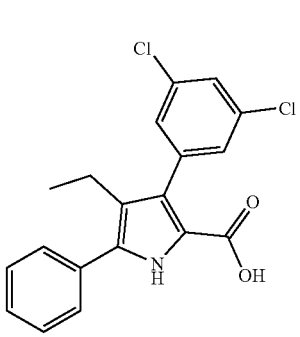 [SMILES: CCc1c(-c2ccccc2)[nH]c(C(=O)O)c1-c1cc(Cl)cc(Cl)c1]

4-Ethyl-3-(4-fluorophenyl)-5-phenyl-1H-pyrrole-2-carboxylicacid;

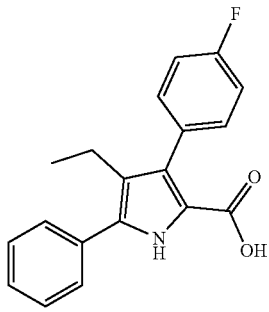 [SMILES: CCc1c(-c2ccccc2)[nH]c(C(=O)O)c1-c1ccc(F)cc1]

3-(3-Chloro-4-((methylsulfonyl)methyl)phenyl)-4-ethyl-5-phenyl-1H-pyrrole-2-carboxylicacid;

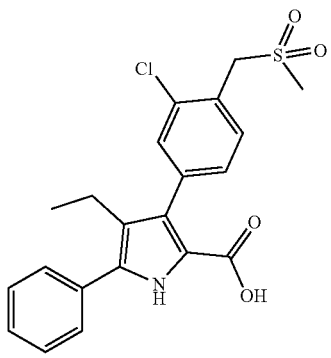 [SMILES: CCc1c(-c2ccccc2)[nH]c(C(=O)O)c1-c1ccc(CS(C)(=O)=O)c(Cl)c1]

3-(3,5-Dichlorophenyl)-5,5-dimethyl-4,5,6,7-tetrahydro-1H-4,6-methanoindole-2-carboxylic acid;

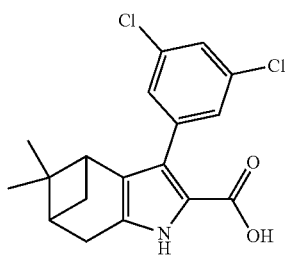

5-Methyl-3-phenyl-1H-pyrrole-2-carboxylic acid;

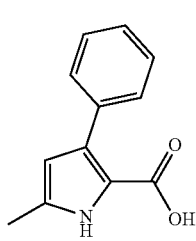

4-Methyl-3-phenyl-5-(2-(2,2,2-trifluoro-1-hydroxyethyl)phenyl)-1H-pyrrole-2-carboxylicacid;

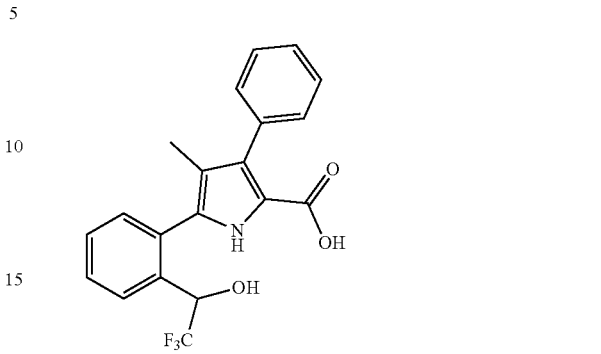

4-Methyl-3-phenyl-5-(3-(2,2,2-trifluoro-1-hydroxyethyl)phenyl)-1H-pyrrole-2-carboxylicacid;

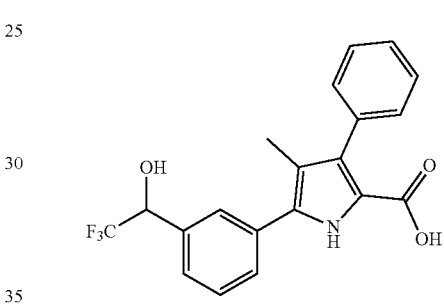

4-Methyl-5-nitro-3-phenyl-1H-pyrrole-2-carboxylicacid;

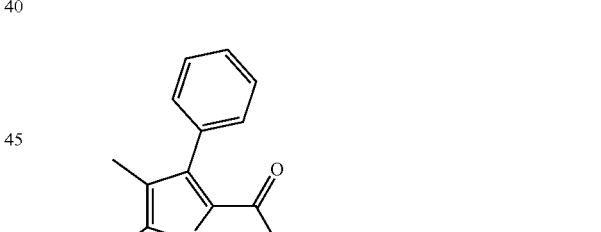

5-Acetyl-4-methyl-3-phenyl-1H-pyrrole-2-carboxylic acid;

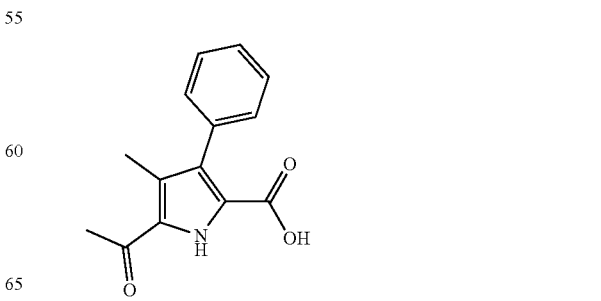

5-Acetyl-1,4-dimethyl-3-phenyl-1H-pyrrole-2-carboxylic acid;

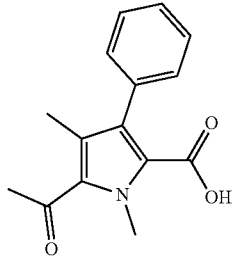 [SMILES: CC(=O)c1c(C)c(-c2ccccc2)c(C(=O)O)n1C]

3-(4-Fluorophenyl)-5-(phenylsulfonamido)-1H-pyrrole-2-carboxylic acid;

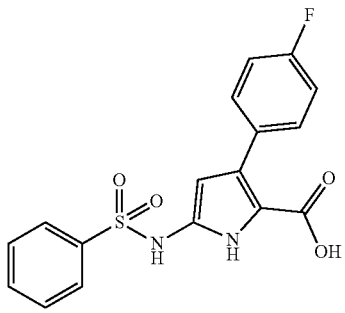 [SMILES: O=C(O)c1[nH]c(NS(=O)(=O)c2ccccc2)cc1-c1ccc(F)cc1]

3-Chloro-5-(2-phenoxyacetamido)-1H-pyrrole-2-carboxylicacid;

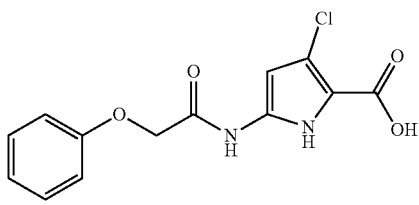 [SMILES: O=C(COc1ccccc1)Nc1cc(Cl)c(C(=O)O)[nH]1]

5-(2-Phenoxyacetamido)-3-phenyl-1H-pyrrole-2-carboxylicacid;

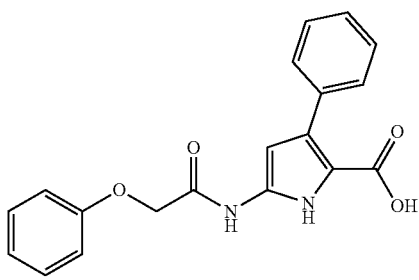 [SMILES: O=C(COc1ccccc1)Nc1cc(-c2ccccc2)c(C(=O)O)[nH]1]

3-Phenyl-1H-pyrrole-2-carboxylic acid;

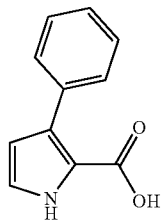 [SMILES: O=C(O)c1[nH]ccc1-c1ccccc1]

3-(3'-Methylphenyl)-1H-pyrrole-2-carboxylicacid;

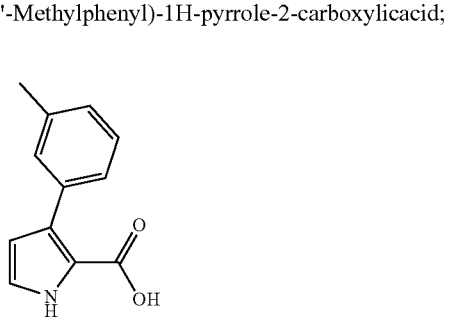

3-(3',5'-Dimethylphenyl)-1H-pyrrole-2-carboxylic acid;

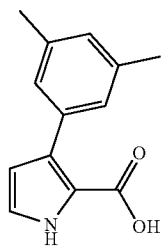 [SMILES: Cc1cc(C)cc(-c2cc[nH]c2C(=O)O)c1]

2,4-Dibromo-1H-imidazole-5-carboxylicacid;

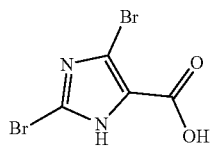

24-Bis(4-fluorophenyl)-1H-imidazole-5-carboxylic

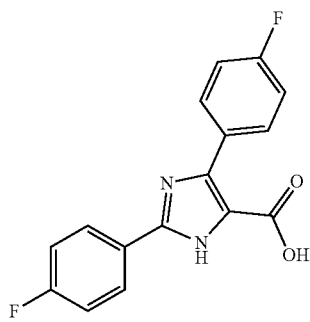 [SMILES: O=C(O)c1[nH]c(-c2ccc(F)cc2)nc1-c1ccc(F)cc1]

3-(3,5-Dichlorophenyl)-4-methyl-5-phenyl-1H-pyrrole-2-carboxamide;

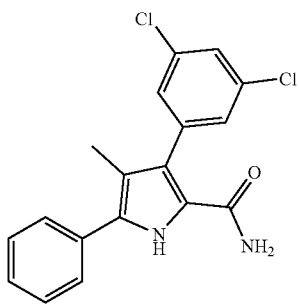

3-(3,5-Dichlorophenyl)-4-methyl-5-phenyl-1H-pyrrole-2-carbonitrile;

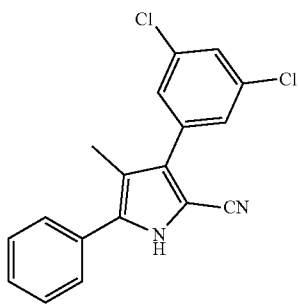 [SMILES: Cc1c(-c2ccccc2)[nH]c(C#N)c1-c1cc(Cl)cc(Cl)c1]

5-(3-(3,5-Dichlorophenyl)-4-methyl-5-phenyl-1H-pyrrol-2-yl)-1H-tetrazole;

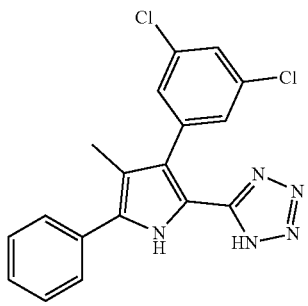 [SMILES: Cc1c(-c2ccccc2)[nH]c(-c2nnn[nH]2)c1-c1cc(Cl)cc(Cl)c1]

3-(4-Mercaptophenyl)-4-methyl-5-phenyl-1H-pyrrole-2-carboxylicacid;

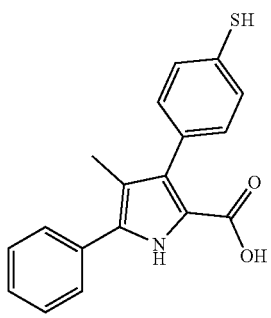

3-(4-Carboxyphenyl)-4-methyl-5-phenyl-1H-pyrrole-2-carboxylicacid;

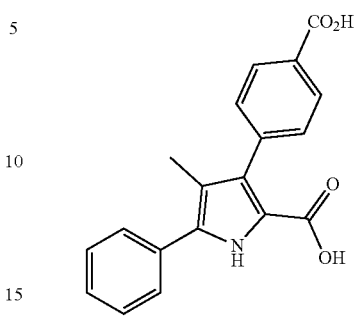

3-(3,5-Dichlorophenyl)-5-(thiophen-2-yl)-1H-pyrrole-2-carboxylicacid;

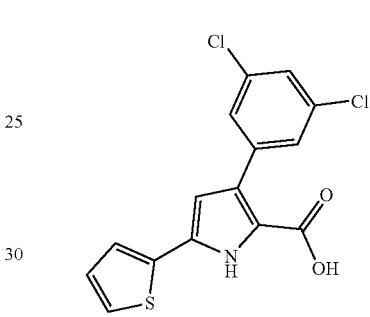

5-Cyclopropyl-3-(3,5-dichlorophenyl)-4-methyl-1H-pyrrole-2-carboxylicacid;

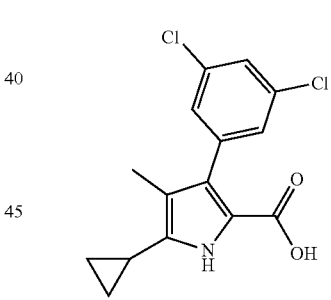

5-(Diisopropylamino)-3-(4-fluorophenyl)-1H-pyrrole-2-carboxylicacid;

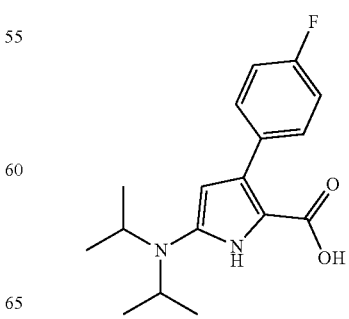

3-(3,5-Dichlorophenyl)-4-methyl-5-(1,2,3,6-tetrahydropyri-
din-4-yl)-1H-pyrrole-2-carboxylic acid;

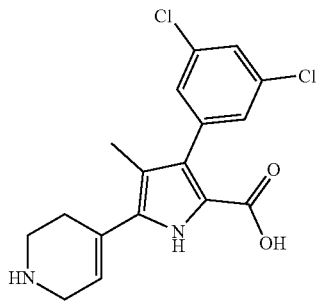 [SMILES: Cc1c(C2=CCNCC2)[nH]c(C(=O)O)c1-c1cc(Cl)cc(Cl)c1]

3-(3,5-Dichlorophenyl)-4-methyl-5-(3-(2,2,2-trifluoro-
acetyl)phenyl)-1H-pyrrole-2-carboxylic acid;

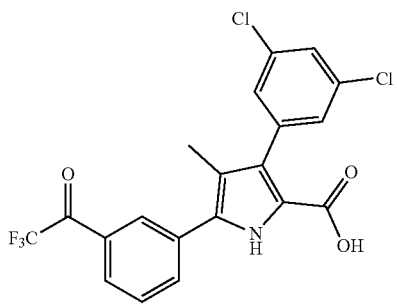 [SMILES: Cc1c(-c2cccc(C(=O)C(F)(F)F)c2)[nH]c(C(=O)O)c1-c1cc(Cl)cc(Cl)c1]

3-(3,5-Dichlorophenyl)-4-fluoro-5-phenyl-1H-pyrrole-2-
carboxylicacid;

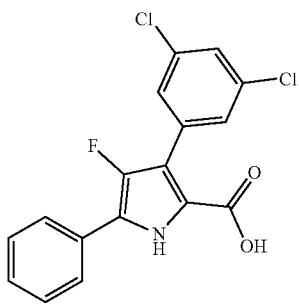

4-Methyl-3-phenyl-5-(3-(2,2,2-trifluoroacetyl)phenyl)-1H-
pyrrole-2-carboxylicacid;

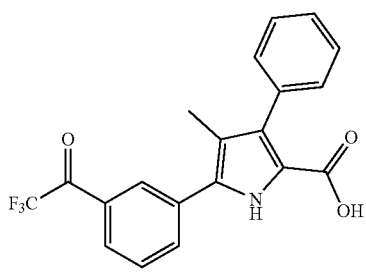 [SMILES: Cc1c(-c2cccc(C(=O)C(F)(F)F)c2)[nH]c(C(=O)O)c1-c1ccccc1]

3-(3,5-Dichlorophenyl)-4-methyl-5-(2-(2,2,2-trifluoro-
acetyl)phenyl)-1H-pyrrole-2-carboxylic acid;

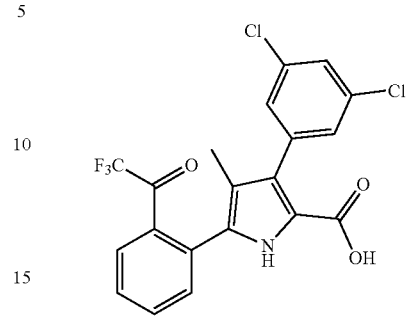

More particular compounds of the present invention include any of the compounds exemplified in the present application, or a pharmaceutically acceptable salt or solvate thereof, and, in particular, any of the following:

3-Phenyl-4,5,6,7-tetrahydro-1H-indole-2-carboxylic acid;

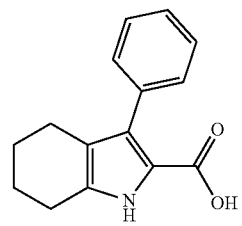 [SMILES: O=C(O)c1[nH]c2c(c1-c1ccccc1)CCCC2]

7-Methyl-3-phenyl-4,5,6,7-tetrahydro-1H-indole-2-carbox-
ylicacid;

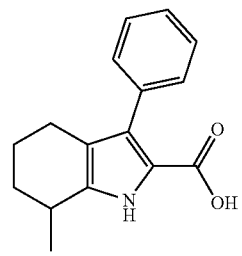 [SMILES: CC1CCCc2c1[nH]c(C(=O)O)c2-c1ccccc1]

7,7-Dimethyl-3-phenyl-4,5,6,7-tetrahydro-1H-indole-2-car-
boxylicacid;

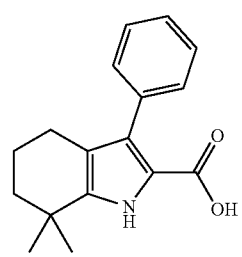 [SMILES: CC1(C)CCCc2c1[nH]c(C(=O)O)c2-c1ccccc1]

3,6,6-Trimethyl-4-oxo-4,5,6,7-tetrahydro-1H-indole-2-carboxylicacid;

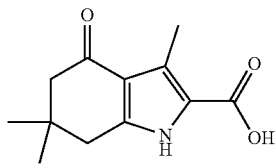 [SMILES: Cc1c(C(=O)O)[nH]c2c1C(=O)CC(C)(C)C2]

3,5,5-Trimethyl-4-oxo-4,5,6,7-tetrahydro-1H-indole-2-carboxylicacid;

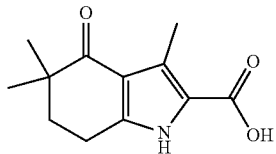 [SMILES: Cc1c(C(=O)O)[nH]c2c1C(=O)C(C)(C)CC2]

3-(3,5-Dichlorophenyl)-5,5-dimethyl-4,5,6,7-tetrahydro-1H-4,6-methanoindole-2-carboxylic acid;

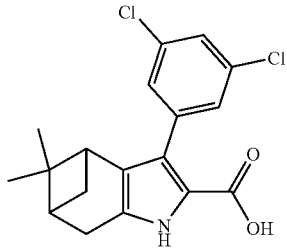 [SMILES: CC1(C)C2Cc3[nH]c(C(=O)O)c(-c4cc(Cl)cc(Cl)c4)c3C1C2]

3-(3,5-Dichlorophenyl)-4-methyl-5-phenyl-1H-pyrrole-2-carboxylicacid;

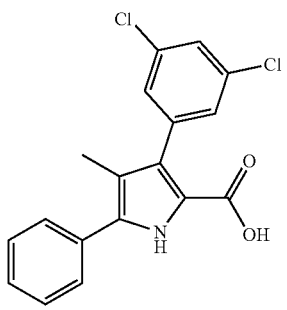 [SMILES: Cc1c(-c2ccccc2)[nH]c(C(=O)O)c1-c1cc(Cl)cc(Cl)c1]

5-(5-(3,5-Dichlorophenyl)furan-2-yl)-4-methyl-1H-pyrrole-2-carboxylicacid;

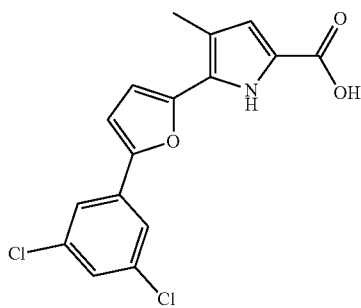 [SMILES: Cc1cc(C(=O)O)[nH]c1-c1ccc(-c2cc(Cl)cc(Cl)c2)o1]

3-(3-Chloro-4-((methysulfonyl)methyl)phenyl)-4-ethyl-5-(2-(trifluoromethyl)phenyl)-1H-pyrrole-2-carboxylicacid;

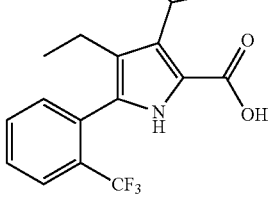

5-Methyl-3-phenyl-1H-pyrrole-2-carboxylic acid;

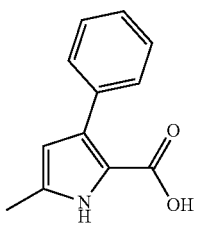

3-Phenyl-1H-pyrrole-2-carboxylic acid;

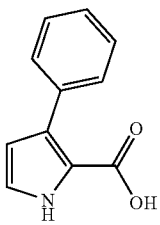 [SMILES: O=C(O)c1[nH]ccc1-c1ccccc1]

3-(3'-Methylphenyl)-1H-pyrrole-2-carboxylicacid;

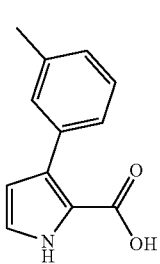

3-(3',5'-Dimethylphenyl)-1H-pyrrole-2-carboxylic acid;

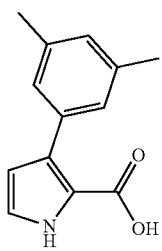

2,4-Dibromo-1H-imidazole-5-carboxylicacid;

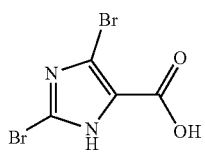

3-(3,5-Dichlorophenyl)-4-methyl-5-phenyl-1H-pyrrole-2-carboxamide;

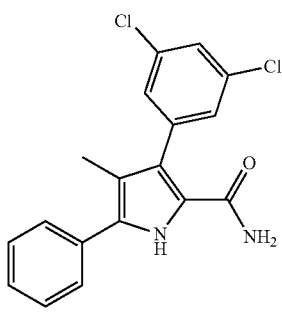 [SMILES: Cc1c(-c2ccccc2)[nH]c(C(N)=O)c1-c1cc(Cl)cc(Cl)c1]

3-(3,5-Dichlorophenyl)-4-methyl-5-phenyl-1H-pyrrole-2-carbonitrile;

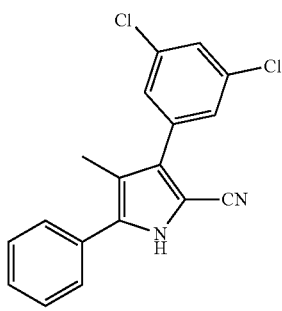 [SMILES: Cc1c(-c2ccccc2)[nH]c(C#N)c1-c1cc(Cl)cc(Cl)c1]

5-(3-(3,5-Dichlorophenyl)-4-methyl-5-phenyl-1H-pyrrol-2-yl)-1H-tetrazole;

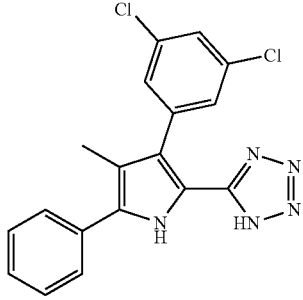 [SMILES: Cc1c(-c2ccccc2)[nH]c(-c2nnn[nH]2)c1-c1cc(Cl)cc(Cl)c1]

3-(3,5-Dichlorophenyl)-4-ethyl-5-phenyl-1H-pyrrole-2-carboxylic acid;

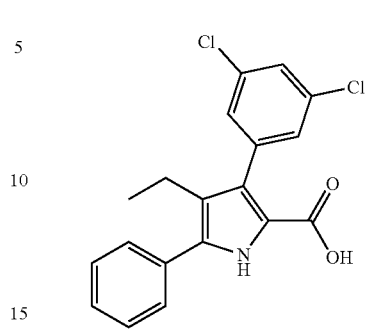

4-Ethyl-3-(4-fluorophenyl)-5-phenyl-1H-pyrrole-2-carboxylicacid;

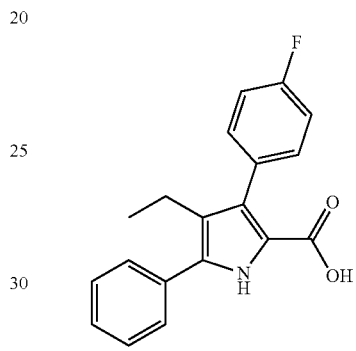

3-(3-Chloro-4-((methylsulfonyl)methyl)phenyl)-4-ethyl-5-phenyl-1H-pyrrole-2-carboxylicacid;

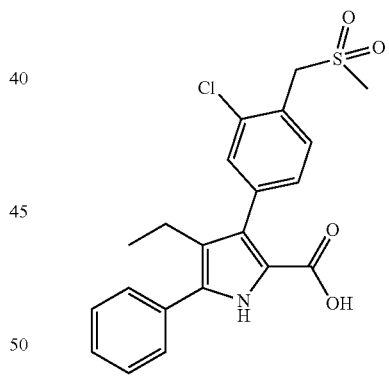

4-Methyl-3-phenyl-5-(3-(2,2,2-trifluoroacetyl)phenyl)-1H-pyrrole-2-carboxylicacid;

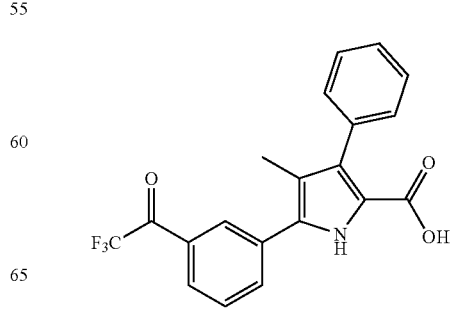

3-(3,5-Dichlorophenyl)-4-methyl-5-(2-(2,2-trifluoro-
acetyl)phenyl)-1H-pyrrole-2-carboxylic acid;

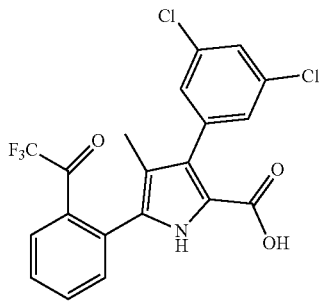 [SMILES: Cc1c(-c2ccccc2C(=O)C(F)(F)F)[nH]c(C(=O)O)c1-c1cc(Cl)cc(Cl)c1]

3-(3,5-Dichlorophenyl)-4-methyl-5-(3-(2,2-trifluoro-
acetyl)phenyl)-1H-pyrrole-2-carboxylic acid;

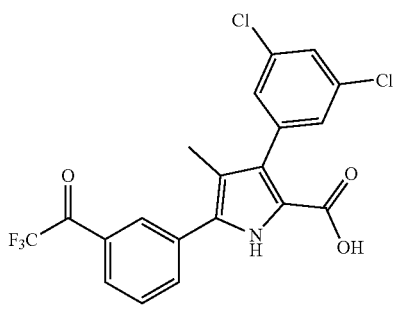 [SMILES: Cc1c(-c2cccc(C(=O)C(F)(F)F)c2)[nH]c(C(=O)O)c1-c1cc(Cl)cc(Cl)c1]

3-(3,5-Dichlorophenyl)-4-methyl-5-(1,2,3,6-tetrahydropyri-
din-4-yl)-1H-pyrrole-2-carboxylic acid;

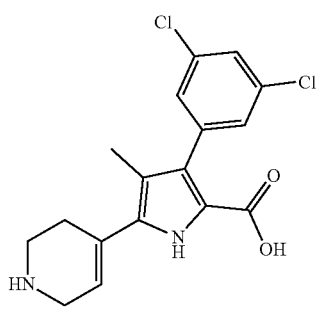 [SMILES: Cc1c(C2=CCNCC2)[nH]c(C(=O)O)c1-c1cc(Cl)cc(Cl)c1]

3-(3,5-Dichlorophenyl)-4-fluoro-5-phenyl-1H-pyrrole-2-
carboxylicacid;

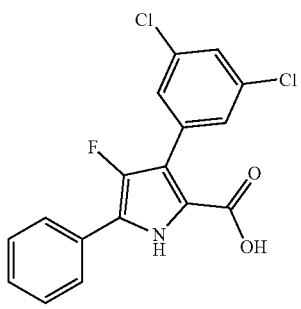

3-(3,5-Dichlorophenyl)-5-(thiophen-2-yl)-1H-pyrrole-2-
carboxylicacid;

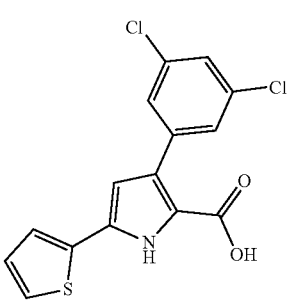 [SMILES: O=C(O)c1[nH]c(-c2cccs2)cc1-c1cc(Cl)cc(Cl)c1]

3-(4-Fluorophenyl)-5-(phenylsulfonamido)-1H-pyrrole-2-
carboxylic acid;

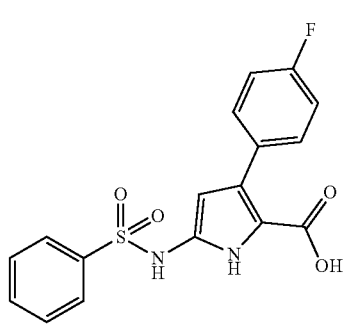 [SMILES: O=C(O)c1[nH]c(NS(=O)(=O)c2ccccc2)cc1-c1ccc(F)cc1]

5-(Diisopropylamino)-3-(4-fluorophenyl)-1H-pyrrole-2-
carboxylic acid;

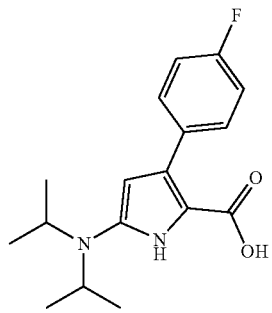 [SMILES: CC(C)N(c1cc(-c2ccc(F)cc2)c(C(=O)O)[nH]1)C(C)C]

3-(4-Hydroxyphenyl)-4-methyl-5-phenyl-1H-pyrrole-2-car-
boxylic acid;

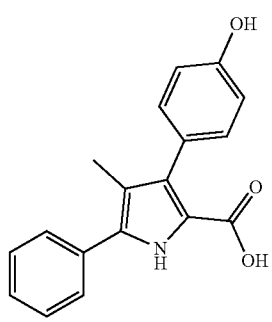 [SMILES: Cc1c(-c2ccccc2)[nH]c(C(=O)O)c1-c1ccc(O)cc1]

3-(4-Mercaptophenyl)-4-methyl-5-phenyl-1H-pyrrole-2-carboxylic acid;

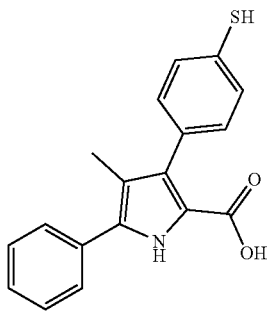

3-(4-Carboxyphenyl)-4-methyl-5-phenyl-1H-pyrrole-2-carboxylic acid; or

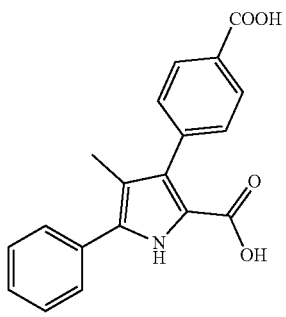 [SMILES: Cc1c(-c2ccccc2)[nH]c(C(=O)O)c1-c1ccc(C(=O)O)cc1]

2,4-Bis(4-fluorophenyl)-1H-imidazole-5-carboxylic

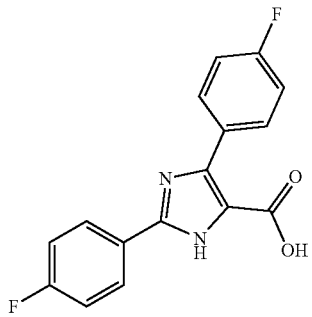 [SMILES: O=C(O)c1[nH]c(-c2ccc(F)cc2)nc1-c1ccc(F)cc1]

Further particular compounds of the present invention include any of the compounds exemplified in the present application, or a pharmaceutically acceptable salt or solvate thereof, and, in particular, any of the following:
3-Phenyl-4,5,6,7-tetrahydro-1H-indole-2-carboxylic acid;
7-Methyl-3-phenyl-4,5,6,7-tetrahydro-1H-indole-2-carboxylic acid;
7,7-Dimethyl-3-phenyl-4,5,6,7-tetrahydro-1H-indole-2-carboxylic acid;
3,5,5-Trimethyl-4-oxo-4,5,6,7-tetrahydro-1H-indole-2-carboxylic acid;
3-(3,5-Dichlorophenyl)-5,5-dimethyl-4,5,6,7-tetrahydro-1H-4,6-methanoindole-2-carboxylic acid;
3-(3,5-Dichlorophenyl)-4-methyl-5-phenyl-1H-pyrrole-2-carboxylic acid;
5-(5-(3,5-Dichlorophenyl)furan-2-yl)-4-methyl-1H-pyrrole-2-carboxylic acid;
3-(3-Chloro-4-((methysulfonyl)methyl)phenyl)-4-ethyl-5-(2-(trifluoromethyl)phenyl)-1H-pyrrole-2-carboxylic acid;
3-(3,5-Dichlorophenyl)-4-methyl-5-phenyl-1H-pyrrole-2-carboxamide;
3-(3,5-Dichlorophenyl)-4-methyl-5-phenyl-1H-pyrrole-2-carbonitrile;
5-(3-(3,5-Dichlorophenyl)-4-methyl-5-phenyl-1H-pyrrol-2-yl)-1H-tetrazole;
3-(3,5-Dichlorophenyl)-4-ethyl-5-phenyl-1H-pyrrole-2-carboxylic acid;
4-Ethyl-3-(4-fluorophenyl)-5-phenyl-1H-pyrrole-2-carboxylic acid;
3-(3-Chloro-4-((methylsulfonyl)methyl)phenyl)-4-ethyl-5-phenyl-1H-pyrrole-2-carboxylic acid;
4-Methyl-3-phenyl-5-(3-(2,2,2-trifluoroacetyl)phenyl)-1H-pyrrole-2-carboxylic acid;
3-(3,5-Dichlorophenyl)-4-methyl-5-(2-(2,2,2-trifluoroacetyl)phenyl)-1H-pyrrole-2-carboxylic acid;
3-(3,5-Dichlorophenyl)-4-methyl-5-(3-(2,2,2-trifluoroacetyl)phenyl)-1H-pyrrole-2-carboxylic acid:
3-(3,5-Dichlorophenyl)-4-methyl-5-(1,2,3,6-tetrahydropyridin-4-yl)-1H-pyrrole-2-carboxylic acid;
3-(3,5-Dichlorophenyl)-4-fluoro-5-phenyl-1H-pyrrole-2-carboxylic acid;
3-(3,5-Dichlorophenyl)-5-(thiophen-2-yl)-1H-pyrrole-2-carboxylic acid;
3-(4-Fluorophenyl)-5-(phenylsulfonamido)-1H-pyrrole-2-carboxylic acid;
5-(Diisopropylamino)-3-(4-fluorophenyl)-1H-pyrrole-2-carboxylic acid;
3-(4-Hydroxyphenyl)-4-methyl-5-phenyl-1H-pyrrole-2-carboxylic acid;
3-(4-Mercaptophenyl)-4-methyl-5-phenyl-1H-pyrrole-2-carboxylic acid;
3-(4-(Carboxymethyl)phenyl)-4-methyl-5-phenyl-1H-pyrrole-2-carboxylic acid;
3-(4-((N,N-Dimethylsulfamoyl)methyl)phenyl)-4-methyl-5-phenyl-1H-pyrrole-2-carboxylic acid;
5-Cyclopropyl-3-(3,5-dichlorophenyl)-4-methyl-1H-pyrrole-2-carboxylic acid;
4-Methyl-5-nitro-3-phenyl-1H-pyrrole-2-carboxylic acid;
5-Acetyl-4-methyl-3-phenyl-1H-pyrrole-2-carboxylic acid;
5-Acetyl-1,4-dimethyl-3-phenyl-1H-pyrrole-2-carboxylic acid;
4-Methyl-3-phenyl-5-(3-(2,2,2-trifluoro-1-hydroxyethyl)phenyl)-1H-pyrrole-2-carboxylic acid;
4-Methyl-3-phenyl-5-(2-(2,2,2-trifluoro-1-hydroxyethyl)phenyl)-1H-pyrrole-2-carboxylic acid;
3-Chloro-5-(2-phenoxyacetamido)-1H-pyrrole-2-carboxylic acid;
5-(2-Phenoxyacetamido)-3-phenyl-1H-pyrrole-2-carboxylic acid;
3-(4-Carboxyphenyl)-4-methyl-5-phenyl-1H-pyrrole-2-carboxylic acid; or
2,4-Bis(4-fluorophenyl)-1H-imidazole-5-carboxylic.

Further particular compounds of the present invention include any of the compounds exemplified in the present application, or a pharmaceutically acceptable salt or solvate thereof, and, in particular, any of the following:
3-Phenyl-4,5,6,7-tetrahydro-1H-indole-2-carboxylic acid;
7-Methyl-3-phenyl-4,5,6,7-tetrahydro-1H-indole-2-carboxylic acid;
7,7-Dimethyl-3-phenyl-4,5,6,7-tetrahydro-1H-indole-2-carboxylic acid;
3,5,5-Trimethyl-4-oxo-4,5,6,7-tetrahydro-1H-indole-2-carboxylic acid;

3-(3,5-Dichlorophenyl)-5,5-dimethyl-4,5,6,7-tetrahydro-1H-4,6-methanoindole-2-carboxylic acid;
3-(3,5-Dichlorophenyl)-4-methyl-5-phenyl-1H-pyrrole-2-carboxylic acid;
5-(5-(3,5-Dichlorophenyl)furan-2-yl)-4-methyl-1H-pyrrole-2-carboxylic acid;
3-(3-Chloro-4-((methysufonyl)methyl)phenyl)-4-ethyl-5-(2-(trifluoromethyl)phenyl)-1H-pyrrole-2-carboxylic acid;
3-(3,5-Dichlorophenyl)-4-methyl-5-phenyl-1H-pyrrole-2-carboxamide;
3-(3,5-Dichlorophenyl)-4-methyl-5-phenyl-1H-pyrrole-2-carbonitrile;
5-(3-(3,5-Dichlorophenyl)-4-methyl-5-phenyl-1H-pyrrol-2-yl)-1H-tetrazole;
3-(3,5-Dichlorophenyl)-4-ethyl-5-phenyl-1H-pyrrole-2-carboxylic acid;
4-Ethyl-3-(4-fluorophenyl)-5-phenyl-1H-pyrrole-2-carboxylic acid;
3-(3-Chloro-4-((methylsulfonyl)methyl)phenyl)-4-ethyl-5-phenyl-1H-pyrrole-2-carboxylic acid;
4-Methyl-3-phenyl-5-(3-(2,2,2-trifluoroacetyl)phenyl)-1H-pyrrole-2-carboxylic acid;
3-(3,5-Dichlorophenyl)-4-methyl-5-(2-(2,2,2-trifluoroacetyl)phenyl)-1H-pyrrole-2-carboxylic acid;
3-(3,5-Dichlorophenyl)-4-methyl-5-(3-(2,2,2-trifluoroacetyl)phenyl)-1H-pyrrole-2-carboxylic acid;
3-(3,5-Dichlorophenyl)-4-methyl-5-(1,2,3,6-tetrahydropyridin-4-yl)-1H-pyrrole-2-carboxylic acid;
3-(3,5-Dichlorophenyl)-4-fluoro-5-phenyl-1H-pyrrole-2-carboxylic acid;
3-(3,5-Dichlorophenyl)-5-(thiophen-2-yl)-1H-pyrrole-2-carboxylic acid;
3-(4-Fluorophenyl)-5-(phenylsulfonamido)-1H-pyrrole-2-carboxylic acid;
5-(Diisopropylamino)-3-(4-fluorophenyl)-1H-pyrrole-2-carboxylic acid;
3-(4-Hydroxyphenyl)-4-methyl-5-phenyl-1H-pyrrole-2-carboxylic acid;
3-(4-Mercaptophenyl)-4-methyl-5-phenyl-1H-pyrrole-2-carboxylic acid;
3-(4-Carboxyphenyl)-4-methyl-5-phenyl-1H-pyrrole-2-carboxylic acid; or
2,4-Bis(4-fluorophenyl)-1H-imidazole-5-carboxylic.

Particular compounds of the present invention include any of the compounds exemplified in the present application, or a pharmaceutically acceptable salt or solvate thereof, and, in particular, any of the following:
3-Phenyl-4,5,6,7-tetrahydro-1H-indole-2-carboxylic acid
7-Methyl-3-phenyl-4,5,6,7-tetrahydro-1H-indole-2-carboxylic acid;
7,7-Dimethyl-3-phenyl-4,5,6,7-tetrahydro-1H-indole-2-carboxylic acid;
3,5,5-Trimethyl-4-oxo-4,5,6,7-tetrahydro-1H-indole-2-carboxylic acid; or
3-(3,5-Dichlorophenyl)-5,5-dimethyl-4,5,6,7-tetrahydro-1H-4,6-methanoindole-2-carboxylic acid.

Particular compounds of the present invention include any of the compounds exemplified in the present application, or a pharmaceutically acceptable salt or solvate thereof, and, in particular, any of the following:
3-(3,5-Dichlorophenyl)-4-methyl-5-phenyl-1H-pyrrole-2-carboxylic acid;
5-(5-(3,5-Dichlorophenyl)furan-2-yl)-4-methyl-1H-pyrrole-2-carboxylic acid;
3-(3-Chloro-4-((methysufonyl)methyl)phenyl)-4-ethyl-5-(2-(trifluoromethyl)phenyl)-1H-pyrrole-2-carboxylic acid;
3-(3,5-Dichlorophenyl)-4-methyl-5-phenyl-1H-pyrrole-2-carboxamide;
3-(3,5-Dichlorophenyl)-4-methyl-5-phenyl-1H-pyrrole-2-carbonitrile;
5-(3-(3,5-Dichlorophenyl)-4-methyl-5-phenyl-1H-pyrrol-2-yl)-1H-tetrazole;
3-(3,5-Dichlorophenyl)-4-ethyl-5-phenyl-1H-pyrrole-2-carboxylic acid;
4-Ethyl-3-(4-fluorophenyl)-5-phenyl-1H-pyrrole-2-carboxylic acid;
3-(3-Chloro-4-((methylsulfonyl)methyl)phenyl)-4-ethyl-5-phenyl-1H-pyrrole-2-carboxylic acid;
4-Methyl-3-phenyl-5-(3-(2,2,2-trifluoroacetyl)phenyl)-1H-pyrrole-2-carboxylic acid;
3-(3,5-Dichlorophenyl)-4-methyl-5-(2-(2,2,2-trifluoroacetyl)phenyl)-1H-pyrrole-2-carboxylic acid;
3-(3,5-Dichlorophenyl)-4-methyl-5-(3-(2,2,2-trifluoroacetyl)phenyl)-1H-pyrrole-2-carboxylic acid;
3-(3,5-Dichlorophenyl)-4-methyl-5-(1,2,3,6-tetrahydropyridin-4-yl)-1H-pyrrole-2-carboxylic acid;
3-(3,5-Dichlorophenyl)-4-fluoro-5-phenyl-1H-pyrrole-2-carboxylic acid;
3-(3,5-Dichlorophenyl)-5-(thiophen-2-yl)-1H-pyrrole-2-carboxylic acid;
3-(4-Fluorophenyl)-5-(phenylsulfonamido)-1H-pyrrole-2-carboxylic acid;
5-(Diisopropylamino)-3-(4-fluorophenyl)-1H-pyrrole-2-carboxylic acid;
3-(4-Hydroxyphenyl)-4-methyl-5-phenyl-1H-pyrrole-2-carboxylic acid
3-(4-Mercaptophenyl)-4-methyl-5-phenyl-1H-pyrrole-2-carboxylic acid;
3-(4-(Carboxymethyl)phenyl)-4-methyl-5-phenyl-1H-pyrrole-2-carboxylic acid;
3-(4-((N,N-Dimethylsulfamoyl)methyl)phenyl)-4-methyl-5-phenyl-1H-pyrrole-2-carboxylic acid;
5-Cyclopropyl-3-(3,5-dichlorophenyl)-4-methyl-1H-pyrrole-2-carboxylic acid;
4-Methyl-5-nitro-3-phenyl-1H-pyrrole-2-carboxylic acid;
5-Acetyl-4-methyl-3-phenyl-1H-pyrrole-2-carboxylic acid;
5-Acetyl-1,4-dimethyl-3-phenyl-1H-pyrrole-2-carboxylic acid;
4-Methyl-3-phenyl-5-(3-(2,2,2-trifluoro-1-hydroxyethyl)phenyl)-1H-pyrrole-2-carboxylic acid;
4-Methyl-3-phenyl-5-(2-(2,2,2-trifluoro-1-hydroxyethyl)phenyl)-1H-pyrrole-2-carboxylic acid;
3-Chloro-5-(2-phenoxyacetamido)-1H-pyrrole-2-carboxylic acid;
5-(2-Phenoxyacetamido)-3-phenyl-1H-pyrrole-2-carboxylic acid;
3-(4-Carboxyphenyl)-4-methyl-5-phenyl-1H-pyrrole-2-carboxylic acid; or
2,4-Bis(4-fluorophenyl)-1H-imidazole-5-carboxylic.

Further particular compounds of the present invention include any of the compounds exemplified in the present application, or a pharmaceutically acceptable salt or solvate thereof, and, in particular, any of the following:
3-(3,5-Dichlorophenyl)-4-methyl-5-phenyl-1H-pyrrole-2-carboxylic acid;
5-(5-(3,5-Dichlorophenyl)furan-2-yl)-4-methyl-1H-pyrrole-2-carboxylic acid;
3-(3-Chloro-4-((methysulfonyl)methyl)phenyl)-4-ethyl-5-(2-(trifluoromethyl)phenyl)-1H-pyrrole-2-carboxylic acid;

3-(3,5-Dichlorophenyl)-4-methyl-5-phenyl-1H-pyrrole-2-carboxamide;
3-(3,5-Dichlorophenyl)-4-methyl-5-phenyl-1H-pyrrole-2-carbonitrile;
5-(3-(3,5-Dichlorophenyl)-4-methyl-5-phenyl-1H-pyrrol-2-yl)-1H-tetrazole;
3-(3,5-Dichlorophenyl)-4-ethyl-5-phenyl-1H-pyrrole-2-carboxylic acid;
4-Ethyl-3-(4-fluorophenyl)-5-phenyl-1H-pyrrole-2-carboxylic acid;
3-(3-Chloro-4-((methylsulfonyl)methyl)phenyl)-4-ethyl-5-phenyl-1H-pyrrole-2-carboxylic acid;
4-Methyl-3-phenyl-5-(3-(2,2,2-trifluoroacetyl)phenyl)-1H-pyrrole-2-carboxylic acid;
3-(3,5-Dichlorophenyl)-4-methyl-5-(2-(2,2,2-trifluoroacetyl)phenyl)-1H-pyrrole-2-carboxylic acid:
3-(3,5-Dichlorophenyl)-4-methyl-5-(3-(2,2,2-trifluoroacetyl)phenyl)-1H-pyrrole-2-carboxylic acid;
3-(3,5-Dichlorophenyl)-4-methyl-5-(1,2,3,6-tetrahydropyridin-4-yl)-1H-pyrrole-2-carboxylic acid;
3-(3,5-Dichlorophenyl)-4-fluoro-5-phenyl-1H-pyrrole-2-carboxylic acid;
3-(3,5-Dichlorophenyl)-5-(thiophen-2-yl)-1H-pyrrole-2-carboxylic acid;
3-(4-Fluorophenyl)-5-(phenylsulfonamido)-1H-pyrrole-2-carboxylic acid;
5-(Diisopropylamino)-3-(4-fluorophenyl)-1H-pyrrole-2-carboxylic acid;
3-(4-Hydroxyphenyl)-4-methyl-5-phenyl-1H-pyrrole-2-carboxylic acid;
3-(4-Mercaptophenyl)-4-methyl-5-phenyl-1H-pyrrole-2-carboxylic acid;
3-(4-Carboxyphenyl)-4-methyl-5-phenyl-1H-pyrrole-2-carboxylic acid; or
2,4-Bis(4-fluorophenyl)-1H-imidazole-5-carboxylic.

The various functional groups and substituents making up the compounds of the Formula I (or sub-formulae Ia to Ie) are typically chosen such that the molecular weight of the compound of the formula I does not exceed 1000. More usually, the molecular weight of the compound will be less than 900, for example less than 800, or less than 700, or less than 650, or less than 600. More preferably, the molecular weight is less than 550 and, for example, is 500 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn-Ingold-Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^{1}$H, $^{2}$H(D), and $^{3}$H (T); C may be in any isotopic form, including $^{12}$C, $^{13}$C, and $^{14}$C; N may be in any isotopic form, including $^{7}$N and $^{8}$N (i.e. nitrogen-14 and nitrogen-15); and O may be in any isotopic form, including $^{16}$O and $^{18}$O; and the like.

It is also to be understood that certain compounds of the Formula I (or sub-formulae Ia to Ie) may exist in solvated as well as unsolvated forms such as, for example, hydrated forms. It is to be understood that the invention encompasses all such solvated forms that possess antiproliferative activity.

It is also to be understood that certain compounds of the Formula I (or sub-formulae Ia to Ie) may exhibit polymorphism, and that the invention encompasses all such forms that possess antiproliferative activity.

Compounds of the Formula I (or sub-formulae Ia to Ie) may exist in a number of different tautomeric forms and references to compounds of the formula I include all such forms. For the avoidance of doubt, where a compound can exist in one of several tautomeric forms, and only one is specifically described or shown, all others are nevertheless embraced by Formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

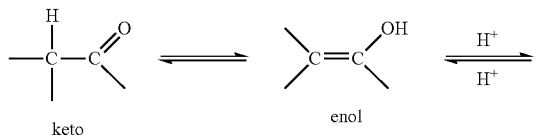

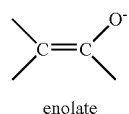
enolate

Compounds of the Formula I (or sub-formulae Ia to Ie) containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of Formula I (or sub-formulae Ia to Ie) may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I (or sub-formulae Ia to Ie) and in-vivo cleavable amide derivatives that may be formed at a carboxy group or an amino group in a compound of the Formula I (or sub-formulae Ia to Ie).

Accordingly, the present invention includes those compounds of the Formula I (or sub-formulae Ia to Ie) as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the Formula I (or sub-formulae Ia to Ie) may be a synthetically-produced compound or a metabolically-produced compound.

A suitable pharmaceutically acceptable pro-drug of a compound of the Formula I (or sub-formulae Ia to Ie) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I (or sub-formulae Ia to Ie) that possesses a carboxy group is, for example, an in vivo cleavable ester thereof. An in vivo cleavable ester of a compound of the Formula I (or sub-formulae Ia to Ie) containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the Formula I (or sub-formulae Ia to Ie) that possesses a hydroxy group is, for example, an in vivo cleavable ester or ether thereof. An in vivo cleavable ester or ether of a compound of the Formula I (or sub-formulae Ia to Ie) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-6}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I (or sub-formulae Ia to Ie) that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the Formula I (or sub-formulae Ia to Ie) that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I (or sub-formulae Ia to Ie) may be exerted in part by one or more metabolites that are formed within the human or animal body after administration of a compound of the Formula I (or sub-formulae Ia to Ie). As stated hereinbefore, the in vivo effects of a compound of the Formula I (or sub-formulae Ia to Ie) may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of Formula I (or sub-formulae Ia to Ie) will vary depending on the nature of $X_1$, $R_1$, $R_2$, $R_3$, $R_4$, $R_5$ and any substituent groups associated therewith. Suitable processes for their preparation are described further in the accompanying Examples.

Once a compound of Formula I (or sub-formulae Ia to Ie) has been synthesised by any one of the processes defined herein, the processes may then further comprise the additional steps of:
(i) removing any protecting groups present;
(ii) converting the compound Formula I into another compound of Formula I;
(iii) forming a pharmaceutically acceptable salt, hydrate or solvate thereof; and/or
(iv) forming a prodrug thereof.

An example of (ii) above is when a compound of Formula I is synthesised and then one or more of the groups $R_1$, $R_2$, $R_3$, $R_4$ and $R_5$ may be further reacted to change the nature of the group and provide an alternative compound of Formula I. For example, the compound can be reacted to covert $R_1$ into a substituent group other than hydrogen.

The resultant compounds of formula I can be isolated and purified using techniques well known in the art.

Biological Activity

The enzyme and in-vitro cell-based assays described in accompanying Example section, or elsewhere in the literature, may be used to measure the pharmacological effects of the compounds of the present invention.

Although the pharmacological properties of the compounds of formula I vary with structural change, as expected, the compounds of the invention were found to be active in these enzyme assays.

The compounds of the invention demonstrate a $pIC_{50}$ of 4 or more in the enzyme assays described herein, with preferred compounds of the invention demonstrating an $pIC_{50}$ of 4.5 or more and the most preferred compounds of the invention demonstrating an $pIC_{50}$ of 5 or more.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier. For example, solid oral forms may contain, together with the active compound, diluents, such as, for example, lactose, dextrose, saccharose, cellulose, corn starch or potato starch; lubricants, such as, for example, silica, talc, stearic acid, magnesium or calcium stearate, and/or polyethylene glycols; binding agents; such as, for example, starches, arabic gums, gelatin, methylcellulose, carboxymethycellulose or polyvinyl pyrrolidone; disaggregating agents, such as, for example, starch, alginic acid, alginates or sodium starch glycolate; effervescing mixtures; dyestuffs; sweeteners; wetting agents, such as, for example, lecithin, polysorbates, laurylsulphates; and, in general, non toxic and pharmacologically inactive substances used in pharmaceutical formulations. Such pharmaceutical compositions may be manufactured in by conventional methods known in the art, such as, for example, by mixing, granulating, tableting, sugar coating, or film coating processes.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Suitably, oral or parenteral administration is preferred. Most suitably, oral administration is preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the condition, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the present invention are inhibitors of metallo-beta-lactamases (MBLs). Many bacteria have developed resistance to β-lactam antibacterials (BLAs) and one of the main resistance mechanisms is the hydrolysis of BLAs by MBLs. Thus, the inhibition of bacterial MBLs by the compounds of the present invention can significantly enhance the activity of BLAs, when administered with a compound of the present invention.

The present invention provides compounds that function as inhibitors of metallo-beta-lactamases.

The present invention therefore provides a method of inhibiting bacterial metallo-beta-lactamase activity in vitro or in vivo, said method comprising contacting a cell with an effective amount of a compound, or a pharmaceutically acceptable salt, hydrate or solvate thereof, or a pharmaceutical composition as defined herein.

The present invention also provides a method for the prevention or treatment of bacterial infection in a patient in need of such treatment, said method comprising administering to said patient a therapeutically effective amount of a compound, or a pharmaceutically acceptable salt, hydrate or solvate thereof, or a pharmaceutical composition as defined herein, in combination with a suitable antibacterial agent.

In a preferred embodiment, the antibacterial agent is a β-lactam antibacterial agent, or analogue thereof. Non limiting examples of suitable β-lactam antibacterial agents include carbapenems (e.g. meropenem, faropenem, imipenem, ertapenem, doripenem, panipenem/betamipron and biapenem as well as razupenem, tebipenem, lenapenem and tomopenem), ureidopenicillins (e.g. piperacillin), carbacephems (e.g. loracarbef) and cephalosporins (e.g. cefpodoxime, ceftazidime, cefotaxime, ceftriaxone, ceftobiprole, and ceftaroline). Specific examples of suitable R-lactam antibacterial agents include, for example, temocillin, piperacillin, cefpodoxime, ceftazidime, cefotaxime, ceftriaxone, meropenem, faropenem, imipenem, loracarbef, ceftobiprole and ceftaroline.

The present invention also provides a method of inhibiting bacterial infection, in vitro or in vivo, said method comprising contacting a cell with an effective amount of a compound, or a pharmaceutically acceptable salt, hydrate or solvate thereof, as defined herein, in combination with a suitable antibacterial agent.

The present invention also provides a compound, or a pharmaceutically acceptable salt, hydrate or solvate thereof, or a pharmaceutical composition as defined herein for use in therapy.

The present invention also provides a compound, or a pharmaceutically acceptable salt, hydrate or solvate thereof, or a pharmaceutical composition as defined herein for use in the treatment of a bacterial infection. In one embodiment, the treatment may be prophylactic (i.e. intended to prevent disease).

The present invention provides a compound, or a pharmaceutically acceptable salt, hydrate or solvate thereof, as defined herein for use in the inhibition of metallo-beta-lactamase activity.

Furthermore, the present invention provides a compound, or a pharmaceutically acceptable salt, hydrate or solvate thereof, as defined herein for use in the treatment of a disease or disorder in which metallo-beta-lactamase activity is implicated.

The present invention also provides a kit of parts comprising a compound, or a pharmaceutically acceptable salt, hydrate or solvate thereof, or a pharmaceutical composition as defined herein, and a BLA and/or a BLA linked to a formula (I) compound.

The term "bacterial infection" will be understood to refer to the invasion of bodily tissue by any pathogenic microorganisms that proliferate, resulting in tissue injury that can progress to disease. Suitably, the pathogenic microorganism is a bacteria.

The bacterial infection may be caused by Gram-negative or Gram-positive bacteria.

For example, the bacterial infection may be caused by bacteria from one or more of the following families; *Clostridium, Pseudomonas, Escherichia, Klebsiella, Enterococcus, Enterobacter, Serratia, Stenotrophomonas, Aeromonas, Morganella, Yersinia, Salmonella, Proteus, Pasteurella, Haemophilus, Citrobacter, Burkholderia, Brucella, Moraxella, Mycobacterium, Streptococcus* or *Staphylococcus*. Particular examples include *Clostridium, Pseudomonas, Escherichia, Klebsiella, Enterococcus, Enterobacter, Streptococcus* and *Staphylococcus*. The bacterial infection may, for example, be caused by one or more bacteria selected from *Moraxella catarrhalis, Brucella abortus, Burkholderia cepacia, Citrobacter species, Escherichia coli, Haemophilus* Pneumonia, *Klebsiella Pneumonia, Pasteurella multocida, Proteus mirabilis, Salmonella typhimurium, Clostridium difficile, Yersinia enterocolitica Mycobacterium tuberculosis, Staphylococcus aureus*, group B streptococci, *Streptococcus* Pneumonia, and *Streptococcus pyogenes*, e.g. from *E. coli* and *K. pneumoniae*.

It will be understood by a person skilled in the art that the patient in need thereof is suitably a human, but may also include, but is not limited to, primates (e.g. monkeys), commercially farmed animals (e.g. horses, cows, sheep or pigs) and domestic pets (e.g. dogs, cats, guinea pigs, rabbits, hamsters or gerbils). Thus the patient in need thereof may be any mammal that is capable of being infected by a bacterium.

Routes of Administration

The compounds of the present invention, or pharmaceutical compositions comprising these compounds, may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Diagnostic Uses

The compounds of the present invention, or pharmaceutical compositions comprising these compounds in combination with a suitable antibacterial agent, may also be used in methods for the detection of metallo-beta-lactamases. It will be appreciated that the compounds of formula (I) may be modified to enable various types of assays known is the literature, such as those using spectroscopic such as fluorescence or luminescence based methods. Thus, in one variation a sample containing bacteria which is suspected of expressing MBLs can be cultured (a) in the presence of a beta-lactam antibiotic agent; and (b) in the presence of the antibiotic combination of the invention. If the bacteria are seen to grow under conditions (a), this suggests that a beta-lactamase, able to hydrolyse the antibiotic agent, is causing resistance of the bacteria to the antibiotic agent. However, if the bacteria do not grow under condition (b), i.e. in the presence of compound of the present invention and a suitable antibacterial agent, then the beta-lactamases present have been inhibited. Such a result suggests that the beta-lactamases are metallo-beta-lactamases. The method can be used to determine whether bacteria express metallo-beta-lactamase enzymes.

EXAMPLES

Abbreviations

BLA β-Lactam antibacterials
ca. circa (about)
DCM Dichloromethane
DIAD Diisopropyl azodicarboxylate
DMF Dimethylformamide
DMSO Dimethylsulfoxide
dppf 1,1'-Bis(diphenylphosphino)ferrocene
EDC 1-Ethyl-3-(3-dimethylaminopropyl)carbodiimide
ESI Electrospray ionization
HOBt Hydroxybenzotriazole
HPLC High performance liquid chromatography
IMP-1 Imipenemase-1
LCMS Liquid chromatography-mass spectrometry
MBL Metallo-beta-lactamase
MIC Minimum inhibitory concentration
MS Molecular sieves
m/z Mass/charge
NCS N-Chlorosuccinimide
NDM-1 New Delhi Metallo-beta-lactamase-1
NIS N-Iodosuccinimide
NMR Nuclear Magnetic Resonance
PTSA p-Toluenesulfonic acid
ppm parts per million
RT Retention time
rt Room temperature
SCX-2 Strong cation exchange (Si-Propylsulfonic acid)
TEA Triethylamine
THF Tetrahydrofuran
UV Ultraviolet
VIM Veronese metallo-β-lactamase
NDM New Delhi metallo-β-lactamase
IMP-1 Imipenemase-1

Materials and Methods

Standard experimental procedures were followed for synthesis; some of these are defined below.

Chemicals and solvents were from commonly used suppliers and were used without further purification. Silica gel 60 F254 analytical thin layer chromatography (TLC) plates were from Merck (Darmstadt, Germany) and visualized under UV light and/or with potassium permanganate stain. Chromatographic purifications were performed using Merck Geduran 60 silica (40-63 μm) or prepacked SNAP columns using a Biotage SP1 Purification system (Uppsala, Sweden). Microwave assisted reactions were performed using a Biotage Initiator™ microwave synthesizer in sealed vials. Deuterated solvents were obtained from Cambridge Isotopes, Sigma-Aldrich, Goss Scientific Instruments Ltd. and Apollo Scientific Ltd. All $^1$H and $^{13}$C NMR spectra were recorded using a Bruker spectrometer. All chemical shifts are given in ppm relative to the solvent peak, and coupling constants (J) are reported in Hz. High Resolution (HR) mass spectrometry data (m/z) were obtained from a Bruker Micro-TOF instrument using an ESI source and Time of Flight (TOF) analyzer. Low Resolution (LR) mass spectrometry data (m/z) were obtained from a Waters LCT Premier instrument using an ESI source and Time of Flight (TOF) analyzer or an Agilent Mass Spectrometer with a multimode source attached to an Agilent HPLC. Melting points were obtained using an automatic melting point apparatus.

LCMS Analytical Methods

Analytical Method A

LCMS was performed using an Agilent Mass Spectrometer with a multimode source.

Analysis was performed using either a Phenomenex or a Waters C18 column and the samples were monitored at 254 nm.

Synthesis of Compounds of the Invention

General Procedure A

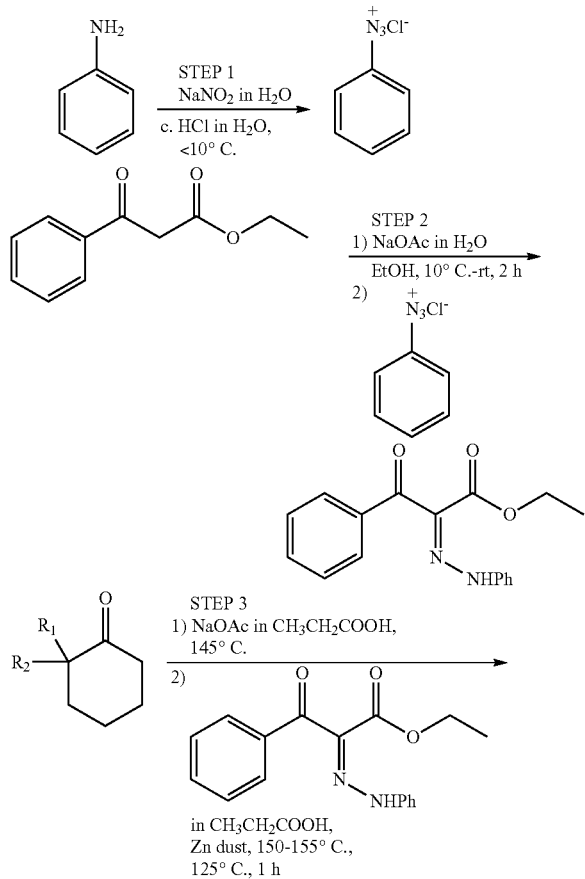

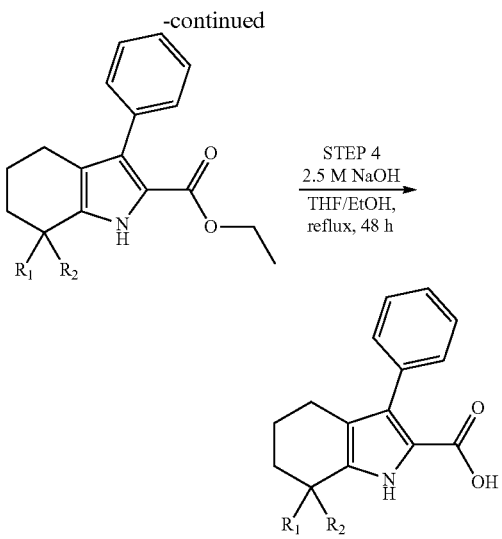

Example 1—3-phenyl-4,5,6,7-tetrahydro-1H-indole-2-carboxylic acid

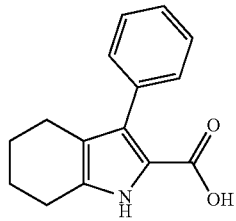 [SMILES: O=C(O)c1[nH]c2c(c1-c1ccccc1)CCCC2]

i) Synthesis of ethyl 3-phenyl-4,5,6,7-tetrahydro-1H-indole-2-carboxylate

Part A) To a mixture of conc. HCl (4.4 mL) and water (4.4 mL) was added aniline (2 mL). To this stirred solution, NaNO$_2$ (1.67 g) in water (7.3 mL) was added drop-wise while maintaining the temperature of the reaction mixture <10° C. After the addition was complete, the resultant diazonium salt solution was neutralized to congo red with saturated NaOAc. In a separate flask, to a solution of ethyl benzoylacetate (3.8 mL) in EtOH (18 mL) was added a solution of NaOAc (2.7 g) in water (5 mL) and the mixture was cooled to 10° C. To this, the diazonium salt solution was added over several minutes. The resulting mixture was stirred at 0° C. for 30 min and then allowed to stand at room temperature for 1 h. The mixture was diluted with EtOAc and water and the organic layer was separated. The aqueous layer was re-extracted with EtOAc. The organic fractions were combined, dried over Na$_2$SO$_4$, filtered and concentrated in vacuo to obtain the phenylhydrazone. The crude was taken through to the next step.

Part B) A mixture of cyclohexanone (2.27 mL), NaOAc (2.16 g) and propionic acid (13.2 mL) was placed in a round-bottomed flask and heated to 145° C. while stirring. A solution of the phenylhydrazone in propionic acid (13.2 mL) was added in small aliquots to the mixture, while small portions of Zn dust (5 g) were added simultaneously. The temperature was maintained between 150-160° C. Upon complete addition of the phenylhydrazone, the mixture was stirred at 125° C. for 1 h. If the reaction mixture became viscous with time, further portions of propionic acid were added as required to aid stirring. The reaction mixture was then cooled to 70° C., poured into ice-cold water and allowed to stand overnight. The resultant precipitate was filtered, washed with water to remove propionic acid, then washed with cyclohexane to obtain the desired compound.

$^1$H NMR (400 MHz, CDCl$_3$) δ 8.78 (1H, br. s, NH), 7.41-7.33 (4H, m, Ar—CH), 7.30-7.25 (1H, m, Ar—CH), 4.18 (2H, q, J=7.1 Hz, CO$_2$CH$_2$CH$_3$), 2.65 (2H, tt, J=6.3, 1.2 Hz, Cy-CH$_2$), 2.42 (2H, tt, J=6.0, 1.1 Hz, Cy-CH$_2$), 1.90-1.81 (2H, m, Cy-CH$_2$), 1.76-1.69 (2H, m, Cy-CH$_2$), 1.17 (3H, t, J=7.1 Hz, CO$_2$CH$_2$CH$_3$); HRMS (TOF, ESI$^+$) m/z: [M+H]$^+$ Calcd for C$_{17}$H$_{20}$O$_2$N 270.14886; Found 270.14853.

ii) Synthesis of 3-phenyl-4,5,6,7-tetrahydro-1H-indole-2-carboxylic acid

To a solution of ethyl 3-phenyl-4,5,6,7-tetrahydro-1H-indole-2-carboxylate (220 mg, 0.82 mmol) in THF (4.5 mL) and EtOH (1.5 mL) was added 2.5 M NaOH (1.64 mL). The resultant mixture was heated to reflux for 48 h. Upon completion, the reaction mixture was acidified to pH 2 with 2 M HCl and extracted with EtOAc (×3). The organic fractions were combined, dried over Na$_2$SO$_4$, filtered and concentrated in vacuo. The residue was treated with cyclohexane and the resultant precipitate was collected under suction filtration. The precipitate was washed with CH$_2$Cl$_2$ to obtain the desired compound.

$^1$H NMR (400 MHz, CD3OD) 7.36-7.17 (5H, m, Ar—CH), 2.63 (2H, t, J=6.3 Hz, Cy-CH$_2$), 2.36 (2H, t, J=6.2 Hz, Cy-CH$_2$), 1.87-1.77 (2H, m, Cy-CH$_2$), 1.74-1.66 (2H, m, Cy-CH$_2$); HRMS (TOF, ESI$^+$) m/z: [M+H]$^+$ Calcd for C$_{15}$H$_{16}$O$_2$N 242.11756; Found 242.11758.

Example 2—7-methyl-3-phenyl-4,5,6,7-tetrahydro-1H-indole-2-carboxylic acid

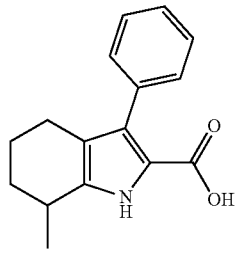 [SMILES: CC1CCCc2c1[nH]c(C(=O)O)c2-c1ccccc1]

i) Synthesis of ethyl 7-methyl-3-phenyl-4,5,6,7-tetrahydro-1H-indole-2-carboxyate The phenylhydrazone was synthesised from ethyl benzoylacetate (3.8 mL) as in Part A for Example 1. The pyrrole carboxylate ester was obtained from 2-methylcyclohexanone (2.27 mL) as in part B for Example 1.

$^1$H NMR (400 MHz, CDCl$_3$) δ 8.82 (1H, br. s, NH), 7.40-7.32 (4H, m, Ar—CH), 7.31-7.24 (1H, m, Ar—CH), 4.18 (2H, q, J=7.1 Hz, CO$_2$CH$_2$CH$_3$), 2.87 (1H, dqd, J=8.4, 6.9, 5.6 Hz, Cy-CH), 2.44-2.36 (2H, m, Cy-CH$_2$), 2.04-1.92 (1H, m, Cy-CH$_2$), 1.92-1.81 (1H, m, Cy-CH$_2$), 1.67-1.55 (1H, m, Cy-CH$_2$), 1.50-1.39 (1H, m, Cy-CH$_2$), 1.30 (3H, d, J=6.9 Hz, CH$_3$), 1.16 (3H, t, J=7.1 Hz, CO$_2$CH$_2$CH$_3$); HRMS (TOF, ESI$^+$) m/z: [M+Na]$^+$ Calcd for C$_{13}$H$_{21}$O$_2$NNa 306.14645; Found 306.14639.

ii) Synthesis of 7-methyl-3-phenyl-4,5,6,7-tetrahydro-1H-indole-2-carboxylic acid To a solution of ethyl 3-phenyl-4,5,6,7-tetrahydro-1H-indole-2-carboxylate (150 mg, 0.53 mmol) in THF (2.5 mL) and EtOH (1.5 mL) was added 2.5 M NaOH (1.08 mL). The resultant mixture was heated to reflux for 36 h. Upon completion, the reaction mixture was acidified to pH 2 with 2 M HCl and extracted with EtOAc (×3). The organic fractions were combined, dried over Na$_2$SO$_4$, filtered and concentrated in vacuo. The residue was treated with cyclohexane and the resulting precipitate was collected under suction filtration. The precipitate was washed with CH$_2$Cl$_2$ to obtain the desired compound.

$^1$H NMR (400 MHz, CD3D) δ 7.42-7.15 (5H, m, Ar—CH), 2.86 (1H, app h, J=6.9 Hz, Cy-CH), 2.40-2.24 (2H, m, Cy-CH$_2$), 2.02-1.92 (1H, m, Cy-CH$_2$), 1.88-1.73 (1H, m, Cy-CH$_2$), 1.67-1.53 (1H, m, Cy-CH$_2$), 1.52-1.39 (1H, m, Cy-CH$_2$), 1.29 (3H, d, J=6.9 Hz, CH$_3$); HRMS (TOF, ESI$^+$) m/z: [M+H]$^+$ Calcd for C$_{16}$H$_{18}$O$_2$N 256.13321; Found 256.13330.

Example 3—7,7-dimethyl-3-phenyl-4,5,6,7-tetrahydro-1H-indole-2-carboxylic acid

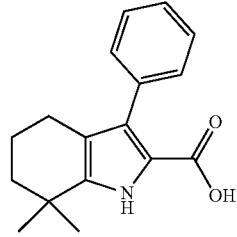 [SMILES: CC1(C)CCCc2c1[nH]c(C(=O)O)c2-c1ccccc1]

i) Synthesis of ethyl 7,7-dimethyl-3-phenyl-4,5,6,7-tetrahydro-1H-indole-2-carboxylate The phenylhydrazone was synthesised from ethyl benzoylacetate (1.25 mL) as in Part A for Example 1. The pyrrole carboxylate ester was obtained from 2,2-dimethylcyclohexanone (1.0 mL) as in part B for example 1.

$^1$H NMR (400 MHz, CDCl$_3$) δ 8.78 (1H, br. s, NH), 7.41-7.31 (4H, m, Ar—CH), 7.32-7.17 (1H, m, Ar—CH), 4.17 (2H, q, J=7.1 Hz, CO$_2$CH$_2$CH$_3$), 2.38 (2H, t, J=6.1 Hz, Cy-CH$_2$), 1.81-1.70 (2H, m, Cy-CH$_2$), 1.70-1.63 (2H, m, Cy-CH$_2$), 1.31 (6H, s, CH$_3$), 1.15 (3H, t, J=7.1 Hz, CO$_2$CH$_2$CH$_3$); HRMS (TOF, ESI$^+$) m/z: [M+H]$^+$ Calcd for C$_{19}$H$_{24}$O$_2$N 298.18016; Found 298.17990.

ii) Synthesis of 7,7-dimethyl-3-phenyl-4,5,6,7-tetrahydro-1H-indole-2-carboxylic acid To a solution of ethyl 3-phenyl-4,5,6,7-tetrahydro-1H-indole-2-carboxylate (150 mg, 0.50 mmol) in THF (3.0 mL) and EtOH (1.0 mL) was added 2.5 M NaOH (1.0 mL). The resultant mixture was heated to reflux for 36 h. Upon completion, the reaction mixture was acidified to pH 2 with 2 M HCl and extracted with EtOAc (×3). The organic fractions were combined, dried over Na$_2$SO$_4$, filtered and concentrated in vacuo. The residue was treated with cyclohexane and the resulting precipitate was collected under suction filtration. The precipitate was washed with CH$_2$Cl$_2$ to obtain the desired compound.

$^1$H NMR (400 MHz, CD$_3$OD) δ 7.33-7.27 (4H, m, Ar—CH), 7.25-7.19 (1H, m, Ar—CH), 2.31 (2H, t, J=6.0 Hz, Cy-CH$_2$), 1.79-1.70 (2H, m, Cy-CH$_2$), 1.70-1.64 (2H, m, Cy-CH$_2$), 1.32 (6H, s, CH$_3$); HRMS (TOF, ESI$^-$) m/z: [M−H]$^-$ Calcd for C$_{17}$H$_{18}$O$_2$N 268.13430; Found 268.13428.

General Procedure B

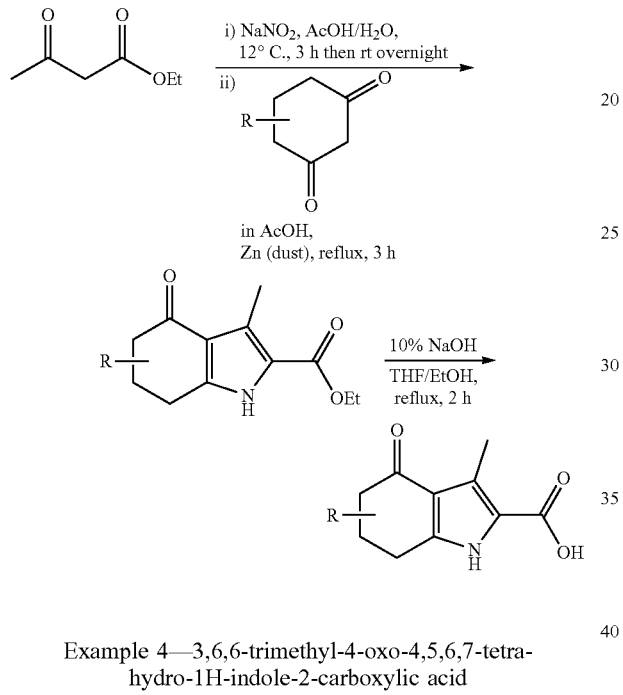

Example 4—3,6,6-trimethyl-4-oxo-4,5,6,7-tetrahydro-1H-indole-2-carboxylic acid

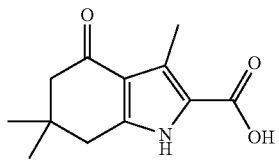 [SMILES: Cc1c(C(=O)O)[nH]c2c1C(=O)CC(C)(C)C2]

i) Synthesis of ethyl 3,6,6-trimethyl-4-oxo-4,5,6,7-tetrahydro-1H-indole-2-carboxylate To a solution of ethyl acetoacetate (1 mL) in acetic acid (2.6 mL) was added NaNO$_2$ (0.67 g) in water (2.2 mL) while maintaining the temperature of the reaction mixture <12° C. The resultant solution was stirred at a temperature <12° C. for 3 h and then at room temperature overnight. To this, 5,5-dimethyl-1,3-cyclohexanedione (1.51 g) in acetic acid (5.1 mL) was added followed by Zn dust (1.41 g), while maintaining the temperature of the reaction around 60° C. The mixture was stirred for 30 min, then heated to reflux for 3 h. The solution was separated from Zn dust by filtering through a plug of Celite. The filtrate was poured into ice-cold water and the precipitate was collected by suction filtration, then purified by flash column chromatography (EtOAc/cyclohexane) to obtain the desired product.

$^1$H NMR (400 MHz, CDCl$_3$) δ 9.54 (1H, br. s, NH), 4.33 (2H, q, J=7.1 Hz, CO$_2$CH$_2$CH$_3$), 2.66 (2H, s, CH$_2$), 2.59 (3H, s, CH$_3$), 2.34 (2H, s, CH$_2$), 1.37 (3H, t, J=7.1 Hz, CO$_2$CH$_2$CH$_3$), 1.09 (6H, s, 2×CH$_3$); HRMS (TOF, ESI$^-$) m/z: [M−H]$^-$ Calcd for C$_{14}$H$_{18}$O$_3$N 248.12922; Found 248.12913.

ii) Synthesis of 3,6,6-trimethyl-4-oxo-4,5,6,7-tetrahydro-1H-indole-2-carboxylic acid To a solution of ethyl 3,6,6-trimethyl-4-oxo-4,5,6,7-tetrahydro-1H-indole-2-carboxylate (0.25 g) in THF (4 mL) and EtOH (1.5 mL) was added 10% NaOH (1.6 mL) and heated to reflux for 2 h. Upon completion, the reaction mixture was acidified to pH 2 with 2 M HCl and extracted with EtOAc (×3). The organic fractions were combined, dried over Na$_2$SO$_4$, filtered and concentrated in vacuo. The crude residue was purified by flash column chromatography (DCM/methanol) to obtain the desired product.

$^1$H NMR (400 MHz, Methanol-d$_4$) δ 2.69 (2H, s, CH$_2$), 2.54 (3H, s, CH$_3$), 2.32 (2H, s, CH$_2$), 1.09 (6H, s, 2×CH$_3$); HRMS (TOF, ESI$^-$) m/z: [M−H]$^-$ Calcd for C$_{12}$H$_{14}$O$_3$N 220.09792; Found 220.09764.

Example 5—3,5,5-trimethyl-4-oxo-4,5,6,7-tetrahydro-1H-indole-2-carboxylic acid

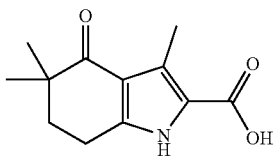 [SMILES: Cc1c(C(=O)O)[nH]c2c1C(=O)C(C)(C)CC2]

i) Synthesis of ethyl 3,5,5-trimethyl-4-oxo-4,5,6,7-tetrahydro-1H-indole-2-carboxylate The desired compound was obtained from 4,4-dimethyl-1,3-cyclohexanedione, using the same procedure as for example 4.

$^1$H NMR (400 MHz, CDCl$_3$) δ 9.88 (1H, br. s, NH), 4.33 (2H, q, J=7.1 Hz, CO$_2$CH$_2$CH$_3$), 2.82 (2H, t, J=6.3 Hz, CH$_2$), 2.58 (3H, s, CH$_3$), 1.95 (2H, t, J=6.3 Hz, CH$_2$), 1.36 (3H, t, J=7.1 Hz, CO$_2$CH$_2$CH$_3$), 1.15 (6H, s, 2×CH$_3$); HRMS (TOF, ESI$^-$) m/z: [M−H]$^-$ Calcd for C$_{14}$H$_{18}$O$_3$N 248.12922; Found 248.12911.

ii) Synthesis of 3,6,6-trimethyl-4-oxo-4,5,6,7-tetrahydro-1H-indole-2-carboxylic acid The desired compound was obtained from ethyl 3,5,5-trimethyl-4-oxo-4,5,6,7-tetrahydro-1H-indole-2-carboxylate, using the same procedure as for example 4.

$^1$H NMR (400 MHz, Methanol-d$_4$) δ 2.84 (2H, t, J=6.4 Hz, CH$_2$), 2.54 (3H, s, CH$_3$), 1.97 (2H, t, J=6.4 Hz, CH$_2$), 1.15 (6H, s, 2×CH$_3$); HRMS (TOF, ESI$^-$) m/z: [M−H]$^-$ Calcd for C$_{12}$H$_{14}$O$_3$N 220.09792; Found 220.09779.

General Procedure C

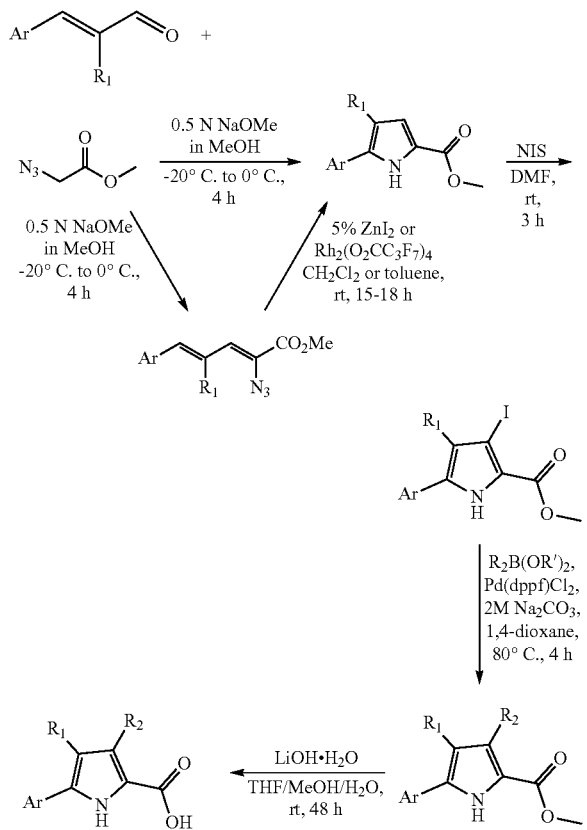

Example 6—3-(3,5-dichlorophenyl)-4-methyl-5-phenyl-1H-pyrrole-2-carboxylic acid

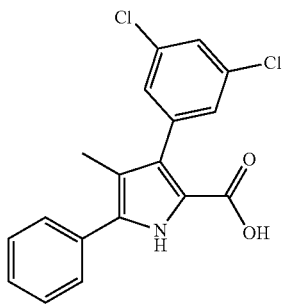

i) Synthesis of methyl 4-methyl-5-phenyl-1H-pyrrole-2-carboxylate

To a solution of 0.5 N NaOMe in MeOH (10.8 mL, 5.4 mmol) cooled to −20° C. was added a-methyl-trans-cinnamaldehyde (0.5 mL, 3.6 mmol). Methyl azidoacetate (1.4 mL, 14.3 mmol) was added drop-wise over several minutes and the reaction mixture was warmed to 0° C. and left to stir for 4 h. The reaction mixture was then concentrated in vacuo and treated with $H_2O$ followed by $Et_2O$. The organic phase was separated and the aqueous phase was re-extracted with $Et_2O$ (×2). The organic fractions were combined, dried over $MgSO_4$, filtered and concentrated in vacuo. The crude mixture was purified by flash chromatography (DCM/cyclohexane treated with 1% $Et_3N$). The product was isolated as a mixture with the starting material and the fractions were combined, concentrated in vacuo and re-subjected to column purification (DCM/cyclohexane without 1% $Et_3N$) to obtain the desired compound.

$^1$H NMR (400 MHz, $CDCl_3$) 9.57 (1H, br. s, NH), 7.55-7.48 (2H, m, Ar—CH), 7.43 (2H, dd, J=8.5, 6.9 Hz, Ar—CH), 7.37-7.29 (1H, m, Ar—CH), 6.82 (1H, d, J=2.6 Hz, Ar—CH), 3.81 (3H, s, $CO_2CH_3$), 2.26 (3H, s, $CH_3$); HRMS (TOF, ESI$^+$) m/z: [M+H]$^+$ Calcd for $C_{13}H_{14}O_2N$ 216.10191; Found 216.10194.

ii) Synthesis of methyl 3-iodo-4-methyl-5-phenyl-1H-pyrrole-2-carboxylate

To a solution of methyl 4-methyl-5-phenyl-1H-pyrrole-2-carboxylate (0.72 g, 3.33 mmol) in DMF (5 mL) was added N-iodosuccinamide (0.82 g, 3.66 mmol). The resulting mixture was stirred at room temperature for 3 h and then concentrated in vacuo. The crude mixture was dissolved in $CH_2Cl_2$ and washed with sat. $NaHCO_3$. The organic extracts were dried over $Na_2SO_4$, filtered and concentrated in vacuo. The residue was purified by flash chromatography (EtOAc in cyclohexane, 0-10%) to obtain the desired compound.

$^1$H NMR (400 MHz, $CDCl_3$) δ 9.44 (1H, br. s, NH), 7.47-7.43 (1H, m, Ar—CH), 7.40-7.32 (4H, m, Ar—CH), 3.87 (3H, s, $CO_2CH_3$), 2.21 (3H, s, $CH_3$); HRMS (TOF, ESI$^-$) m/z: [M−H]$^-$ Calcd for $C_{13}H_{11}NI$ 339.98399; Found 339.98398.

iii) Synthesis of methyl 3-(3,5-dichlorophenyl)-4-methyl-5-phenyl-H-pyrrole-2-carboxylate A mixture of methyl 3-iodo-4-methyl-5-phenyl-1H-pyrrole-2-carboxylate (0.75 g, 2.19 mml), 3,5-dichlorophenylboronic acid (0.5 g, 2.62 mmol), 2M $Na_2CO_3$ (4.36 mL) in 1,4-dioxane (20 mL) was purged with argon and treated with Pd(dppf)$Cl_2$ (69 mg, 0.09 mmol). After treating with the catalyst, the reaction mixture was purged with argon and then heated at 80° C. for 4 h. The resultant mixture was filtered through Decalite™, rinsing with EtOAc and water. The filtrate was partitioned between 1M HCl and EtOAc. The organic extracts were dried over $Na_2SO_4$, filtered and concentrated in vacuo. The residue was purified by flash chromatography (EtOAc in cyclohexane, 0-10%) to obtain the desired compound.

$^1$H NMR (400 MHz, $CDCl_3$) δ 9.28 (1H, br. s, NH), 7.42-7.31 (4H, m, Ar—CH), 7.29-7.20 (1H, m, Ar—CH), 7.14 (1H, d, J=1.9 Hz, Ar—CH), 3.57 (3H, s, $CO_2CH_3$), 1.97 (3H, s, $CH_3$); HRMS (TOF, ESI$^+$) m/z: [M+Na]$^+$ Calcd for $C_{19}H_{15}O_2NCl_2Na$ 382.03721, 384.03426; Found 382.03717, 384.03423.

iv) Synthesis of 3-(3,5-dichlorophenyl)-4-methyl-5-phenyl-1H-pyrrole-2-carboxylic acid To a solution of methyl 3-(3,5-dichlorophenyl)-4-methyl-5-phenyl-1H-pyrrole-2-carboxylate (200 mg, 0.56 mmol) in THF (2.4 mL), MeOH (1.0 mL) and $H_2O$ (1.0 mL) was added LiOH.$H_2O$ (117 mg, 2.78 mmol). The resultant mixture was stirred at room temperature for 48 h. Upon completion, the reaction mixture was acidified to pH 2 with 2 M HCl and extracted with EtOAc (×2). The organic fractions were combined, dried over $Na_2SO_4$, filtered and concentrated in vacuo. The residue was purified by flash chromatography (MeOH in DCM, 0-5%) to obtain the desired compound.

$^1$H NMR (400 MHz, CD$_3$OD) δ 7.58-7.54 (2H, m, Ar—CH), 7.46 (2H, app t, J=7.6 Hz, Ar—CH), 7.38-7.33 (2H, m, Ar—CH), 7.29 (2H, d, J=1.9 Hz, Ar—CH), 2.04 (3H, s, CH$_3$); HRMS (TOF, ESI$^-$) m/z: [M−H]$^-$ Calcd for C$_{18}$H$_{12}$O$_2$NCl$_2$ 344.02506, 346.02211; Found 344.02460.

Example 7—5-(5-(3,5-dichlorophenyl)furan-2-yl)-4-methyl-1H-pyrrole-2-carboxylic acid

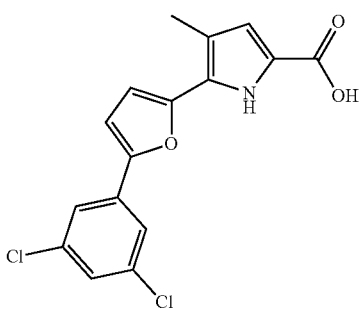 [SMILES: Cc1cc(C(=O)O)[nH]c1-c1ccc(-c2cc(Cl)cc(Cl)c2)o1]

i) Synthesis of methyl 2-azido-5-(furan-2-yl)-4-methylpenta-2,4-dienoate

To a solution of 0.5 N NaOMe in MeOH (12 mL, 6.0 mmol) cooled to −20° C. was added 2-methyl-3-(2-furyl)propenal (0.5 mL, 4.0 mmol). Methyl azidoacetate (1.6 mL, 16.0 mmol) was added drop-wise over several minutes and the reaction mixture was warmed to 0° C. and stirred for 4 h. The reaction mixture was then concentrated in vacuo and treated with H$_2$O followed by Et$_2$O. The organic phase was separated and the aqueous phase was re-extracted with Et$_2$O (×2). The organic fractions were combined, dried over MgSO$_4$, filtered and concentrated in vacuo. The crude mixture was purified by flash chromatography (DCM/cyclohexane treated with 1% Et$_3$N) to obtain the desired compound.

$^1$H NMR (400 MHz, CDCl$_3$) δ 7.47 (1H, dd, J=1.8, 0.8 Hz, Ar—CH), 6.72-6.69 (1H, m, C═CH), 6.60 (1H, d, J=0.8 Hz, C═CH), 6.51-6.45 (2H, m, Ar—CH), 3.86 (3H, s, CO$_2$CH$_3$), 2.34 (3H, d, J=1.1 Hz, CH$_3$); Mass observed for [(M−N$_2$)+H]$^+$.

ii) Synthesis of methyl 5-(furan-2-yl)-4-methyl-1H-pyrrole-2-carboxylate

To methyl 2-azido-5-(furan-2-yl)-4-methylpenta-2,4-dienoate (0.32 g, 1.37 mmol) dissolved in toluene (2 mL) was added Rh$_2$(O$_2$CC$_3$F$_7$)$_4$ (108.7 mg, 0.075 mmol) and was stirred at room temperature for 15 h. The resultant mixture was filtered through Decalite™ and concentrated in vacuo. The crude residue was purified by flash chromatography (EtOAc in cyclohexane, 0-20%) to obtain the desired compound.

$^1$H NMR (400 MHz, CDCl$_3$) δ 9.22 (1H, s, NH), 7.43 (1H, dd, J=1.8, 0.7 Hz, Ar—CH), 6.75 (1H, dd, J=2.8, 0.7 Hz, Ar—CH), 6.49 (1H, dd, J=3.4, 1.8 Hz, Ar—CH), 6.46 (1H, dd, J=3.4, 0.7 Hz, Ar—CH), 3.86 (3H, s, CO$_2$CH$_3$), 2.23 (3H, d, J=0.7 Hz, CH$_3$). HRMS (TOF, ESI$^+$) m/z: [M+H]$^+$ Calcd for C$_{11}$H$_{12}$O$_3$N 206.08117; Found 206.08143.

iii) Synthesis of methyl 5-(5-iodofuran-2-yl)-4-methyl-1H-pyrrole-2-carboxylate To a solution of methyl 5-(furan-2-yl)-4-methyl-1H-pyrrole-2-carboxylate (0.2 g, 0.98 mmol) in CH$_2$Cl$_2$ (1.5 mL) was added N-iodosuccinamide (0.24 g, 1.07 mmol). The resultant mixture was stirred at room temperature for 18 h. The reaction mixture was diluted with CH$_2$Cl$_2$ and washed with sat. NaHCO$_3$. The organic extracts were dried over Na$_2$SO$_4$, filtered and concentrated in vacuo. The residue was purified by flash chromatography (EtOAc in cyclohexane, 0-10%) to obtain the desired compound.

$^1$H NMR (400 MHz, CDCl$_3$) δ 9.17 (1H, br. s, NH), 6.74 (1H, app dd, J=2.7, 0.7 Hz, Ar—CH), 6.63 (1H, d, J=3.4 Hz, Ar—CH), 6.36 (1H, d, J=3.4 Hz, Ar—CH), 3.86 (3H, s, CO$_2$CH$_3$), 2.20 (3H, d, J=0.7 Hz, CH$_3$); HRMS (TOF, ESI$^+$) m/z: [M+H]$^+$ Calcd for C$_{11}$H$_{11}$O$_3$NI 331.97781; Found 331.97781.

iv) Synthesis of methyl 5-(5-(3,5-dichlorophenyl)furan-2-yl)-4-methyl-1H-pyrrole-2-carboxylate A mixture of methyl 5-(5-iodofuran-2-yl)-4-methyl-1H-pyrrole-2-carboxylate (0.6 g, 1.8 mmol), 3,5-dichlorophenylboronic acid (0.42 g, 2.18 mmol), 2M Na$_2$CO$_3$ (3.6 mL, 7.2 mmol) in 1,4-dioxane (16.2 mL) was purged with argon and treated with Pd(dppf)Cl$_2$ (57 mg, 0.08 mmol). After treating with the catalyst, the reaction mixture was purged with argon and then heated at 80° C. for 4 h. The resultant mixture was filtered through Decalite™, rinsing with EtOAc and water. The filtrate was partitioned between 1M HCl and EtOAc. The organic extracts were dried over Na$_2$SO$_4$, filtered and concentrated in vacuo. The residue was purified by flash chromatography (EtOAc in cyclohexane, 0-10%) to obtain the desired compound.

$^1$H NMR (400 MHz, CDCl$_3$) δ 9.24 (1H, br. s, NH), 7.56 (2H, d, J=1.9 Hz, Ar—CH), 7.25 (1H, t, J=1.9 Hz, Ar—CH), 6.80 (1H, d, J=3.6 Hz, Ar—CH), 6.78 (1H, dd, J=2.8, 0.7 Hz, Ar—CH), 6.55 (1H, d, J=3.6 Hz, Ar—CH), 3.89 (3H, s, CO$_2$CH$_3$), 2.28 (3H, d, J=0.7 Hz, CH$_3$); HRMS (TOF, ESI$^+$) m/z: [M+H]$^+$ Calcd for C$_{17}$H$_{14}$O$_3$NCl$_2$ 350.03453; Found 350.03455.

v) Synthesis of 5-(5-(3,5-dichlorophenyl)furan-2-yl)-4-methyl-1H-pyrrole-2-carboxylic acid To a solution of methyl 5-(5-(3,5-dichlorophenyl)furan-2-yl)-4-methyl-1H-pyrrole-2-carboxylate (200 mg, 0.57 mmol) in THF (2.4 mL), MeOH (1.0 mL) and H$_2$O (1.0 mL) was added LiOH.H$_2$O (224 mg, 5.7 mmol). The resultant mixture was stirred at room temperature for 48 h. Upon completion, the reaction mixture was acidified to pH 2 with 2 M HCl and extracted with EtOAc (×2). The organic fractions were combined, dried over Na$_2$SO$_4$, filtered and concentrated in vacuo. The residue was purified by flash chromatography (MeOH in DCM, 0-5%) to obtain the desired compound.

$^1$H NMR (400 MHz, DMSO-d$_6$) δ 12.39 (1H, br. s, OH), 12.05 (1H, d, J=2.6 Hz, NH), 7.95 (2H, d, J=1.9 Hz, Ar—CH), 7.47 (1H, t, J=1.9 Hz, Ar—CH), 7.33 (1H, d, J=3.6 Hz, Ar—CH), 6.86 (1H, d, J=3.6 Hz, Ar—CH), 6.68

(1H, d, J=2.6 Hz, Ar—CH), 2.25 (3H, s, CH₃); HRMS (TOF, ESI⁻) m/z: [M−H]⁻ Calcd for $C_{16}H_{10}O_3NCl_2$ 334.00432; Found 334.00424.

Example 8—3-(3-chloro-4-((methylsulfonyl)methyl) phenyl)-4-ethyl-5-(2-(trifluoromethyl)phenyl)-1H-pyrrole-2-carboxylic acid

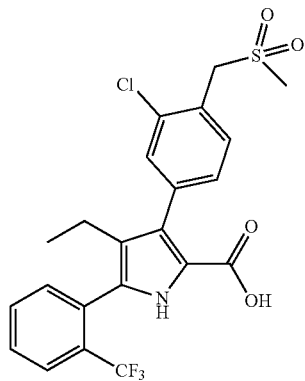 [SMILES: CCc1c(-c2ccccc2C(F)(F)F)[nH]c(C(=O)O)c1-c1ccc(CS(C)(=O)=O)c(Cl)c1]

i) Synthesis of methyl-2-azido-4-(-2-(trifluoromethyl)benzylidene)hex-2-enoate

To a solution of 0.5 N NaOMe in MeOH (13.8 mL, 6.9 mmol) cooled to −20° C. was added 2-(2-(trifluoromethyl)benzylidene)butanal (1.57 g, 6.9 mmol). Methyl azidoacetate (2.68 mL, 27.5 mmol) was added drop-wise over several minutes and the reaction mixture was warmed to 0° C. and stirred for 4 h. The resultant mixture was then concentrated in vacuo and treated with H₂O followed by Et₂O. The organic phase was separated and the aqueous phase was re-extracted with Et₂O (×2). The organic fractions were combined, dried over MgSO₄, filtered and concentrated in vacuo. The crude mixture was purified by flash chromatography (DCM/cyclohexane) to obtain the desired compound.

¹H NMR (400 MHz, CDCl₃) δ 7.68 (1H, d, J=7.8 Hz, Ar—CH), 7.55-7.50 (1H, m, Ar—CH), 7.41-7.35 (1H, m, Ar—CH), 7.31 (1H, d, J=7.8 Hz, Ar—CH), 7.12-7.08 (1H, m, C=CH), 6.61 (1H, d, J=1.0 Hz, C=CH), 3.89 (3H, s, CO₂CH₃), 2.41 (2H, q, J=7.5 Hz, CH₂CH₃), 1.02 (3H, t, J=7.5 Hz, CH₂CH₃); Mass observed for [M−N₂]⁺.

ii) Synthesis of methyl 4-ethyl-5-(2-(trifluoromethyl)phenyl)-1H-pyrrole-2-carboxylate To methyl-2-azido-4-(-2-(trifluoromethyl)benzylidene)hex-2-enoate (0.7 g, 2.15 mmol) dissolved in toluene (3 mL) was added Rh₂(O₂CC₃F₇)₄ (171 mg, 0.16 mmol) and was stirred at room temperature for 24 h. The resultant mixture was filtered through Decalite™ and concentrated in vacuo. The crude residue was purified by flash chromatography (EtOAc in cyclohexane, 0-20%) to obtain the desired compound.

HRMS (TOF, ESI⁺) m/z: [M+H]⁺ Calcd for $C_{15}H_{15}O_2NF_3$ 298.10494; Found 298.10513.

iii) Synthesis of methyl 4-ethyl-3-iodo-5-(2-(trifluoromethyl)phenyl)-1H-pyrrole-2-carboxylate To a solution of methyl 4-ethyl-5-(2-(trifluoromethyl)phenyl)-1H-pyrrole-2-carboxylate (0.48 g, 1.62 mmol) in DMF (2.5 mL) was added N-iodosuccinamide (0.40 g, 1.78 mmol). The resultant mixture was stirred at room temperature for 24 h and then concentrated in vacuo. The crude mixture was dissolved in CH₂Cl₂ and washed with sat. NaHCO₃. The organic extracts were dried over Na₂SO₄, filtered and concentrated in vacuo. The residue was purified by flash chromatography (EtOAc in cyclohexane, 0-10%) to obtain the desired compound.

¹H NMR (400 MHz, CDCl₃) δ 9.36 (1H, br. s, NH), 7.82-7.75 (1H, m, Ar—CH), 7.65-7.51 (2H, m, Ar—CH), 7.44-7.38 (1H, m, Ar—CH), 3.82 (3H, s, CO₂CH₃), 2.37 (2H, q, J=7.5 Hz, CH₂CH₃), 0.98 (3H, t, J=7.5 Hz, CH₂CH₃); HRMS (TOF, ESI⁺) m/z: [M+Na]⁺ Calcd for $C_{15}H_{13}O_2NF_3Na$ 445.9841; Found 445.9859.

iv) Synthesis of methyl 3-(3-chloro-4-((methylsulfonyl)methyl)phenyl)-4-ethyl-5-(2-(trifluoromethyl)phenyl)-1H-pyrrole-2-carboxylate A mixture of methyl 4-ethyl-3-iodo-5-(2-(trifluoromethyl)phenyl)-1H-pyrrole-2-carboxylate (0.20 g, 0.47 mmol), 2-(3-chloro-4-((methylsulfonylmethyl)phenyl)-4,4,5,5-tetramethyl-1,3,2-dioxoborolane (0.19 g, 0.57 mmol), 2M Na₂CO₃ (0.94 mL, 1.88 mmol) in 1,4-dioxane (4.2 mL) was purged with argon and treated with Pd(dppf)Cl₂. (15 mg, 0.02 mmol). After treating with the catalyst, the reaction mixture was purged with argon and then heated at reflux overnight. The resultant mixture was filtered through decalite, rinsing with EtOAc and water. The filtrate was partitioned between 1M HCl and EtOAc. The organic extracts were dried over Na₂SO₄, filtered and concentrated in vacuo. The residue was purified by flash chromatography (EtOAc in cyclohexane, 0-50%) to obtain the desired compound.

¹H NMR (400 MHz, CDCl₃) δ 9.23 (1H, br. s, NH), 7.88-7.77 (1H, m, Ar—CH), 7.71-7.47 (5H, m, Ar—CH), 7.40 (1H, dd, J=7.9, 1.7 Hz, Ar—CH), 4.55 (2H, s, CH₂), 3.68 (3H, s, CO₂CH₃), 2.87 (3H, s, CH₃), 2.34 (2H, q, J=7.5 Hz, CH₂CH₃), 0.74 (3H, t, J=7.5 Hz, CH₂CH₃); HRMS (TOF, ESI⁺) m/z: [M+H]⁺ Calcd for $C_{23}H_{22}ClF_3NO_4S$ 500.0910; Found 500.0921.

v) Synthesis of 3-(3-chloro-4-((methylsulfonyl)methyl)phenyl)-4-ethyl-5-(2-(trifluoromethyl)phenyl)-1H-pyrrole-2-carboxylic acid To a solution of methyl 3-(3-chloro-4-((methylsulfonyl)methyl)phenyl)-4-ethyl-5-(2-(trifluoromethyl)phenyl)-1H-pyrrole-2-carboxylate (0.22 g, 0.44 mmol) in THF (2.0 mL), MeOH (1.0 mL) and H₂O (1.0 mL) was added LiOH.H₂O (185 mg, 4.4 mmol). The resultant mixture was stirred at room temperature for 48 h and then at 45° C. for 4 h. Upon completion, the reaction mixture was acidified to pH 2 with 2 M HCl and extracted with EtOAc (×2). The organic fractions were combined, dried over Na₂SO₄, filtered and concentrated in vacuo. The residue was dissolved in CH₂Cl₂ and treated with cyclohexane to precipitate the product. The product was then isolated by suction filtration.

¹H NMR (400 MHz, CD₃OD) δ 7.87-7.81 (1H, m, Ar—CH), 7.75-7.45 (5H, m, Ar—CH), 7.37 (1H, dd, J=7.9, 1.7 Hz, Ar—CH), 4.66 (2H, s, CH₂), 2.96 (3H, s, CH₃), 2.27 (2H, q, J=7.5 Hz, CH₂CH₃), 0.71 (3H, t, J=7.5 Hz, CH₂CH₃); HRMS (TOF, ESI⁺) m/z: [M+Na]⁺ Calcd for $C_{22}H_{19}O_4NClF_3NaS$ 508.05676; Found 508.05698.

Synthesis of 2-(2-(trifluoromethyl)benzylidene)butanal

To a solution of 2-(trifluoromethyl)benzaldehyde (1 mL, 7.58 mmol) in methanol (5.3 mL) was added NaOH (61 mg, 1.52 mmol) and the reaction mixture cooled to 0° C. Butanal (0.89 mL, 9.85 mmol) was added drop wise and the resulting solution was stirred at room temperature for 2 h. The resultant mixture was diluted with water and extracted with EtOAc. The organic fractions were dried over $Na_2SO_4$, filtered and concentrated in vacuo. The crude mixture was purified by flash chromatography (EtOAc in cyclohexane, 0-5%).

$^1$H NMR (400 MHz, $CDCl_3$) δ 9.59 (s, 1H), 7.78-7.69 (m, 1H), 7.63-7.52 (m, 1H), 7.53-7.42 (m, 1H), 7.43-7.34 (m, 1H), 2.31 (q, J=7.5 Hz, 2H), 0.99 (t, J=7.5 Hz, 3H); HRMS (TOF, ESI$^+$) m/z: [M+H]$^+$ Calcd for $C_{12}H_{11}F_3O$ 229.0843; Found 229.0835.

Example 9—3-(4-(carboxymethyl)phenyl)-4-methyl-5-phenyl-1H-pyrrole-2-carboxylic acid

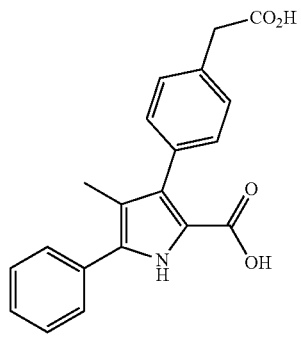 [SMILES: Cc1c(-c2ccccc2)[nH]c(C(=O)O)c1-c1ccc(CC(=O)O)cc1]

i) Synthesis of 2-(4-(2-(methoxycarbonyl)-4-methyl-5-phenyl-1H-pyrrol-3-yl)phenyl)acetic acid To a mixture of methyl 3-iodo-4-methyl-5-phenyl-1H-pyrrole-2-carboxylate (1 eq) and 2-(4-boronophenyl)acetic acid in DMF was added $Cs_2CO_3$ (3 eq), then purged with argon and treated with tetrakis(triphenylphosphine)palladium(0) (10 mol %). The reaction mixture was heated at 110° C. overnight. The product was purified by flash chromatography to obtain the desired compound.

$^1$H NMR (400 MHz, DMSO-$d_6$) δ 12.21 (1H, br. s, $CO_2H$), 11.81 (1H, br. s, NH), 7.61-7.27 (9H, m, Ar—CH), 3.76 (2H, s, $CH_2$), 2.10 (3H, s, $CH_3$); LCMS [M+H]$^+$ 350.2.

ii) Synthesis of 3-(4-(carboxymethyl)phenyl)-4-methyl-5-phenyl-1H-pyrrole-2-carboxylic acid To a solution of 2-(4-(2-(methoxycarbonyl)-4-methyl-5-1H-pyrrol-3-yl)phenyl)acetic acid in THF/MeOH/$H_2O$ (5:1:1) was added LiOH.$H_2O$ (20 eq). The resultant mixture was stirred at room temperature for 48 h and concentrated in vacuo. The residue was purified by flash column chromatography to obtain the desired product.

$^1$H NMR (400 MHz, DMSO-$d_6$) δ 12.30 (1H, br. s, $CO_2H$), 11.79 (1H, br. s, NH), 7.74-7.08 (9H, m, Ar—CH), 3.74-3.48 (5H, s, $CH_2$+$OCH_3$), 1.99 (3H, s, $CH_3$); HRMS (TOF, ESI$^-$) m/z: [M–H]$^-$ Calcd for $C_{20}H_{16}O_4N$ 334.10848; Found 334.10842.

Example 10—3-(4-hydroxyphenyl)-4-methyl-5-phenyl-1H-pyrrole-2-carboxylic acid

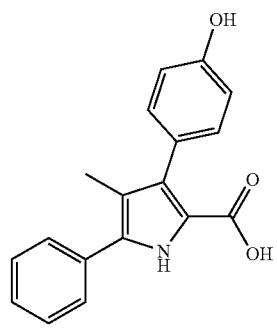 [SMILES: Cc1c(-c2ccccc2)[nH]c(C(=O)O)c1-c1ccc(O)cc1]

i) Synthesis of methyl 3-(4-hydroxyphenyl)-4-methyl-5-phenyl-1H-pyrrole-2-carboxylate To a mixture of methyl 3-iodo-4-methyl-5-phenyl-1H-pyrrole-2-carboxylate (1 eq) and (4-hydroxyphenyl)boronic acid (1.1 eq) in acetonitrile was added $K_2CO_3$ (3 eq), then purged with argon and treated with tetrakis(triphenylphosphine)palladium(0) (5 mol %). The reaction mixture was heated at 110° C. for 4 h. The product was purified by flash chromatography to obtain the desired compound.

$^1$H NMR (400 MHz, DMSO-$d_6$) δ 11.68 (1H, br. s, NH), 9.38 (1H, br. s, OH), 7.61-7.54 (2H, m, Ar—CH), 7.50-7.40 (2H, m, Ar—CH), 7.39-7.29 (1H, m, Ar—CH), 7.10 (2H, d, J=8.5 Hz, Ar—CH), 6.77 (2H, d, J=8.5 Hz, Ar—CH), 3.61 (3H, s, $OCH_3$), 1.97 (3H, s, $CH_3$); LCMS [M+H]$^+$ 308.6.

ii) Synthesis of 3-(4-hydroxyphenyl)-4-methyl-5-phenyl-1H-pyrrole-2-carboxylic acid To a solution of methyl 3-(4-hydroxyphenyl)-4-methyl-5-phenyl-1H-pyrrole-2-carboxylate in THF/MeOH/$H_2O$ (5:1:1) was added LiOH.$H_2O$ (20 eq). The resultant mixture was stirred at room temperature for 48 h and concentrated in vacuo. The residue was purified by flash column chromatography to obtain the desired product.

$^1$H NMR (400 MHz, DMSO-$d_6$) δ 11.94 (1H, br. s, $CO_2H$), 11.49 (1H, br. s, NH), 9.32 (1H, br. s, OH), 7.70-7.46 (2H, m, Ar—CH), 7.43 (2H, app t, J=7.7 Hz, Ar—CH), 7.35-7.26 (1H, m, Ar—CH), 7.10 (2H, d, J=8.5 Hz, Ar—CH), 6.74 (2H, d, J=8.5 Hz, Ar—CH), 1.96 (3H, s, $CH_3$); HRMS (TOF, ESI$^-$) m/z: [M–H]$^-$ Calcd for $C_{18}H_{14}O_3N$ 292.09792; Found 292.09774.

Example 11—3-(4-((N,N-dimethylsulfamoyl)methyl)phenyl)-4-methyl-5-phenyl-1H-pyrrole-2-carboxylic acid

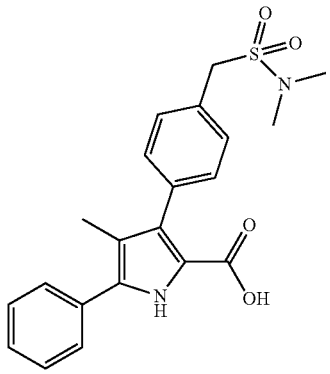 [SMILES: Cc1c(-c2ccccc2)[nH]c(C(=O)O)c1-c1ccc(CS(=O)(=O)N(C)C)cc1]

i) Synthesis of methyl 3-(4-((N,N-dimethylsulfamoyl)methyl)phenyl)-4-methyl-5-phenyl-1H-pyrrole-2-carboxylate A mixture of methyl 3-iodo-4-methyl-5-phenyl-1H-pyrrole-2-carboxylate (1 eq), N,N-dimethyl-1-(4-(4,4,5,5-tetramethyl-1,3,2-dioxaborolan-2-yl)phenyl)methanesulfonamide (1.2 eq), 2M $Na_2CO_3$ (4 eq) in 1,4-dioxane (9 mL/mmol) was purged with argon and treated with Pd(dppf)$Cl_2$ (4 mol %). After treating with the catalyst, the reaction mixture was purged with argon and then heated at reflux overnight. The resultant mixture was filtered through decalite, rinsing with EtOAc and water. The filtrate was partitioned between 1M HCl and EtOAc. The organic extracts were dried over $Na_2SO_4$, filtered and concentrated in vacuo. The residue was purified by flash chromatography to obtain the desired compound.

$^1$H NMR (400 MHz, DMSO-$d_6$) δ 11.85 (1H, br. s, NH), 7.62-7.56 (2H, m, Ar—CH), 7.50-7.41 (4H, m, Ar—CH), 7.38-7.29 (3H, m, Ar—CH), 4.46 (2H, s, $CH_2$), 3.58 (3H, s, $OCH_3$), 2.72 (6H, s, N($CH_3$)$_2$), 1.97 (3H, s, $CH_3$).

ii) Synthesis of 3-(4-((N,N-dimethylsulfamoyl)methyl)phenyl)-4-methyl-5-phenyl-1H-pyrrole-2-carboxylic acid To a solution of methyl 3-(4-((N,N-dimethylsulfamoyl)methyl)phenyl)-4-methyl-5-phenyl-1H-pyrrole-2-carboxylate (1 eq) in THF/MeOH/$H_2O$ (2:1:1) was added LiOH.$H_2O$ (10 eq). The resultant mixture was stirred at room temperature for 48 h and acidified to pH 2 with 2 M HCl, then extracted with EtOAc (×2). The organic fractions were combined, dried over $Na_2SO_4$, filtered and concentrated in vacuo. The residue was purified by flash column chromatography.

$^1$H NMR (400 MHz, DMSO-$d_6$) δ 11.69 (1H, br. s, NH), 9.32 (1H, br. s), 7.63-7.56 (2H, m, Ar—CH), 7.49-7.38 (4H, m, Ar—CH), 7.36-7.27 (3H, m, Ar—CH), 4.44 (2H, s, $CH_2$), 2.72 (6H, s, N($CH_3$)$_2$), 1.97 (3H, s, $CH_3$); HRMS (TOF, ESI$^-$) m/z: [M–H]$^-$ Calcd for $C_{21}H_{21}O_4N_2S$ 397.12275; Found 397.12220.

Examples 12-14

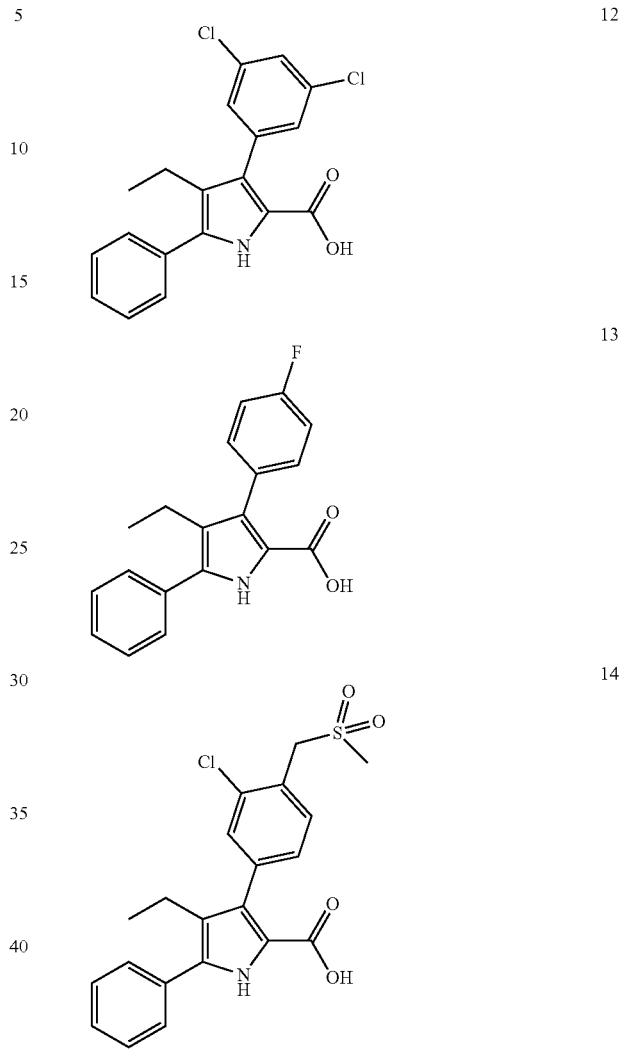

i) Synthesis of methyl 4-ethyl-5-phenyl-1H-pyrrole-2-carboxylate

To a cooled (−22° C.) solution of sodium methoxide (0.81 g, 15 mmol) in MeOH (40 mL), (E)-2-benzylidenebutanal (1.60 g, 10 mmol) in MeOH (5 mL) was added dropwise. This was followed by the addition of methyl 2-azidoacetate (4.58 mL, 40 mmol) in MeOH (5 mL) during 1 h in 5 min intervals. The reaction mixture was warmed to −10° C. and stirred at this temperature for 4 h. The mixture was diluted with water (10 mL) and EtOAc (25 mL). The organic layer was separated and the aqueous layer was extracted twice with EtOAc (2×10 mL). The combined organic layers were dried over $Na_2SO_4$, filtered and concentrated under reduced pressure. The crude product was purified using silica gel column chromatography applying a gradient of EtOAc/cyclohexane: 0/100 to 20/80 (v/v) to give a white solid.

$^1$H NMR (500 MHz, CDCl$_3$) δ 9.03 (1H, br. s, NH), 7.47-7.42 (4H, m, Ar—CH), 7.36-7.32 (1H, m, Ar—CH), 6.89 (1H, d, J=2.6 Hz, Ar—CH), 3.85 (3H, s, $CO_2CH_3$), 2.64

(2H, q, J=7.5 Hz, CH$_2$CH$_3$), 1.23 (3H, t, J=7.5 Hz, CH$_2$CH$_3$); M+1 m/z, 230. LCMS purity 95% (254 nm).

ii) Synthesis of methyl 4-ethyl-3-iodo-5-phenyl-1H-pyrrole-2-carboxylate

A solution of methyl 4-ethyl-5-phenyl-1H-pyrrole-2-carboxylate (0.36 g, 1.58 mmol) and NIS (0.39 g, 1.74 mmol) in DMF (5 mL) was stirred at room temperature for 3 h. Then, more NIS (0.065 g, 0.29 mmol) was added and the reaction mixture was stirred for 2 h at room temperature. The reaction mixture was diluted with EtOAc (10 mL) and washed twice with water (2×10 mL), brine (2×10 mL) and satd. aq. NaHCO$_3$ (10 mL). The combined organic layers were dried over Na$_2$SO$_4$, filtered and concentrated under reduced pressure. The crude product was purified using silica gel column chromatography applying a gradient of EtOAc/cyclohexane: 0/100 to 50/50 (v/v) to afford a yellow solid.

$^1$H NMR (500 MHz, CDCl$_3$) δ 9.21 (1H, br. s, NH), 7.47-7.43 (4H, m, Ar—CH), 7.40-7.37 (1H, m, Ar—CH), 3.90 (3H, s, CO$_2$CH$_3$), 2.60 (2H, q, J=7.5 Hz, CH$_2$CH$_3$), 1.18 (3H, t, J=7.5 Hz, CH$_2$CH$_3$); M+1 m/z 356. LCMS purity 95% (254 nm).

General Procedure for Suzuki-Miyaura Cross Coupling

A mixture of methyl 3-ethyl-4-iodo-5-phenyl-1H-pyrrole-2-carboxylate (1 eq), boronic acid (1.2 eq), PdCl$_2$(dppf) (0.05 eq), aq. Na$_2$CO$_3$ (2M, 4 eq) and 1,4-dioxane (4 mL per 0.4 mmol) was purged with N2 (10 min). Then, the mixture was stirred at 90° C. for 3 h. The reaction mixture was cooled to room temperature, diluted with water (20 mL) and extracted with EtOAc (3×10 mL). The combined organic layers were dried over Na$_2$SO$_4$, filtered and concentrated under reduced pressure. The crude product was purified using silica gel column chromatography applying a gradient of EtOAc/cyclohexane, 0/100 to 20/80 (v/v).

iii) Synthesis of methyl 3-(3,5-dichlorophenyl)-4-ethyl-5-phenyl-1H-pyrrole-2-carboxylate $^1$H NMR (500 MHz, CDCl$_3$) 9.13 (1H, br. s, NH), 7.51-7.45 (5H, m, Ar—CH), 7.40-7.34 (3H, m, Ar—CH), 3.70 (3H, s, CO$_2$CH$_3$), 2.53 (2H, d, J=7.5 Hz, CH$_2$CH$_3$), 0.92 (3H, t, J=7.5 Hz, CH$_2$CH$_3$); M+1 m/z 374. LCMS purity 87% (254 nm).

iv) Synthesis of methyl 4-ethyl-3-(4-fluorophenyl)-5-phenyl-1H-pyrrole-2-carboxylate $^1$H NMR (500 MHz, CDCl$_3$) δ 9.16 (1H, br. s, NH), 7.54-7.52 (2H, m, Ar—CH), 7.48-7.45 (2H, m, Ar—CH), 7.39-7.31 (3H, m, Ar—CH), 7.12-7.08 (2H, m, Ar—CH), 3.66 (3H, s, CO$_2$CH$_3$), 2.54 (2H, d, J=7.5 Hz, CH$_2$CH$_3$), 0.91 (3H, t, J=7.5 Hz, CH$_2$CH$_3$); M+1 m/z 324. LCMS purity 95% (254 nm).

v) Synthesis of methyl-(3-chloro-4-((methylsulfonyl)methyl)phenyl)-4-ethyl-5-phenyl-1H-pyrrole-2-carboxylate $^1$H NMR (500 MHz, CDCl$_3$) δ 9.33 (1H, br. s, NH), 7.62-7.60 (1H, m, Ar—CH), 7.53-7.44 (5H, m, Ar—CH), 7.38-7.34 (2H, m, Ar—CH), 4.56 (2H, s, CH$_2$), 3.66 (3H, s, CO$_2$CH$_3$), 2.88 (3H, s, CH$_3$), 2.53 (2H, d, J=7.2 Hz, CH$_2$CH$_3$), 0.90 (3H, t, J=6.9 Hz, CH$_2$CH$_3$); M+1 m/z 432. LCMS purity 95% (254 nm).

General Procedure for Hydrolysis of Methyl Ester

A mixture of methyl carboxylate analogue (1 eq), LiOH.H$_2$O (4 eq), THF (1.4 mL), MeOH (0.5 mL) and water (0.5 mL) was stirred at 80° C. for 2 h. The reaction mixture was cooled to room temperature, acidified to pH=2 with 2M HCl and extracted with EtOAc (20 mL). If the pH had drifted, the aqueous layer was reacidified again to pH=2 with 2M HCl and extracted with EtOAc (3×20 mL). All combined organic layers were dried over Na$_2$SO$_4$, filtered and concentrated under reduced pressure. The crude product was purified using silica gel column chromatography eluting with DCM/MeOH, 95/5 (v/v).

vi) Synthesis of 3-(3,5-dichlorophenyl)-4-ethyl-5-phenyl-1H-pyrrole-2-carboxylic acid (Example 12)

$^1$H NMR (600 MHz, CD$_3$OD) δ 7.55-7.53 (2H, m), 7.40-7.34 (2H, m), 7.31-7.29 (4H, m), 2.55 (2H, d, J=7.5 Hz), 0.91 (3H, t, J=7.5 Hz); M+1 m/z 360. LCMS purity 95% (254 nm). HRMS [M+Na]$^+$ calcd for C$_{19}$H$_{15}$Cl$_2$NO$_2$Na: 382.0480, found 382.0357.

vii) Synthesis of 4-ethyl-3-(4-fluorophenyl)-5-phenyl-1H-pyrrole-2-carboxylic acid (Example 13)

$^1$H NMR (600 MHz, CD$_3$OD) δ 7.57-7.55 (2H, m), 7.45-7.43 (2H, m), 7.36-7.30 (3H, m), 7.07-7.04 (2H, m), 2.53 (2H, d, J=7.5 Hz), 0.87 (3H, t, J=7.5 Hz); M+1 m/z 310. LCMS purity 95% (254 nm). HRMS [M+Na]$^+$ calcd for C$_{19}$H$_{16}$FNO$_2$Na: 332.1165, found 332.1041.

viii) Synthesis of 3-(3-chloro-4-((methysulfonyl)methyl)phenyl)-4-ethyl-5-phenyl-1H-pyrrole-2-carboxylic acid (Example 14)

$^1$H NMR (600 MHz, CD$_3$OD) δ 7.56-7.52 (4H, m), 7.45-7.42 (3H, m), 7.39-7.37 (1H, m), 7.32-7.29 (1H, m), 4.63 (2H, s), 2.94 (3H, s), 2.59 (2H, d, J=7.4 Hz), 0.91 (3H, t, J=7.4 Hz); M+1 m/z 418. LCMS purity 99% (254 nm). HRMS [M+H]$^+$ calcd for C$_{21}$H$_{21}$ClNO$_4$S: 418.0802, found 418.0865.

Synthesis of (E)-2-benzylidenebutanal

A round-bottomed flask was charged with EtOH (20 mL), NaOH (1.88 g, 47.1 mmol), water (20 mL) and benzaldehyde (4.79 mL, 47.1 mmol). The reaction mixture was cooled in an ice bath and butanal (5.52 mL, 61.30 mmol) was added dropwise. After stirring at room temperature for 4 h, the mixture was warmed to 30° C. for 2 h. The reaction mixture was cooled to room temperature and quenched by adding aq. HCl (1M) (47.1 mL, 47.1 mmol). The neutralized mixture was extracted with Et$_2$O (3×25 mL). The combined organic layers were dried over Na$_2$SO$_4$, filtered and concentrated under reduced pressure. Purification was performed using silica gel column chromatography applying a gradient of DCM/cyclohexane: 0/100 to 80/20 (v/v). This gave a yellow oil (4.0 g, 50%).

$^1$H NMR (500 MHz, CDCl$_3$) δ 9.60 (br. s, 1H), 7.58-7.54 (m, 2H), 7.53-7.48 (m, 2H), 7.48-7.43 (m, 1H), 7.1 (s, 1H), 2.61 (q, J=7.5 Hz, 2H), 1.20 (t, J=7.5 Hz, 3H). M+1 m/z 161.

General Procedure D

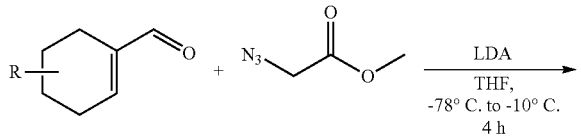

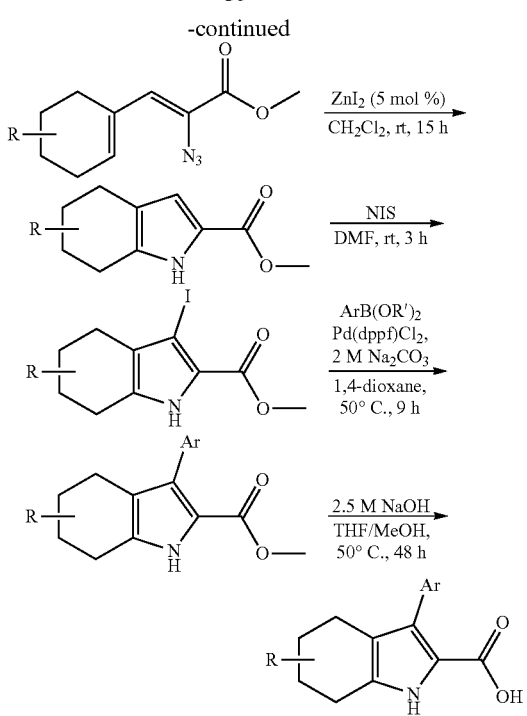

Example 15—3-(3,5-dichlorophenyl)-5,5-dimethyl-4,5,6,7-tetrahydro-1H-4,6-methanoindole-2-carboxylic acid

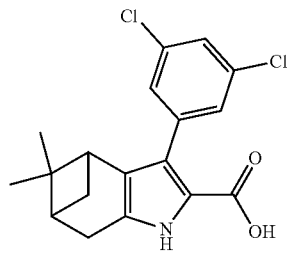 [SMILES: CC1(C)C2Cc3[nH]c(C(=O)O)c(-c4cc(Cl)cc(Cl)c4)c3C1C2]

i) Synthesis of methyl 5,5-dimethyl-4,5,6,7-tetrahydro-1H-4,6-methanoindole-2-carboxyate A solution of 2 M LDA in THF (3.45 mL, 6.9 mmol) was cooled to −78° C. and was added 1R-(−)-myrtenal (1.0 mL, 6.6 mmol). Methyl azidoacetate (2.6 mL, 26.3 mmol) was added drop-wise over several minutes and the reaction mixture was warmed to −10° C. and stirred for 4 h. The reaction mixture was then quenched with water and diluted with Et$_2$O. The organic phase was separated and the aqueous phase was re-extracted with Et$_2$O (×2). The organic fractions were combined, dried over MgSO$_4$, filtered and concentrated in vacuo. The crude mixture was then dissolved in CH$_2$Cl$_2$ (4.6 mL), treated with 5% ZnI$_2$ (0.105 g, 0.33 mmol) and was stirred at room temperature for 15 h. The resulting mixture was filtered through decalite and concentrated in vacuo. The crude residue was purified by flash chromatography (EtOAc in cyclohexane, 0-10%) to obtain the desired compound.

$^1$H NMR (400 MHz, CDCl$_3$) δ 9.28 (1H, br. s, NH), 6.61 (1H, d, J=2.1 Hz, Ar—CH), 3.81 (3H, s, CO$_2$CH$_3$), 2.86 (1H, dd, J=16.5, 3.1 Hz, CHH), 2.77 (1H, dd, J=16.5, 2.8 Hz, CHH), 2.71-2.62 (2H, m, CHH+CH), 2.28 (1H, app tt, J=5.8, 2.9 Hz, CH), 1.37 (3H, s, CH$_3$), 1.32 (1H, d, J=9.0 Hz, CHH), 0.62 (3H, s, CH$_3$); HRMS (TOF, ESI$^+$) m/z: [M+H]$^+$ Calcd for C$_{13}$H$_{18}$O$_2$N 220.13321; Found 220.13337.

ii) Synthesis of methyl 3-iodo-5,5-dimethyl-4,5,6,7-tetrahydro-1H-4,6-methanoindole-2-carboxylate To a solution of methyl 5,5-dimethyl-4,5,6,7-tetrahydro-1H-4,6-methanoindole-2-carboxylate (0.72 g, 3.30 mmol) in DMF (5 mL) was added N-iodosuccinamide (0.82 g, 3.63 mmol). The resultant mixture was stirred at room temperature for 3 h and then concentrated in vacuo. The crude mixture was dissolved in CH$_2$Cl$_2$ and washed with sat. NaHCO$_3$. The organic extracts were dried over Na$_2$SO$_4$, filtered and concentrated in vacuo. The residue was purified by flash chromatography (EtOAc in cyclohexane, 0-10%) to obtain the desired compound.

$^1$H NMR (400 MHz, CDCl$_3$) δ 369.24 (1H, br. s, NH), 3.86 (3H, s, CO$_2$CH$_3$), 2.83 (1H, dd, J=16.5, 3.1 Hz, CHH), 2.78-2.66 (2H, m, CHH+ CHH), 2.60 (1H, app t, J=5.4 Hz, CH), 2.31 (1H, app tt, J=5.8, 2.9 Hz, CH), 1.40 (3H, s, CH$_3$), 1.28 (1H, d, J=9.5 Hz, CHH), 0.60 (3H, s, CH$_3$); HRMS (TOF, ESI$^-$) m/z: [M−H]$^-$ Calcd for C$_{13}$H$_{15}$O$_2$NI 344.01530; Found 344.01508.

iii) Synthesis of methyl 3-(3,5-dichlorophenyl)-5,5-dimethyl-4,5,6,7-tetrahydro-1H-4,6-methanoindole-2-carboxylate A mixture of methyl 3-iodo-5,5-dimethyl-4,5,6,7-tetrahydro-1H-4,6-methanoindole-2-carboxylate (0.55 g, 1.61 mmol), 3,5-dichlorophenylboronic acid (0.37 g, 1.94 mmol), 2M Na$_2$CO$_3$ (3.2 mL) in 1,4-dioxane (15 mL) was purged with argon and treated with Pd(dppf)Cl$_2$ (50 mg, 0.07 mmol). After treating with the catalyst, the reaction mixture was purged with argon and then heated at 50° C. for 9 h. The resultant mixture was filtered through decalite, rinsing with EtOAc and water. The filtrate was partitioned between water and EtOAc. The organic extracts were dried over Na$_2$SO$_4$, filtered and concentrated in vacuo. The residue was purified by flash chromatography (EtOAc in cyclohexane, 0-10%) to obtain the desired compound.

$^1$H NMR (400 MHz, CDCl) 369.62 (1H, br. s, NH), 7.27 (1H, t, J=1.9 Hz, Ar—CH), 7.20 (2H, d, J=1.9 Hz, Ar—CH), 3.74 (3H, s, CO$_2$CH$_3$), 2.90 (1H, dd, J=16.6, 3.1 Hz, CHH), 2.81 (1H, dd, J=16.6, 2.8 Hz, CHH), 2.70 (1H, app dt, J=9.3, 5.7 Hz, CHH), 2.62 (1H, app t, J=5.4 Hz, CH), 2.32 (1H, app tt, J=5.7, 2.9 Hz, CH), 1.37 (3H, s, CH$_3$), 1.35-1.33 (1H, m, CHH), 0.68 (3H, s, CH$_3$); HRMS (TOF, ESI$^-$) m/z: [M−H]$^-$ Calcd for C$_{19}$H$_{18}$O$_2$NCl$_2$ 362.07201; Found 362.07214.

iv) Synthesis of 3-(3,5-dichlorophenyl)-5,5-dimethyl-4,5,6,7-tetrahydro-1H-4,6-methanoindole-2-carboxylic acid To a solution of methyl 3-(3,5-dichlorophenyl)-5,5-dimethyl-4,5,6,7-tetrahydro-1H-4,6-methanoindole-2-carboxylate (0.42 g, 1.16 mmol) in THE (7.8 mL) and MeOH (3.8 mL) was added 2.5 M NaOH (2.3 mL, 5.8 mmol). The resultant mixture was stirred at 50° C. for 48 h. Upon completion, the reaction mixture was acidified to pH 2 with 2 M HCl and extracted with EtOAc (×3). The organic fractions were combined, dried over Na$_2$SO$_4$, filtered and concentrated in vacuo. The residue was purified by flash chromatography (Acetonitrile in DCM, 20-100% and then MeOH in DCM, 5%) to obtain the desired compound.

$^1$H NMR (400 MHz, CDCl$_3$) δ 9.10 (1H, br. s, NH), 7.28 (1H, t, J=1.9 Hz, Ar—CH), 7.21 (2H, d, J=1.9 Hz, Ar—CH), 2.90 (1H, dd, J=16.6, 3.1 Hz, CHH), 2.81 (1H, dd, J=16.6, 2.7 Hz, CHH), 2.71 (1H, app dt, J=9.4, 5.8 Hz, CHH), 2.62 (1H, app t, J=5.4 Hz, CH), 2.39-2.27 (1H, m, CH), 1.38 (3H, s, CH$_3$), 1.35 (1H, d, J=9.5 Hz, CHH), 0.68 (3H, s, CH$_3$); HRMS (TOF, ESI$^-$) m/z: [M–H]$^-$ Calcd for C$_{18}$H$_{16}$O$_2$NCl$_2$ 348.05636; Found 348.05664.

General Procedure E

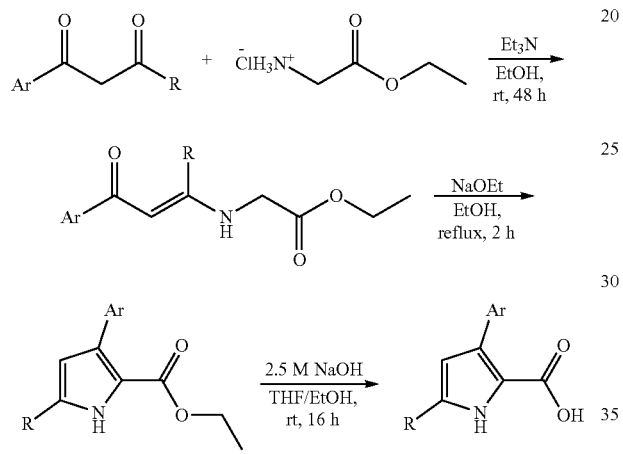

Example 16—5-methyl-3-phenyl-1H-pyrrole-2-carboxylic acid

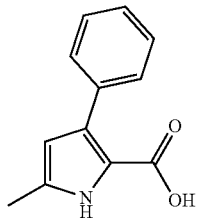

i) Synthesis of ethyl (4-oxo-4-phenylbut-2-en-2-yl)glycinate

To a solution of 1-phenyl-1,3-butanedione (1.0 g, 6.16 mmol) in EtOH (9.2 mL) was added glycine ethyl ester hydrochloride (1.29 g, 9.24 mmol) and Et$_3$N (1.29 mL, 9.24 mmol) and stirred at room temperature for 48 h. The resultant mixture was concentrated in vacuo and the crude was treated with water. The precipitate formed upon the addition of water was isolated by suction filtration, washed with water to remove salts and dried under vacuum to obtain the title compound. $^1$H NMR (400 MHz, CDCl$_3$) δ 11.49 (1H, t, J=6.1 Hz, NH), 7.89-7.82 (2H, m, Ar—CH), 7.44-7.35 (3H, m, Ar—CH), 5.76 (1H, s, —C═CH), 4.23 (2H, q, J=7.1 Hz, CO$_2$CH$_2$CH$_3$), 4.07 (2H, d, J=6.1 Hz, —NHCH$_2$), 2.02 (3H, s, CH$_3$), 1.28 (3H, t, J=7.1 Hz, CO$_2$CH$_2$CH$_3$); HRMS (TOF, ESI$^+$) m/z: [M+H]$^+$ Calcd for C$_{14}$H$_{18}$O$_3$N 248.12812; Found 248.12822.

ii) Synthesis of ethyl 5-methyl-3-phenyl-1H-pyrrole-2-carboxylate

To a solution of NaOEt in EtOH at 50° C. was added ethyl (4-oxo-4-phenylbut-2-en-2-yl)glycinate and the resulting mixture heated to reflux for 2 h. It was then cooled to room temperature and poured into water. The aqueous phase was extracted with EtOAc. The combined organic fractions were dried over Na$_2$SO$_4$, filtered and concentrated in vacuo. The crude residue was purified by flash chromatography (EtOAc in cyclohexane, 0-30%) to obtain the desired compound. $^1$H NMR (400 MHz, CDCl$_3$) δ 9.15 (1H, s, NH), 7.58-7.53 (2H, m, Ar—CH), 7.39-7.33 (2H, m, Ar—CH), 7.31-7.26 (1H, m, Ar—CH), 6.07 (1H, dd, J=3.0, 0.8 Hz, CH), 4.25 (2H, q, J=7.1 Hz, CO$_2$CH$_2$CH$_3$), 2.34 (3H, s, CH$_3$), 1.25 (3H, t, J=7.1 Hz, CO$_2$CH$_2$CH$_3$); HRMS (TOF, ESI$^+$) m/z: [M+Na]$^+$ Calcd for C$_{14}$H$_{15}$O$_2$NNa 252.09950; Found 252.09955.

iii) Synthesis of 5-methyl-3-phenyl-1H-pyrrole-2-carboxylic acid

To a solution of ethyl 5-methyl-3-phenyl-1H-pyrrole-2-carboxylate (0.15 g, 0.66 mmol) in THF (4.4 mL) and EtOH (2.2 mL) was added 2.5 M NaOH (2.1 mL, 5.24 mmol). The resulting mixture was stirred at room temperature for 16 h, then quenched with 2 M HCl and extracted with EtOAc (×2). The organic fractions were combined, dried over Na$_2$SO$_4$, filtered and concentrated in vacuo. The residue was suspended in CH$_2$Cl$_2$ and the resulting precipitate was collected under suction filtration. The precipitate was washed with CH$_2$Cl$_2$ to obtain the desired compound.

$^1$H NMR (400 MHz, DMSO-d$_6$) δ 12.00 (1H, s, NH/OH), 11.45 (1H, s, NH/OH), 7.52-7.47 (2H, m, Ar—CH), 7.34-7.27 (2H, m, Ar—CH), 7.24-7.18 (1H, m, Ar—CH), 5.98 (1H, dd, J=2.7, 0.9 Hz, CH), 2.21 (3H, s, CH$_3$); HRMS (TOF, ESI$^-$) m/z: [M–H]$^-$ Calcd for C$_{12}$H$_{10}$O$_2$N 200.07170; Found 200.07173.

General Procedure F

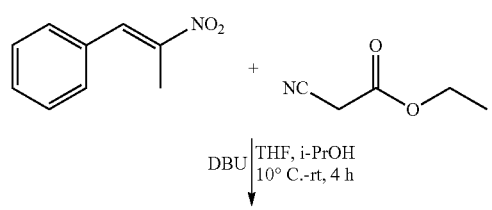

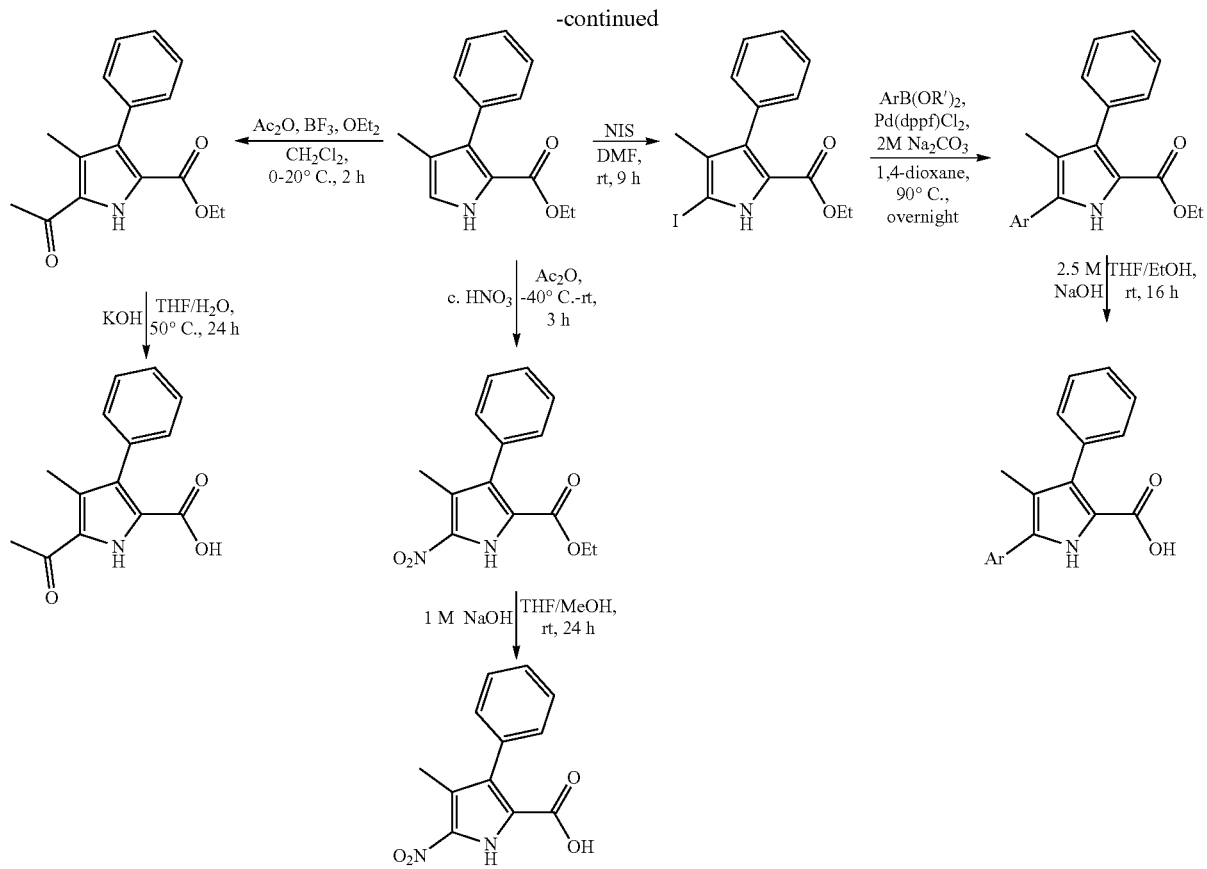

Example 17—4-methyl-3-phenyl-5-(2-(2,2,2-trifluoro-1-hydroxyethyl)phenyl)-1H-pyrrole-2-carboxylic acid

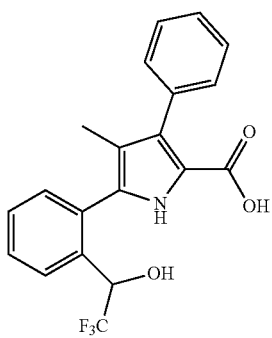 [SMILES: Cc1c(-c2ccccc2C(O)C(F)(F)F)[nH]c(C(=O)O)c1-c1ccccc1]

i) Synthesis of ethyl 4-methyl-3-phenyl-H-pyrrole-2-carboxylate

To a stirred solution of ethyl isocyanate (1.0 g, 6.13 mmol) and trans-β-methyl-β-nitrostyrene (0.74 mL, 6.74 mmol) in THF (7.4 mL) and i-PrOH (2.5 mL) was added DBU (1.83 mL, 12.26 mmol) while maintaining the reaction temperature between 10-20° C. The reaction mixture was then left to stir at room temperature for 4 h. The resulting mixture was concentrated in vacuo and the crude was treated with water and extracted with Et$_2$O. The combined organic fractions were dried over Na$_2$SO$_4$, filtered and concentrated in vacuo. The crude residue was purified by flash chromatography (EtOAc in cyclohexane, 0-20%) to obtain the desired compound.

$^1$H NMR (400 MHz, CDCl$_3$) δ 9.11 (1H, br. s, NH), 7.42-7.28 (5H, m, Ar—CH), 6.78 (1H, dd, J=2.9, 0.9 Hz, Ar—CH), 4.17 (2H, q, J=7.1 Hz, CO$_2$CH$_2$CH$_3$), 2.01 (3H, d, J=0.9 Hz, CH$_3$), 1.14 (3H, t, J=7.1 Hz, CO$_2$CH$_2$CH$_3$); HRMS (APCI$^+$) m/z: [M+H]$^+$ Calcd for C$_{14}$H$_{15}$O$_2$N 229.10973; Found 229.10922.

ii) Synthesis of ethyl 5-iodo-4-methyl-3-phenyl-1H-pyrrole-2-carboxylate

To a solution of ethyl 4-methyl-3-phenyl-1H-pyrrole-2-carboxylate (0.35 g, 1.53 mmol) in DMF (5 mL) was added N-iodosuccinamide (0.38 g, 1.68 mmol). The resulting mixture was stirred at room temperature for 9 h and then diluted with CH$_2$Cl$_2$ and sat. NaHCO$_3$. The aqueous phase was re-extracted with CH$_2$Cl$_2$ and the combined organic extracts were dried over Na$_2$SO$_4$, filtered and concentrated in vacuo. The residue was purified by flash chromatography (EtOAc in cyclohexane, 0-20%) to obtain the desired compound.

$^1$H NMR (400 MHz, CDCl$_3$) δ 9.51 (1H, br. s, NH), 7.41-7.28 (5H, m, Ar—CH), 4.19 (2H, q, J=7.1 Hz, CO$_2$CH$_2$CH$_3$), 1.94 (3H, s, CH$_3$), 1.12 (3H, t, J=7.1 Hz, CO$_2$CH$_2$CH$_3$); HRMS (TOF, ESI$^+$) m/z: [M+Na]$^+$ Calcd for C$_{14}$H$_{14}$O$_2$NINa 377.99614; Found 377.99635.

iii) Synthesis of ethyl 4-methyl-3-phenyl-5-(2-(2,2,2-trifluoroacetyl)phenyl)-1H-pyrrole-2-carboxylate A mixture of ethyl 5-iodo-4-methyl-3-phenyl-1H-pyrrole-2-carboxylate (100 mg, 1 eq), 2,2,2-trifluoro-1-(2-(4,4,5,5- tetramethyl-1,3,2-dioxaborolan-2-yl)phenyl)ethan-1-one (1.5 eq), Cs$_2$CO$_3$ (2 eq) in DMF was purged with argon and treated with Pd(dppf)Cl$_2$ (5 mol %). After treating with the catalyst, the reaction mixture was purged with argon and then heated at 100° C. for 6 h. The resultant mixture was filtered through decalite, rinsing with EtOAc. The filtrate was concentrated in vacuo and purified by flash chromatography (EtOAc in cyclohexane) to obtain the desired compound. HRMS (TOF, ESI$^+$) m/z: [M+H]$^+$ Calcd for C$_{22}$H$_{19}$O$_3$NF$_3$ 402.13115; Found 402.13116.

iv) Synthesis of 4-methyl-3-phenyl-5-(2-(2,2,2-trifluoro-1-hydroxyethyl)phenyl)-1H-pyrrole-2-carboxylic acid To a solution of ethyl 4-methyl-3-phenyl-5-(2-(2,2,2-trifluoroacetyl)phenyl)-1H-pyrrole-2-carboxylate (1 eq) in MeOH/H$_2$O was added NaOH (16 eq). The resultant mixture was stirred at room temperature for 24 h. The mixture was quenched with 1M HCl and extracted with EtOAc (×2). The organic fractions were combined, dried over Na$_2$SO$_4$, filtered and concentrated in vacuo. The crude residue was purified by flash column chromatography eluting with DCM-10% MeOH to obtain the desired compound.

$^1$H NMR (400 MHz, DMSO-d$_6$) δ 11.68 (1H, br. s, NH), 7.83-7.22 (9H, m, Ar—CH), 5.22 (1H, q, J=7.4 Hz, CF$_3$CH), 1.98 (3H, s, CH$_3$); HRMS (TOF, ESI$^+$) m/z: [M+H]$^+$ Calcd for C$_{20}$H$_{17}$O$_3$NF$_3$ 376.11550; Found 376.11570.

Example 18—4-methyl-3-phenyl-5-(3-(2,2,2-trifluoro-1-hydroxyethyl)phenyl)-1H-pyrrole-2-carboxylic acid

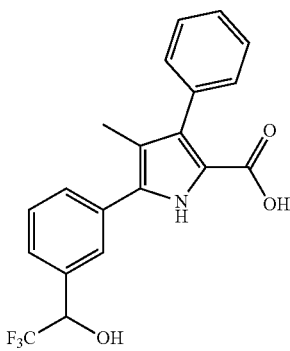 [SMILES: Cc1c(-c2cccc(C(O)C(F)(F)F)c2)[nH]c(C(=O)O)c1-c1ccccc1]

Same procedure as for Example 13. HRMS (TOF, ESI$^+$) m/z: [M+H]$^+$ Calcd for C$_{20}$H$_{17}$O$_3$NF$_3$ 376.11550; Found 376.11584.

Example 19—4-methyl-5-nitro-3-phenyl-1H-pyrrole-2-carboxylic acid

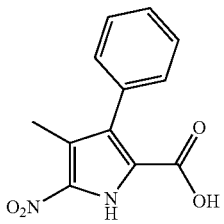 [SMILES: Cc1c([N+](=O)[O-])[nH]c(C(=O)O)c1-c1ccccc1]

i) Synthesis of ethyl 4-methyl-5-nitro-3-phenyl-1H-pyrrole-2-carboxylate

A solution of ethyl 4-methyl-3-phenyl-1H-pyrrole-2-carboxylate (100 mg, 0.44 mmol) was dissolved in acetic anhydride and cooled to −40° C. Concentrated nitric acid (1.5 eq) was added dropwise. The reaction mixture was stirred for 3 h while allowing it to slowly warm to r.t. After 3 h, the mixture was cooled to −40° C. again, poured over an ice-water mixture, and filtered to obtain the precipitate. The precipitate was washed with water, re-dissolved in EtOAc and concentrated in vacuo to give the desired compound.

$^1$H NMR (400 MHz, CDCl$_3$) 10.32 (1H, br. s, NH), 7.42-7.38 (3H, m, Ar—CH), 7.29-7.24 (2H, m, Ar—CH), 4.23 (2H, q, J=7.1 Hz, CH$_2$CH$_3$), 2.30 (3H, s, CH$_3$), 1.13 (3H, t, J=7.1 Hz, CH$_2$CH$_3$); LCMS [M+H]+ 275.1.

ii) Synthesis of 4-methyl-5-nitro-3-phenyl-1H-pyrrole-2-carboxylic acid

A solution of ethyl 4-methyl-5-nitro-3-phenyl-1H-pyrrole-2-carboxylate (30 mg, 0.14 mmol) was dissolved in THF/MeOH (3:1, 4 mL) and 1M aqueous NaOH solution (0.71 mL, 0.71 mmol, 5.0 equiv.) was added slowly. The reaction mixture was left to stir at room temperature for 24 h, after which it was diluted with 1M NaOH solution (10 mL) and washed with ethyl acetate (20 mL). The aqueous layer was acidified with 2M HCl solution (10 mL) and extracted with ethyl acetate (20 mL). The resultant organic layer was dried over Na$_2$SO$_4$, filtered, and concentrated in vacuo to give a white solid. The precipitate was washed with water, re-dissolved in EtOAc and concentrated in vacuo to give the desired compound.

$^1$H NMR (400 MHz, CD$_3$OD) δ 7.41-7.31 (3H, m, Ar—CH), 7.28-7.24 (2H, m, Ar—CH), 2.22 (3H, s, CH$_3$); HRMS (TOF, ESI$^-$) m/z: [M−H]$^-$ Calcd for C$_{12}$H$_9$O$_4$N$_2$ 245.0568; Found 245.0567.

Example 20—5-acetyl-4-methyl-3-phenyl-1H-pyrrole-2-carboxylic acid

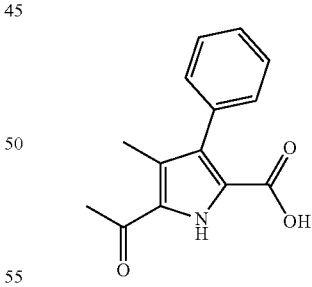

i) Synthesis of ethyl 5-acetyl-4-methyl-3-phenyl-1H-pyrrole-2-carboxylate

To a solution of acetic anhydride (0.17 mL, 1.74 mmol) in CH$_2$Cl$_2$ (5 mL) at 0° C., BF$_3$.OEt$_2$ (0.16 mL, 1.31 mmol) was added drop-wise and stirred at 0° C. for 10 min. To the resultant mixture, ethyl 4-methyl-3-phenyl-1H-pyrrole-2-carboxylate (200 mg, 0.87 mmol) was added in portions and stirred at 0° C. for 30 min, then at room temperature for 2 h. The reaction mixture was poured into water and extracted with CH$_2$Cl$_2$. The organic fractions were washed with saturated NaHCO$_3$, dried over Na$_2$SO$_4$, filtered and concentrated in vacuo. The residue obtained was purified by flash column chromatography eluting with EtOAc in cyclohexane (0-20%) to give the desired compound.

$^1$H NMR (400 MHz, CDCl) δ 9.81 (1H, br. s, NH), 7.43-7.30 (3H, m, Ar—CH), 7.30-7.23 (2H, m, Ar—CH), 4.18 (2H, q, J=7.1 Hz, CH$_2$CH$_3$), 2.54 (3H, s, C(O)CH$_3$), 2.24 (3H, s, CH$_3$), 1.14 (3H, t, J=7.1 Hz, CH$_2$CH$_3$); HRMS (TOF, ESI$^+$) m/z: [M+H]$^+$ Calcd for C$_{16}$H$_{18}$O$_3$N 272.12812; Found 272.12794.

ii) Synthesis of 5-acetyl-4-methyl-3-phenyl-1H-pyrrole-2-carboxylic acid

To a stirred solution of ethyl 5-acetyl-4-methyl-3-phenyl-1H-pyrrole-2-carboxylate (200 mg, 0.74 mmol) in THF/H$_2$O (1:2, 7 mL) was added KOH (0.16 g, 2.95 mmol) and the resultant mixture heated at 50° C. for 24 h. Upon completion, the reaction mixture was cooled to room temperature and acidified to pH 1 with 2M HCl. The product was extracted with EtOAc (×3) and the combined organic extracts were dried over Na$_2$SO$_4$, filtered, and concentrated in vacuo. The crude residue was purified by flash column chromatography eluting with MeOH in CH$_2$Cl$_2$ (0-8%) to give the desired compound.

$^1$H NMR (400 MHz, CD30D) δ 9.97 (1H, br. s, NH), 7.37-7.06 (5H, m, Ar—CH), 2.43 (3H, s, C(O)CH$_3$), 2.12 (3H, s, CH$_3$); HRMS (TOF, ESI$^+$) m/z: [M+H]$^+$ Calcd for C$_{14}$H$_{14}$O$_3$N 244.09682; Found 244.09686.

Example 21—5-acetyl-1,4-dimethyl-3-phenyl-1H-pyrrole-2-carboxylic acid

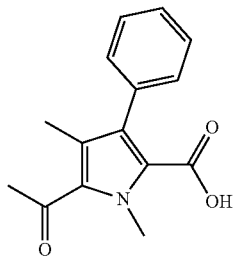 [SMILES: CC(=O)c1c(C)c(-c2ccccc2)c(C(=O)O)n1C]

i) Synthesis of ethyl 1,4-dimethyl-3-phenyl-1H-pyrrole-2-carboxylate

To a stirred suspension of ethyl 4-methyl-3-phenyl-1H-pyrrole-2-carboxylate (250 mg, 1.09 mmol) and K$_2$CO$_3$ (300 mg, 2.18 mmol) in DMF/1,4-dioxane (1:1, 4 mL) was added MeI (0.48 mL, 7.64 mmol) and resultant mixture was heated at 90° C. for 7 h. The reaction mixture was cooled to room temperature, treated with water and extracted with EtOAc (×2). The combined organic extracts were dried over Na$_2$SO$_4$, filtered and concentrated in vacuo. The residue obtained was purified by flash column chromatography eluting with EtOAc in cyclohexane (0-10%) to give the desired compound.

$^1$H NMR (400 MHz, CDCl$_3$) δ 7.39-7.32 (2H, m, Ar—CH), 7.31-7.22 (3H, m, Ar—CH), 6.62 (1H, d, J=0.9 Hz, Ar—CH), 4.03 (2H, q, J=7.1 Hz, CH$_2$CH$_3$), 3.90 (3H, s, NCH$_3$), 1.92 (3H, d, J=0.9 Hz, CH$_3$), 0.94 (3H, t, J=7.1 Hz, CH$_2$CH$_3$); HRMS (TOF, ESI) m/z: [M+H]$^+$ Calcd for C$_{15}$H$_{18}$O$_2$N 244.13321; Found 244.13343.

ii) Synthesis of ethyl 5-acetyl-1,4-dimethyl-3-phenyl-1H-pyrrole-2-carboxylate

To a solution of acetic anhydride (0.16 mL, 1.65 mmol) in CH$_2$Cl$_2$ (5 mL) at 0° C., BF$_3$.OEt$_2$ (0.15 mL, 1.23 mmol) was added drop-wise and stirred at 0° C. for 10 min. To the resultant mixture, ethyl 1,4-dimethyl-3-phenyl-1H-pyrrole-2-carboxylate (200 mg, 0.82 mmol) was added in portions and stirred at 0° C. for 30 min, then at room temperature for 2 h. The reaction mixture was poured into water and extracted with CH$_2$Cl$_2$. The organic fractions were washed with saturated NaHCO$_3$, dried over Na$_2$SO$_4$, filtered and concentrated in vacuo. The residue obtained was purified by flash column chromatography eluting with EtOAc in cyclohexane (0-20%) to give the desired compound.

$^1$H NMR (400 MHz, CDCl$_3$) δ 7.42-7.28 (3H, m, Ar—CH), 7.18-7.13 (2H, m, Ar—CH), 4.08 (3H, s, NCH$_3$), 4.01 (2H, q, J=7.1 Hz, CH$_2$CH$_3$), 2.54 (3H, s, C(O)CH$_3$), 2.15 (3H, s, CH$_3$), 0.86 (3H, t, J=7.1 Hz, CH$_2$CH$_3$); HRMS (APCI$^+$) m/z: [M+H]$^+$ Calcd for C$_{17}$H$_{20}$O$_3$N 286.14377; Found 286.14375.

iii) Synthesis of 5-acetyl-1,4-dimethyl-3-phenyl-1H-pyrrole-2-carboxylicacid

To a stirred solution of ethyl 5-acetyl-1,4-dimethyl-3-phenyl-1H-pyrrole-2-carboxylate (200 mg, 0.70 mmol) in THF/H$_2$O (1:2, 9 mL) was added KOH (0.16 g, 2.8 mmol) and the resultant mixture heated at 50° C. for 24 h. Upon completion, the reaction mixture was cooled to room temperature and acidified to pH 1 with 2M HCl. The product was extracted with EtOAc (×3) and the combined organic extracts were dried over Na$_2$SO$_4$, filtered, and concentrated in vacuo. The crude residue was purified by flash column chromatography eluting with MeOH in CH$_2$Cl$_2$ (0-10%) to give the desired compound.

$^1$H NMR (400 MHz, DMSO-d$_6$) δ 7.41-7.35 (2H, m, Ar—CH), 7.34-7.27 (1H, m, Ar—CH), 7.20-7.14 (2H, m, Ar—CH), 3.93 (3H, s, NCH$_3$), 2.50 (3H, s, C(O)CH$_3$, obscured by DMSO), 2.08 (3H, s, CH$_3$); HRMS (TOF, ESI$^-$) m/z: [M–H]$^-$ Calcd for C$_{15}$H$_{14}$O$_3$N 256.09792; Found 256.09781.

General Procedure G1

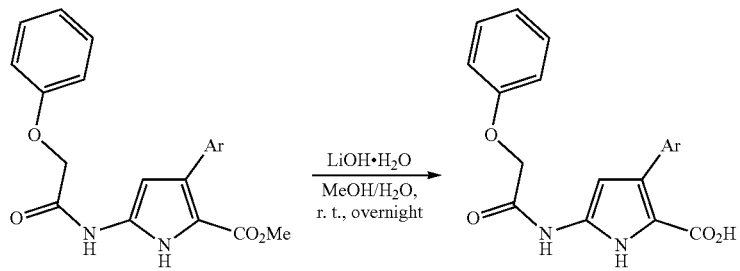

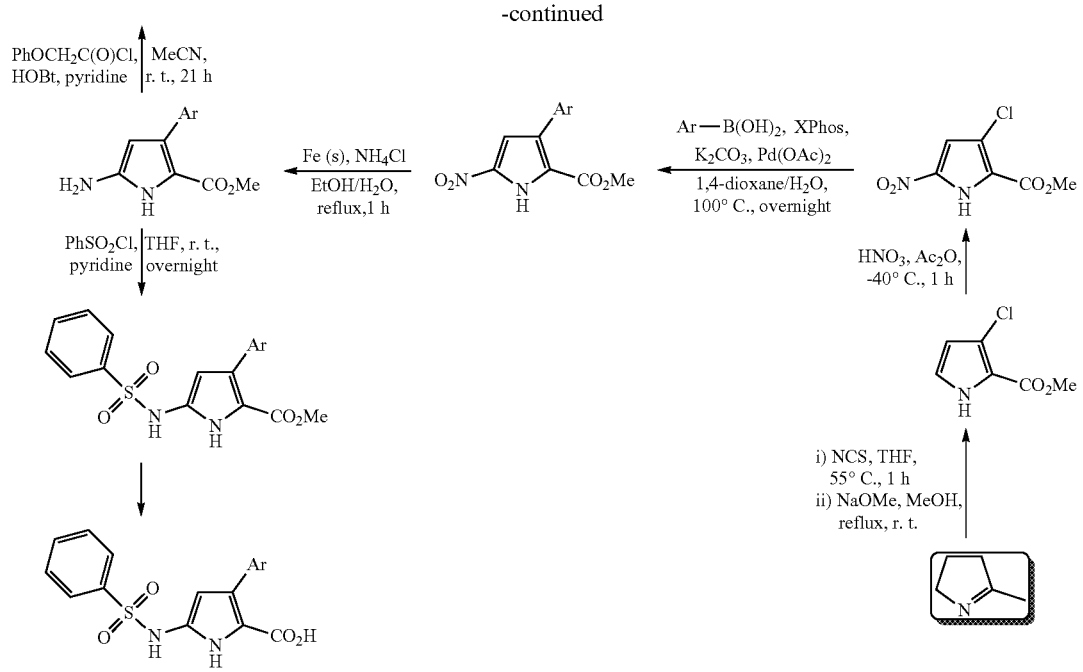
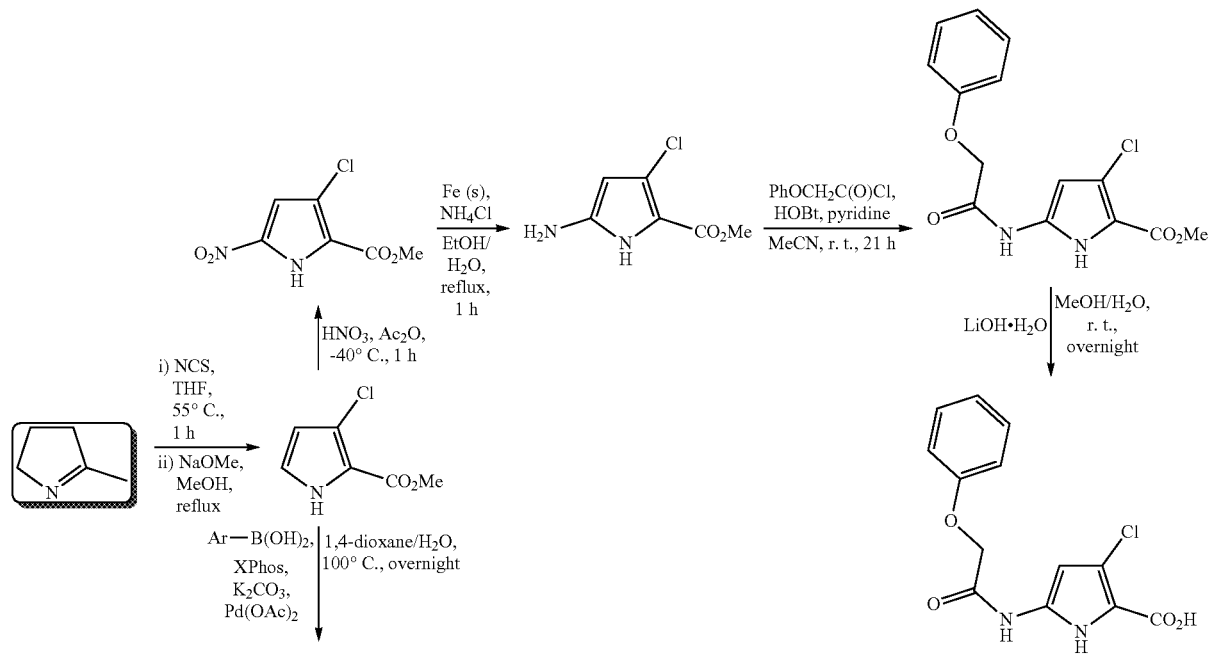
General Procedure G2
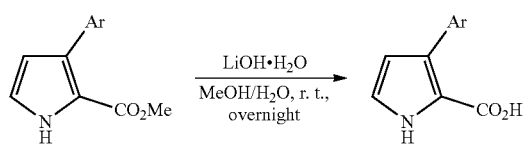

Example 22—3-(4-fluorophenyl)-5-(phenylsulfonamido)-1H-pyrrole-2-carboxylic acid i) Synthesis of methyl 3-chloro-1H-pyrrole-2-carboxyate

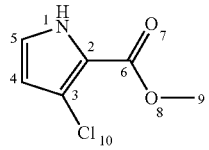

2-Methyl-1-pyrroline (2.0 mL, 21.1 mmol, 1.0 eq) was dissolved in THF (60 mL) and ice-cooled. NCS (22.56 g, 169 mmol, 8.0 eq) was added and the reaction mixture was stirred at 55° C. for 1 h. Upon completion, the reaction mixture was diluted with water (30 mL) and extracted with cyclohexane (4×30 mL). The combined organic layers were dried over anhydrous sodium sulfate, filtered and concentrated in vacuo to yield intermediate compound (8.79 g, crude) as a brown oil, which was used directly for the next step without further purification.

The intermediate compound was dissolved in MeOH (25 mL) and ice-cooled. 28% NaOMe/MeOH solution (38 mL) was added dropwise, and the reaction mixture was left to stir for 2 h at r.t. At the end of the reaction, the mixture was cooled using ice, and 4M sulfuric acid solution was added slowly to neutralise the mixture. The mixture was then concentrated under reduced pressure and the concentrated mixture was extracted with EtOAc (5×30 mL). The combined organic layers were washed with brine (50 mL), dried over anhydrous sodium sulfate, filtered and concentrated in vacuo. The concentrate was further purified by flash column chromatography on silica (eluted with cyclohexane-EtOAc) to afford the desired compound (1.87 g, 11.7, 55%) as a brown solid.

Mp 86.2-87.0° C. (lit. 88.3-90.3° C.); TLC 3:2 Cyclohexane/EtOAc, $R_f$=0.50; IR $v_{max}$ (film)/cm$^{-1}$ 3399, 3131, 2957, 1670, 1535, 1439, 1398, 1314, 1215, 1106, 1021; $^1$H NMR (400 MHz, DMSO-d$_6$) δ 12.11 (1H, s, H1), 7.02 (1H, dd, J=3.5, 2.8 Hz, H5), 6.25 (1H, t, J=2.7 Hz, H4), 3.78 (3H, s, H9); $^{13}$C NMR (101 MHz, DMSO-d$_6$) δ 159.6, 123.3, 117.4, 117.2, 110.9, 51.2; HRMS (TOF, ESI$^-$) m/z: [M-H]$^-$ Calcd for C$_6$H$_5$ClNO$_2$ 158.00143; Found 158.0008.

ii) Synthesis of methyl 3-chloro-5-nitro-1H-pyrrole-2-carboxylate and methyl 3-chloro-4-nitro-1H-pyrrole-2-carboxylate Methyl 3-chloro-1H-pyrrole-2-carboxylate (1.87 g, 11.7 mmol, 1.0 eq) was dissolved in acetic anhydride (20 mL) and cooled to −40° C. Concentrated nitric acid (1.1 mL, 17.3 mmol, 1.5 equiv.) was added dropwise. The reaction mixture was stirred for 3 h while allowing it to slowly warm to r.t. After 3 h, the mixture was cooled to −40° C. again, poured over an ice-water mixture, and filtered to obtain the precipitate. The precipitate was washed with water, re-dissolved in EtOAc and concentrated in vacuo to give a yellow solid containing a mixture of regioisomers (0.98 g, 4.79 mmol, 40%).

The mixture of regioisomers was separated using flash column chromatography (eluted with cyclohexane-EtOAc) to afford methyl 3-chloro-5-nitro-1H-pyrrole-2-carboxylate (451 mg, 2.20 mmol) and methyl 3-chloro-4-nitro-1H-pyrrole-2-carboxylate (533 mg, 2.61 mmol) in the ratio of 46% to 54% respectively.

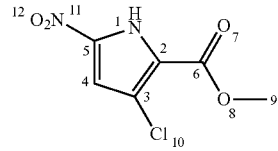

Mp 180.2-184.4° C.; TLC 4:1 Cyclohexane/EtOAc, $R_f$=0.35; IR $v_{max}$ (film)/cm$^{-1}$ 3208, 3137, 1695, 1517, 1467, 1413, 1370, 1289, 1256, 1084, 1050; $^1$H NMR (400 MHz, Chloroform-d) δ 10.32 (1H, s, H1), 7.05 (1H, s, H5), 3.98 (3H, s, H9); 13C NMR (101 MHz, Chloroform-d) b 159.3, 136.9, 121.2, 119.4, 111.1, 53.1; LRMS (ESI$^+$, m/z) 205.1 [M+H]; HRMS (TOF, ESI$^-$) m/z: [M-H]$^-$ Calcd for C$_6$H$_4$ClN$_2$O$_4$ 202.9865; Found 202.9860.

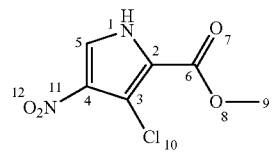

Mp 230.6-233.1° C.; TLC 4:1 Cyclohexane/EtOAc, $R_f$=0.20; IR $v_{max}$ (film)/cm 3246, 3148, 1682, 1548, 1504, 1442, 1374, 1313, 1260, 1209, 1125, 1067; $^1$H NMR (400 MHz, DMSO-d$_6$) δ 13.45 (1H, s, H1), 8.19 (1H, s, H4), 3.85 (3H, s, H9); $^{13}$C NMR (101 MHz, Chloroform-d$_6$) δ 159.2, 131.8, 123.8, 119.4, 114.5, 53.0; LRMS (ESI$^+$, m/z) 205.0 [M+H]; HRMS (TOF, ESI$^-$) m/z: [M-H]$^-$ Calcd for C$_6$H$_4$ClN$_2$O$_4$ 202.9865; Found 202.9860.

iii) Synthesis of methyl 5-amino-3-chloro-1H-pyrrole-2-carboxylate

A mixture of ammonium chloride (53 mg, 0.99 mmol, 0.7 equiv.) and iron (432 mg, 7.74 mmol, 5.5 equiv.) was suspended in a mixture of EtOH and water (15 mL, v/v=10:1), and heated to reflux for 5 min. Methyl 3-chloro-5-nitro-1H-pyrrole-2-carboxylate (288 mg, 1.41 mmol, 1.0 equiv.) was added and the mixture was allowed to stir for 1 h. Upon completion, the mixture was allowed to cool to r.t. and concentrated in vacuo. The concentrate was re-dissolved in CH$_2$Cl$_2$ and filtered through a Celite™ pad with thorough washing with CH$_2$Cl$_2$. Finally, the filtrate was concentrated under reduced pressure to afford the desired compound (240 mg, 1.37 mmol, 98%) as a yellow solid, which was used for subsequent steps without further purification.

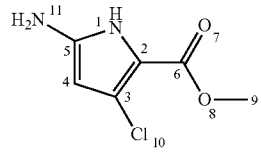

iv) Synthesis of methyl 3-(4-fluorophenyl)-5-nitro-1H-pyrrole-2-carboxylate

A mixture of methyl 3-chloro-5-nitro-1H-pyrrole-2-carboxylate (2.98 g, 14.6 mmol, 1.0 equiv.), 4-fluorophenylboronic acid (4.19 g, 17.5 mmol, 1.2 equiv.), palladium(II) acetate (327 mg, 1.46 mmol, 10 mol. %), XPhos (1.39 g, 2.92 mmol, 20 mol. %) and potassium carbonate (6.04 g, 43.7 mmol, 3.0 equiv.) was dissolved in a mixture of 1,4-dioxane and water (100 mL, v/v=5:1). The mixture was purged with $N_2$ for 30 min and stirred at reflux overnight. Upon completion, the mixture was allowed to cool to r.t. and filtered through a Celite™ pad with thorough washing with $CH_2Cl_2$. The filtrate was concentrated in vacuo and purified via flash column chromatography (eluted with cyclohexane-EtOAc) to afford the desired compound (2.79 g, 72%).

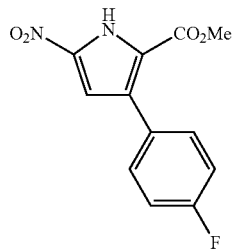 [SMILES: COC(=O)c1[nH]c([N+](=O)[O-])cc1-c1ccc(F)cc1]

v) Synthesis of methyl 5-amino-3-(4-fluorophenyl)-1H-pyrrole-2-carboxylate

Synthesis of the desired compound was achieved (2.45 g, 99%) as per the procedure used to synthesise methyl 5-amino-3-chloro-1H-pyrrole-2-carboxylate, using methyl 3-(4-fluorophenyl)-5-nitro-1H-pyrrole-2-carboxylate as the starting material (2.79 g, 10.6 mmol, 1.0 equiv.).

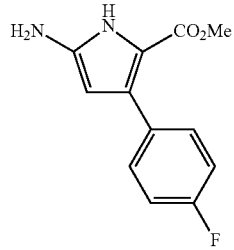 [SMILES: COC(=O)c1[nH]c(N)cc1-c1ccc(F)cc1]

vi) Synthesis of methyl 3-(4-fluorophenyl)-5-(phenylsulfonamido)-1H-pyrrole-2-carboxylate A mixture of methyl 5-amino-3-(4-fluorophenyl)-1H-pyrrole-2-carboxylate (220 mg, 0.939 mmol, 1.0 equiv.), and pyridine (0.20 mL, 2.48 mmol, 2.5 equiv.) were dissolved in tetrahydrofuran (4.0 mL). Benzenesulfonyl chloride (0.16 mL, 1.25 mmol, 1.2 equiv.) was added dropwise and the resultant mixture was stirred at r.t. overnight. Upon completion, the mixture was concentrated under reduced pressure and purified by flash column chromatography (eluted with cyclohexane-EtOAc) to afford the desired product.

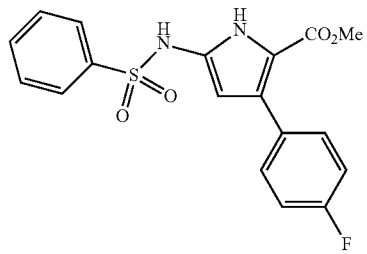 [SMILES: COC(=O)c1[nH]c(NS(=O)(=O)c2ccccc2)cc1-c1ccc(F)cc1]

$^1$H NMR (400 MHz, Chloroform-d) δ 9.36 (s, 1H), 7.77 (dd, J=8.5, 1.2 Hz, 2H), 7.62 (t, J=7.5 Hz, 1H), 7.51 (t, J=7.7 Hz, 2H), 7.39 (dd, J=8.9, 5.4 Hz, 2H), 7.01 (t, J=8.8 Hz, 2H), 6.65 (s, 1H), 5.64 (d, J=3.1 Hz, 1H), 3.79 (s, 3H); LCMS m/z 375.1 (M+H$^+$), time=7.461.

Example 23—3-chloro-5-(2-phenoxyacetamido)-1H-pyrrole-2-carboxylic acid

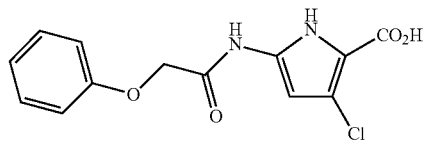 [SMILES: O=C(COc1ccccc1)Nc1cc(Cl)c(C(=O)O)[nH]1]

i) Synthesis of methyl 3-chloro-5-(2-phenoxyacetamido)-1H-pyrrole-2-carboxylate HOBt (1.05 g, 6.86 mmol, 5.0 eq) dissolved in dry pyridine (3.4 mL) was added to methyl 5-amino-3-chloro-1H-pyrrole-2-carboxylate (240 mg, 1.37 mmol, 1.0 eq) dissolved in dry acetonitrile (14 mL). 2-Phenoxyacetyl chloride (0.95 mL, 6.88 mmol, 5.0 eq) was then added slowly. The reaction mixture was stirred at r.t. under $N_2$ for 21 h. At the end of the reaction, the mixture was diluted with chloroform, washed with saturated sodium bicarbonate solution (50 mL) and brine (50 mL). The organic layer was dried over anhydrous sodium sulfate, filtered and concentrated in vacuo. The resultant crude product was purified using flash column chromatography (eluted with cyclohexane-EtOAc) to afford the desired compound (219 mg, 0.709 mmol, 52%) as a pale yellow solid.

$^1$H NMR (400 MHz, Chloroform-d) 10.86 (s, 1H), 8.42 (s, 1H), 7.67 (d, J=3.2 Hz, 1H), 7.06 (t, J=7.4 Hz, 2H), 7.01 (d, J=7.9 Hz, 2H) 6.93 (d, J=7.9 Hz, 1H), 4.65 (s, 2H), 3.91 (s, 3H); HRMS (TOF, ESI$^+$) m/z: [M+Na]$^+$ Calcd for $C_{14}H_{13}ClN_2O_4Na$ 331.0456; Found 331.0456.

ii) Synthesis of 3-chloro-5-(2-phenoxyacetamido)-1H-pyrrole-2-carboxylic acid Methyl 3-chloro-5-(2-phenoxyacetamido)-1H-pyrrole-2-carboxylate (49 mg, 0.16 mmol, 1.0 eq) was dissolved in a mixture of MeOH and water (v/v=2:1, 3 mL). The mixture was cooled to 0° C. and lithium hydroxide monohydrate (27 mg, 0.63 mmol, 4.0 eq) was added. The mixture was stirred for 24 h at 50° C. The methanol was concentrated under reduced pressure, and the aqueous residue was diluted with water and extracted with EtOAc (2×10 mL). The aqueous phase was adjusted to pH 3-4 with 1M HCl solution, and the desired compound (43 mg, 0.15 mmol, 94%) was filtered out as a white solid.

$^1$H NMR (400 MHz, Chloroform-d) δ 10.87 (s, 1H), 9.33 (br. s, 1H), 8.43 (s, 1H), 7.67 (d, J=3.4 Hz, 1H), 7.06 (t, J=7.4 Hz, 2H), 7.00 (d, J=8.0 Hz, 2H), 6.93 (d, J=8.0 Hz, 1H), 4.65 (s, 2H); HRMS (TOF, ESI$^+$) m/z: [M+H]$^+$ Calcd for $C_{13}H_{12}ClN_2O_4$ 295.0480; Found 295.0481.

Example 24—5-(2-phenoxyacetamido)-3-phenyl-1H-pyrrole-2-carboxylic acid

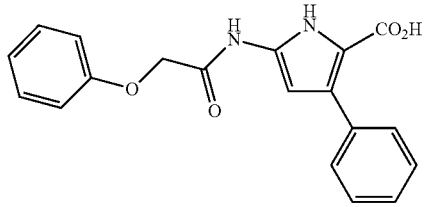 [SMILES: O=C(COc1ccccc1)Nc1cc(-c2ccccc2)c(C(=O)O)[nH]1]

i) Synthesis of methyl 5-(2-phenoxyacetamido)-3-phenyl-1H-pyrrole-2-carboxylate

Methyl 3-chloro-5-(2-phenoxyacetamido)-1H-pyrrole-2-carboxylate (50 mg, 0.16 mmol, 1.0 eq) and phenylboronic acid (35 mg, 0.29 mmol, 1.8 eq) were added to a mixture of 1,4-dioxane and water (v/v=5:1, 2.4 mL) in a microwave vial. With stirring, XPhos (32 mg, 0.067 mmol, 0.4 eq), palladium (II) acetate (11 mg, 0.049 mmol, 0.3 eq) and potassium carbonate (70 mg, 0.51 mmol, 3.0 eq) were added. The suspension was purged with $N_2$ for 5 min, after which the reaction mixture was stirred at 100° C. for 48 h. Upon completion, the mixture was cooled to ambient temperature and diluted with water. The mixture was extracted with EtOAc (4×10 mL) and the combined organic fractions were washed with brine, dried over anhydrous sodium sulfate and concentrated under reduced pressure. The crude material was purified using flash column chromatography (eluted with cyclohexane-EtOAc) and concentrated in vacuo to afford the desired compound as a dark brown solid, which was used immediately for the subsequent step.

ii) Synthesis of 5-(2-phenoxyacetamido)-3-phenyl-1H-pyrrole-2-carboxylic acid

The desired compound was obtained from the hydrolysis of methyl 5-(2-phenoxyacetamido)-3-phenyl-1H-pyrrole-2-carboxylate following the procedure for example 23 (38 mg, 0.11 mmol, 71% over 2 steps).

$^1$H NMR (400 MHz, Chloroform-d) δ 9.86 (s, 1H), 9.61 (br. s, 1H), 8.60 (s, 1H), 8.02 (d, J=2.7 Hz, 1H), 7.90-8.07 (m, 5H), 7.28-7.35 (m, 2H), 7.17 (d, J=8.1 Hz, 1H), 7.03 (d, J=8.4 Hz, 2H), 4.83 (s, 2H); HRMS (TOF, ESI$^+$) m/z: [M+H]$^+$ Calcd for $C_{19}H_{15}N_2O_4$ 335.1037; Found 335.1041.

Further Compounds Synthesised Under this Series

| Example Number | Structure |
| --- | --- |
| 25 | 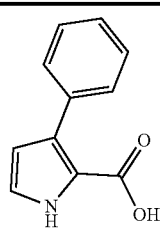 |
| 26 | |
| 27 | |

(table continued)

| Example Number | Structure |
| --- | --- |
| 26 | 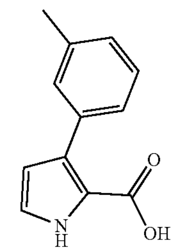 |
| 27 | 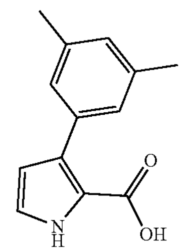 [SMILES: Cc1cc(C)cc(-c2cc[nH]c2C(=O)O)c1] |

Procedure for the Synthesis of Imidazole Derivatives

Example 28—2,4-dibromo-1H-imidazole-5-carboxylic acid

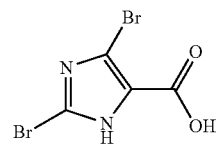

i) Synthesis of ethyl 2,4-dibromo-1H-imidazole-5-carboxylate

To a solution of ethyl 1H-imidazole-5-carboxylate (0.6 g, 4.28 mmol) in acetonitrile was added N-bromosuccinamide (1.68 g, 9.42 mmol) and the reaction mixture was stirred at 70° C. for 4 h. The resultant mixture was then concentrated in vacuo and purified by flash chromatography (EtOAc/cyclohexane) to obtain the desired compound. $^1$H NMR (400 MHz, CDCl$_3$) δ 11.89 (1H, s, NH), 4.44-4.37 (2H, m, $CO_2CH_2CH_3$), 1.44-1.35 (3H, m, $CO_2CH_2CH_3$); HRMS (TOF, ESI$^+$) m/z: [M+H]$^+$ Calcd for $C_6H_6O_2N_2NaBr_2$ 320.8673; Found 320.8673.

ii) Synthesis of 2,4-dibromo-1H-imidazole-5-carboxylic acid

To a solution of ethyl 2,4-dibromo-1H-imidazole-5-carboxylate (0.15 g, 0.5 mmol) in THF (3.4 mL) and EtOH (1.7 mL) was added 2.5 M NaOH (1.62 mL, 4.03 mmol) and the reaction mixture was heated under reflux overnight. The resultant mixture was quenched with 2 M HCl and concentrated in vacuo. The residue was suspended in $CH_2Cl_2$ and the resultant precipitate was collected under suction filtration. The precipitate was washed with $CH_2Cl_2$ followed by water to obtain the desired compound.

HRMS (TOF, ESI⁻) m/z: [M−H]⁻ Calcd for $C_4HO_2N_2Br_2$ 268.8384; Found 268.8300.

Example 29—2,4-bis(4-fluorophenyl)-1H-imidazole-5-carboxylic acid

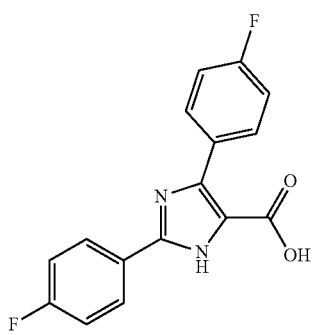 [SMILES: O=C(O)c1[nH]c(-c2ccc(F)cc2)nc1-c1ccc(F)cc1]

i) Synthesis of ethyl 2,4-bis(4-fluorophenyl)-1H-imidazole-5-carboxylate

A mixture of ethyl 2,4-dibromo-1H-imidazole-5-carboxylate (0.15 g, 0.50 mmol), 4-fluorophenylboronic acid (0.16 g, 1.1 mmol), 2M $Na_2CO_3$ (2.0 mL, 4.0 mmol) in 1,4-dioxane (4.5 mL) was purged with argon and treated with Pd(dppf)Cl₂ (15 mg, 0.02 mmol). After treating with the catalyst, the reaction mixture was purged with argon and subjected to μW irradiation at 110° C. for 1 h. The resultant mixture was filtered through decalite, rinsing with EtOAc and water. The filtrate was partitioned between 1 M HCl and EtOAc. The aqueous phase was extracted with EtOAc and the organic extracts were dried over $Na_2SO_4$, filtered and concentrated in vacuo. The residue was purified by flash chromatography (EtOAc in cyclohexane, 0-50%) to obtain the desired compound.

¹H NMR (400 MHz, $CDCl_3$) δ 11.89 (1H, s, NH), 4.44-4.37 (2H, m, $CO_2CH_2CH_3$), 1.44-1.35 (3H, m, $CO_2CH_2CH_3$); HRMS (TOF, ESI⁺) m/z: [M+H]⁺ Calcd for $CH_6O_2N_2NaBr_2$ 320.8673; Found 320.8673.

ii) Synthesis of 2,4-bis(4-fluorophenyl)-1H-imidazole-5-carboxylic acid

To a solution of ethyl 2,4-bis(4-fluorophenyl)-1H-imidazole-5-carboxylate in THF (3.4 mL) and EtOH (1.7 mL) was added 2.5 M NaOH and the reaction mixture was heated under reflux overnight. The resultant mixture was quenched with 2 M HCl and concentrated in vacuo. The residue was suspended in $CH_2Cl_2$ and the resultant precipitate was collected under suction filtration. The precipitate was washed with $CH_2Cl_2$ followed by water to obtain the desired compound.

General Procedure H

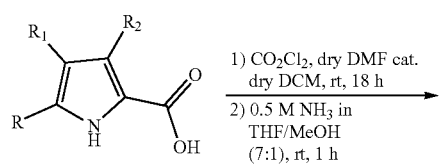

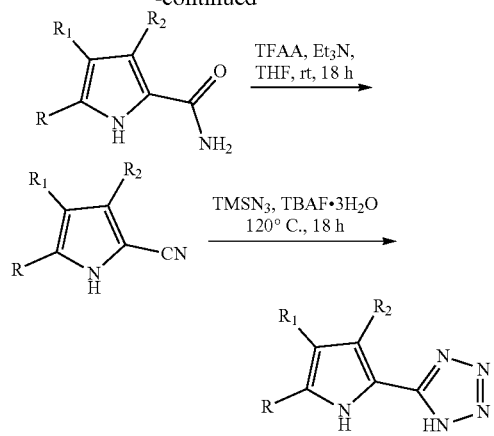

Example 30—3-(3,5-dichlorophenyl)-4-methyl-5-phenyl-1H-pyrrole-2-carboxamide

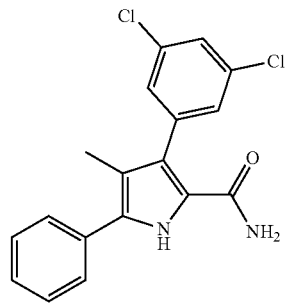 [SMILES: Cc1c(-c2ccccc2)[nH]c(C(N)=O)c1-c1cc(Cl)cc(Cl)c1]

i) Preparation of 3-(3,5-dichlorophenyl)-4-methyl-5-phenyl-1H-pyrrole-2-carboxamide To a suspension of 3-(3,5-dichlorophenyl)-4-methyl-5-phenyl-1H-pyrrole-2-carboxylic acid (0.10 g, 0.29 mmol) in dry DCM (4.5 mL) were added oxalyl chloride (0.4 mL, 4.51 mmol) and dry DMF (3.5 μL). The resultant mixture was stirred at room temperature for 18 h. The solvent was evaporated and the crude acid chloride immediately was used in the next step. To a suspension of the crude acid chloride were added 0.5M $NH_3$ in THF (7.0 mL) and MeOH (1 mL). The resulting solution was stirred for 1 h. The precipitate was filtered and then washed with cyclohexane to obtain the desired compound. LC-MS (M+H)=345.0

Example 31—3-(3,5-dichlorophenyl)-4-methyl-5-phenyl-1H-pyrrole-2-carbonitrile

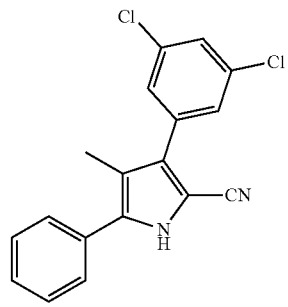

ii) Preparation of 3-(3,5-dichlorophenyl)-4-methyl-5-phenyl-1H-pyrrole-2-carbonitrile To a cooled (0° C.) suspension of 3-(3,5-dichlorophenyl)-4-methyl-5-phenyl-1H-pyrrole-2-carboxamide (0.1 g, 0.30 mmol) in THF (2.5 mL) was added Et₃N (0.2 mL, 1.7 mmol) and dropwise trifluoroacetic anhydride (0.2 mL, 1.7 mmol). The resultant mixture was stirred at room temperature for 18 h. The crude mixture was partitioned between EtOAc and sat. aq. NaHCO₃. The aqueous phase was further extracted with EtOAc and the combined organic extracts washed with brine, dried over Na₂SO₄, filtered and concentrated in vacuo. The residue was purified by flash chromatography (Cyclohexane in EtOAc, 0-25%) to obtain the desired compound. LC-MS (M+H)=327.0

Example 32—5-(3-(3,5-dichlorophenyl)-4-methyl-5-phenyl-1H-pyrrol-2-yl)-1H-tetrazole

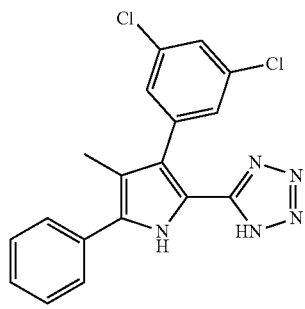

iii) Preparation of 5-(3-(3,5-dichlorophenyl)-4-methyl-5-phenyl-1H-pyrrol-2-yl)-1H-tetrazole In a vial equipped with a magnetic stirrer, TBAF.3H₂O (0.02 g, 0.06 mmol), 3-(3,5-dichlorophenyl)-4-methyl-5-phenyl-1H-pyrrole-2-carbonitrile (0.04 g, 0.12 mmol) and TMSN₃, (25 µL, 0.18 mmol) were added. The vial was sealed and heated under vigorous stirring at 120° C. for 18 h. The crude mixture was diluted with EtOAc and TBAF was removed by washing the organic phase with 1M HCl. The organic layer was dried over Na₂SO₄, filtered and dried under vacuum to obtain the desired compound. LC-MS (M+H)=370.0.

Biological Activity

The biological activity of the compounds of the present invention was tested using standard assay protocols.[7] The following representative enzymes NDM-1 (New Delhi metallo-β-lactamase-1), IMP-1 (Imipenemase-1), VIM-1 ((Veronese metallo-β-lactamase-1) and VIM-2 (Veronese metallo-β-lactamase-2) were selected from different clinically relevant B1 metallo-β-lactamases.

TABLE 1

| | pIC₅₀ values of Indoles and derivatives against VIM-2, IMP-1, NDM-1 and VIM-1 | | | | |
|---|---|---|---|---|---|
| | | | pIC₅₀ | | |
| Example | Compound Structure | VIM-2 | IMP-1 | NDM-1 | VIM-1 |
| 1 |  | <3 | IP | 4.8 | 3.7 |
| 2 |  | 5.1 | 5.2 | 6.1 | 4.3 |

TABLE 1-continued pIC$_{50}$ values of Indoles and derivatives against VIM-2, IMP-1, NDM-1 and VIM-1

| Example | Compound Structure | pIC$_{50}$ | | | |
| --- | --- | --- | --- | --- | --- |
| | | VIM-2 | IMP-1 | NDM-1 | VIM-1 |
| 3 | | 5.5 | 6.5 | 6.1 | 4.5 |
| 4 | | <3 | IP | <3 | <3 |
| 5 | | <3 | IP | <3 | <3 |
| 6 | | 8.9 | 7.4 | 7.9 | 7.7 |
| 7 | | <5.3 | <5.3 | <5.3 | <5.3 |

TABLE 1-continued pIC$_{50}$ values of Indoles and derivatives against VIM-2, IMP-1, NDM-1 and VIM-1

| Example | Compound Structure | pIC$_{50}$ | | | |
| --- | --- | --- | --- | --- | --- |
| | | VIM-2 | IMP-1 | NDM-1 | VIM-1 |
| 8 | | 7.9 | 6.6 | 6.0 | 5.3 |
| 9 | | 6.3 | 7.5 | 6.9 | 7.2 |
| 10 | | 8.1 | 7.5 | 7.1 | 6.6 |
| 11 | | 8.3 | 7.2 | 8.2 | 7.6 |
| 12 | | 7.2 | 5.8 | 7.1 | 6.8 |

TABLE 1-continued pIC$_{50}$ values of Indoles and derivatives against VIM-2, IMP-1, NDM-1 and VIM-1

| Example | Compound Structure | pIC$_{50}$ | | | |
|---|---|---|---|---|---|
| | | VIM-2 | IMP-1 | NDM-1 | VIM-1 |
| 13 | | 7.7 | 6.0 | 7.3 | 6.2 |
| 14 | | 8.1 | 7.2 | 7.9 | 7.2 |
| 15 | | 5.4 | 5.7 | 4.9 | 3.6 |
| 16 | | IP | 4.4 | 4.5 | <3.6 |
| 17 | | 5.8 | 6.7 | 7.4 | 6.7 |

TABLE 1-continued pIC$_{50}$ values of Indoles and derivatives against VIM-2, IMP-1, NDM-1 and VIM-1

| Example | Compound Structure | pIC$_{50}$ | | | |
|---|---|---|---|---|---|
| | | VIM-2 | IMP-1 | NDM-1 | VIM-1 |
| 18 | | 5.5 | 6.7 | 6.7 | 5.7 |
| 20 | | 6.4 | 5.3 | 6.2 | 5.1 |
| 21 | | 5.0 | <3.7 | 5.6 | <3.7 |
| 25 | | NI | IP | 4.4 | 3.4 |
| 26 | | NI | IP | 4.2 | 3.2 |

TABLE 1-continued pIC$_{50}$ values of Indoles and derivatives against VIM-2, IMP-1, NDM-1 and VIM-1

| Example | Compound Structure | pIC$_{50}$ VIM-2 | IMP-1 | NDM-1 | VIM-1 |
|---|---|---|---|---|---|
| 27 | (3,5-dimethylphenyl pyrrole-2-carboxylic acid) | NI | IP | 4.4 | 3.5 |
| 28 | (2,4-dibromo imidazole-5-carboxylic acid) | <4.4 | 4.8 | <4.4 | <4.4 |
| 29 | (2,4-bis(4-fluorophenyl) imidazole-5-carboxylic acid) | 4.8 | 4.8 | 5.2 | <3.7 |

IP—in progress
NI—no inhibition

In-Vitro Cell Based Work

Meropenem MICs were determined using the CLSI broth or agar microdilution protocol (Ref: Clinical and Laboratory Standards Institute. 2012. Methods for dilution antimicrobial susceptibility tests for bacteria that grow aerobically; 9th ed. Approved standard M07-A9. CLSI, Wayne, Pa.) in the absence of each inhibitor or in its presence at the concentration stated. In each case DMSO was used to dissolve inhibitors. The MIC is defined as the concentration of meropenem required to totally inhibit growth, as evidenced by an absence of optical density at 600 nm measured spectrophotometrically or by eye (Spectra Max 190; Molecular Devices, Wokingham, United Kingdom)

TABLE 2

Minimum inhibitory concentrations (MICs) of: i) meropenem; and ii) meropenem plus 4 mg/L of inhibitor compound Example 6 of the present invention for various strains of bacterial species.

| Isolate ID | Species | Gene | Meropenem | Meropenem + Example 6 (at 4 mg/ml) |
|---|---|---|---|---|
| 91N | E. coli | NDM | 4 | 1 |
| 133N | E. coli | NDM | 4 | 1 |
| IR30 | E. coli | NDM | 8 | 2 |
| IR10 | E. coli | NDM | 32 | 4 |
| 1-57 | K. pneumoniae | VIM | 8 | 2 |
| 85558-E-Pi | C. freundii | NDM | 8 | 1 |

TABLE 2-continued

Minimum inhibitory concentrations (MICs) of: i) meropenem; and ii) meropenem plus 4 mg/L of inhibitor compound Example 6 of the present invention for various strains of bacterial species.

| Isolate ID | Species | Gene | Meropenem | Meropenem + Example 6 (at 4 mg/ml) |
|---|---|---|---|---|
| 92N | E. coli | NDM | 16 | 2 |
| IR60 | E. coli | NDM | 16 | 2 |
| S1770 | A. baumannii | VIM | 8 | 1 |
| S13745 | E. coli | NDM | 2 | 0.5 |
| S1771 | K. pneumoniae | VIM | 8 | 1 |
| S1780 | K. pneumoniae | VIM | 8 | 2 |
| S12282 | K. pneumoniae | VIM | 64 | 16 |
| 85569-E-Pi | C. freundii | NDM | 8 | 2 |

TABLE 3

Minimum inhibitory concentrations (MICs) of: i) meropenem; and ii) meropenem plus 4 mg/L of inhibitor compound Example 6 of the present invention for various strains of bacterial species.

| Isolate ID | Species | Gene | Meropenem | Meropenem + Example 6 (at 8 mg/ml) |
|---|---|---|---|---|
| 14-B | A. caviae | | 0.125 | ≤0.06 |
| 09B61 | K. pneumoniae | VIM | 1 | 0.5 |

TABLE 3-continued

Minimum inhibitory concentrations (MICs) of: i) meropenem; and ii) meropenem plus 4 mg/L of inhibitor compound Example 6 of the present invention for various strains of bacterial species.

| Isolate ID | Species | Gene | Meropenem | Meropenem + Example 6 (at 8 mg/ml) |
|---|---|---|---|---|
| 85524-E-Pi | C. freundii | | 8 | 2 |
| WCH20 | E. coli | IMP-4 | 2 | 0.5 |
| N21 | A. baumannii | NDM | 64 | 32 |
| I20 | K. pneumoniae | NDM | 16 | 4 |
| 21F | K. pneumoniae | NDM | >64 | 16 |
| SA35 | E. cloaceae | NDM | 64 | 4 |
| 68F | E. coli | NDM | 4 | 1 |
| 66F | E. coli | NDM | 4 | 1 |
| IR14 | E. coli | NDM | 32 | 8 |
| IR26 | E. coli | NDM | 32 | 8 |
| IR22 | E. coli | NDM | 32 | 8 |
| 43N | E. coli | NDM | 32 | 2 |
| 39N | K. pneumoniae | NDM | 8 | 2 |
| 55N | E. coli | NDM | 16 | 1 |
| 10F75 | E. coli | VIM | 16 | 2 |
| S203-1 | K. pneumoniae | NDM | 4 | 1 |

While specific embodiments of the invention have been described for the purpose of reference and illustration, various modifications will be apparent to a person skilled in the art without departing from the scope of the invention as defined by the appended claims.

REFERENCES

1. J. Antibiot., 2013, 66, 571-591.
2. Clin. Microbiol. Rev., 2005, 18, 306-325.
3. Antimicrob. Agents Chemother., 2010, 54, 969-976.
4. Expert Opin. Ther. Pat., 2013, 23, 1469-1481.
5. a) http://www.who.int/en/; b) http://www.gov.uk.uk/; c) http://www.cdc.gov.
6. J. Hospit. Infect., 2015, 89, 241-247.
7. J Med Chem 56:6945-6953
8. Antimicrob. Agents Chemother., 2011, 55, 3635-3636 (http://aac.asm.org/content/57/7/3635.full.pdf)

The invention claimed is:

1. A compound of Formula I, or a pharmaceutically acceptable salt or solvate thereof, as shown below:

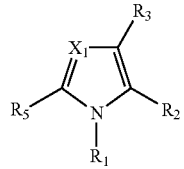

I wherein
R$_1$ is selected from hydrogen or; (1-4C)alkyl, wherein each (1-4C)alkyl is optionally substituted by one or more substituent groups selected from oxo, halo, cyano, nitro, hydroxy, carboxy, NR$^{1A}$R$^{1B}$ or (1-4C)alkoxy, wherein R$^{1A}$ and R$^{1B}$ are each independently selected from hydrogen or (1-2C)alkyl;
R$_2$ is selected from:
i) —C(O)OH;
ii) —C(O)OR$_{2A}$, wherein R$_{2A}$ is selected from (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^4$;
iii) —C(O)NR$_{2B}$R$_{2C}$; wherein R$_{2B}$ and R$_{2C}$ are each independently selected from hydrogen, (1-6C)alkyl, (3-8C)cycloalkyl, (3-8C)cycloalkyl(1-2C)alkyl, aryl, aryl-(1-2C)alkyl, heteroaryl, heteroaryl-(1-2C)alkyl, heterocyclyl or heterocyclyl-(1-2C)alkyl, each of which is optionally substituted by one or more substituent groups R$^4$;
iv) —C(O)NR$_{2D}$NR$_{2B}$R$_{2E}$; wherein R$_{2D}$ is selected from hydrogen or (1-6C)alkyl and R$_{2B}$ and R$_{2C}$ are as defined above;
v) tetrazolyl;
vi) triazolyl;
vii) —B(OR$_{2F}$)(OR$_{2G}$), wherein R$_{2F}$ and R$_{2G}$ are each independently selected from hydrogen, (1-6C)alkyl or R$_{2F}$ and R$_{2G}$ are linked such that, together with the B and O atoms, they form a 5 or 6-membered heterocyclic ring, which is optionally substituted by (1-2C)alkyl;
viii) trifluoromethylketone; or
ix) cyano;
x) —[C(O)]$_v$S(NR$_{2X}$)(O)NR$_{2B}$R$_{2C}$ (where v is 0 or 1), wherein R$_{2X}$ is selected from hydrogen, (1-6C)alkyl, C(O)R$_X$, C(O)OR$_X$, aryl, aryl-(1-2C)alkyl, heteroaryl, heteroaryl-(1-2C)alkyl, heterocyclyl or heterocyclyl-(1-2C)alkyl, wherein R$_X$ is selected from (1-6C)alkyl, aryl or heteroaryl, each of which is optionally substituted with one or more R$_4$, and wherein R$_{2B}$ and R$_{2C}$ are as defined above;
xi) —[C(O)]$_w$N(R$_{2B}$)S(NR$_{2X}$)(O)R$_X$ (where w is 0 or 1), wherein R$_{2B}$, R$_{2X}$ and R$_X$ are each as defined above; or
xii) —S(O)$_y$NR$_{2B}$R$_{2C}$ (wherein y is 1 or 2), and wherein R$_{2B}$ and R$_{2C}$ are as defined above,
and wherein R$^4$ is selected from oxo, halo, cyano, nitro or a group of the formula:

—Y$^2$—X$^2$—Z$^2$ wherein
Y$^2$ is absent or a linker group of the formula —[CR$^{41}$R$^{42}$]$_m$— in which m is an integer selected from 1, 2, 3 or 4, and R$^{41}$ and R$^{42}$ are each independently selected from hydrogen or (1-2C) alkyl;
X$^2$ is absent or —O—, —C(O)—, —C(O)O—, —OC(O)—, —CH(OR$^{43}$)—, —N(R$^{43}$)—, —N(R$^{43}$)—C(O)—, —N(R$^{43}$)—C(O)O—, —C(O)—N(R$^{43}$)—, —N(R$^{43}$)C(O)N(R$^{43}$)—, —S—, —SO—, —SO$_2$—, —S(O)$_2$N(R$^{43}$)—, or —N(R$^{43}$)SO$_2$— wherein R$^{43}$ is selected from hydrogen or methyl; and
Z$^2$ is hydrogen, (1-6C)alkyl, (2-6C)alkenyl, (2-6C) alkynyl, aryl, (3-6C)cycloalkyl, (3-6C)cycloalkenyl, heteroaryl or heterocyclyl;
and wherein Z$^2$ is optionally further substituted by one or more substituent groups independently selected from oxo, halo, cyano, nitro, hydroxy, carboxy, NR$^{44}$R$^{45}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{44}$R$^{45}$, NR$^{44}$C(O)R$^{45}$, NR$^{44}$S(O)$_2$R$^{45}$ and S(O)$_2$NR$^{44}$R$^{45}$; wherein R$^{44}$ and R$^{45}$ are each independently selected from hydrogen, (1-4C)alkyl or (3-6C)cycloalkyl or (3-6C)cycloalkyl(1-2C)alkyl; or $R^{A4}$ and $R^{A5}$ can be linked such that, together with the nitrogen atom to which they are attached, they form a 4-6 membered heterocyclic ring;

and wherein any alkyl, aryl, heterocyclyl or heteroaryl group present in a substituent group on $Z^2$ is optionally further substituted by halo, cyano, nitro, hydroxy, caboxy, $NR^{A6}R^{A7}$, (1-2C)alkoxy, or (1-2C)alkyl; wherein $R^{A6}$ and $R^{A7}$ are selected from hydrogen or (1-2C)alkyl;

$R_3$ is selected from halo, cyano, hydroxyl, aryl, (1-6C)alkyl, (2-6C)alkenyl, (2-6C)alkynyl, (3-8C)cycloalkyl, (3-8C)cycloalkenyl, heteroaryl or heterocyclyl, wherein said aryl, (3-8C)cycloalkyl, (3-8C)cycloalkenyl, heteroaryl or heterocyclyl is optionally substituted by one or more $R^B$;

$R^B$ is halo, cyano, nitro, hydroxy or a group:

—$Y^3$—$X^3$—$Z^3$ wherein
- $Y^3$ is absent or a linker group of the formula —$[CR^{B1}R^{B2}]_n$— in which n is an integer selected from 1, 2, 3 or 4, and $R^{B1}$ and $R^{B2}$ are each independently selected from hydrogen or (1-2C)alkyl;
- $X^3$ is absent or —O—, —C(O)—, —C(O)O—, —OC(O)—, —CH(OR$^{B3}$)—, —N(R$^{B3}$)—, —N(R$^{B4}$)—C(O)—, —N(R$^{B4}$)—C(O)O—, —C(O)—N(R$^{B3}$)—, —N(R$^{B4}$)C(O)N(R$^{B3}$)—, —S—, —SO—, —SO$_2$—, or —N(R$^{B4}$)SO$_2$— wherein $R^{B3}$ and $R^{B4}$ are each independently selected from hydrogen or methyl; and
- $Z^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
- and wherein $Z^3$ is optionally further substituted by one or more substituent groups independently selected from oxo, halo, cyano, nitro, hydroxy, carboxy, NR$^{B5}$R$^{B6}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$; wherein R$^{B5}$ and R$^{B6}$ are each independently selected from hydrogen, (1-4C)alkyl or (3-6C)cycloalkyl or (3-6C)cycloalkyl(1-2C)alkyl; or R$^{B5}$ and R$^{B6}$ can be linked such that, together with the nitrogen atom to which they are attached, they form a 4-7 membered heterocyclic ring;
- and wherein any alkyl, aryl, heterocyclyl or heteroaryl group present in a substituent group on $Z^3$ is optionally further substituted by halo, cyano, nitro, hydroxy, caboxy, NR$^{B7}$R$^{B8}$, (1-2C)alkoxy, or (1-2C)alkyl; wherein R$^{B7}$ and R$^{B8}$ are selected from hydrogen or (1-2C)alkyl;
- or R$^{B3}$ and $Z^3$ can be linked such that, together with the nitrogen atom to which they are attached, they form a 4-7 membered heterocyclic ring, which is optionally substituted by oxo, halo, cyano, nitro, hydroxy, carboxy, NR$^{B5}$R$^{B6}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, C(O)NR$^{B5}$R$^{B6}$, NR$^{B5}$C(O)R$^{B6}$, NR$^{B5}$S(O)$_2$R$^{B6}$ and S(O)$_2$NR$^{B5}$R$^{B6}$;

$X_1$ is selected from N or C—R$_4$;

$R_4$ is selected from halo, cyano, nitro, hydroxy or a group

—$Y^4$—$X^4$—$Z^4$ wherein:
- $Y^4$ is absent or a linker group of the formula —$[CR^{A4}R^{A B}]_q$— in which q is an integer selected from 1 or 2 and $R^{A4}$ and $R^{A B}$ are each independently selected from hydrogen or methyl;
- $X^4$ is absent or —O—, —C(O)—, —C(O)O—, —OC(O)—, —CH(OR$^{4C}$)—, —N(R$^{4C}$)—, —N(R$^{4D}$)—C(O)—, —N(R$^{4D}$)—C(O)O—, —C(O)—N(R$^{4C}$)—, —S—, —SO—, —SO$_2$—, —S(O)$_2$N(R$^{4C}$)—, or —N(R$^{4D}$)SO$_2$— wherein R$^{4C}$ and R$^{4D}$ are each independently selected from hydrogen or (1-4C)alkyl; and
- $Z^4$ is hydrogen or (1-4C)alkyl which is optionally further substituted by one or more substituent groups independently selected from oxo, halo, cyano, nitro, hydroxy, carboxy, NR$^{4E}$R$^{4F}$ or (1-2C)alkoxy; wherein R$^{4E}$ and R$^{4F}$ are each independently selected from hydrogen or (1-2C)alkyl;

$R_5$ is selected from hydrogen, halo, cyano, nitro, hydroxy or a group of the formula:

—$Y^5$—$X^5$-$Q^5$-$Z^5$ wherein $Y^5$ is absent or a linker group of the formula —$[CR^{5A}R^{5B}]_p$— in which p is an integer selected from 1 or 2, and R$^{5A}$ and R$^{5B}$ are each independently selected from hydrogen or (1-2C)alkyl;
- $X^5$ is absent or —O—, —C(O)—, —C(O)O—, —OC(O)—, —CH(OR$^{5C}$)—, —N(R$^{5C}$)—, N(R$^{5D}$)—C(O)—, —N(R$^{5D}$)—C(O)O—, —C(O)—N(R$^{5C}$)—, —N(R$^{5D}$)C(O)N(R$^{5C}$)—, —S—, —SO—, —SO$_2$—, —S(O)$_2$N(R$^{5C}$)—, or —N(R$^{5D}$)SO$_2$— wherein R$^{5C}$ and R$^{5D}$ are each independently selected from hydrogen or (1-6C)alkyl;
- $Q^5$ is absent or a (1-4C)alkylene optionally interrupted with one or more 0 or S atoms; and
- $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
- and wherein $Z^5$ is optionally further substituted by one or more substituent groups independently selected from oxo, halo, cyano, nitro, hydroxy, carboxy, NR$^{5E}$R$^{5F}$ (1-4C)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkyl sulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, Si[(1-4C)alkyl]$_3$, C(O)R$^{5E}$, C(O)OR$^{5E}$, OC(O)R$^{5E}$, C(O)NR$^{5E}$R$^{5F}$, NR$^{5E}$C(O)R$^{5F}$, NR$^{5E}$S(O)$_2$R$^{5F}$ and S(O)$_2$NR$^{5E}$R$^{5F}$; wherein R$^{5E}$ and R$^{5F}$ are each independently selected from hydrogen, (1-4C)alkyl, (1-4C)haloalkyl, (3-6C)cycloalkyl or (3-6C)cycloalkyl(1-2C)alkyl; or R$^{5E}$ and R$^{5F}$ can be linked such that, together with the nitrogen atom to which they are attached, they form a 4-7 membered heterocyclic ring;
- and wherein any alkyl, aryl, heterocyclyl or heteroaryl group present in a substituent group on $Z^5$ is optionally further substituted by one or more substituent groups selected from halo, (1-2C)haloalkyl, cyano, nitro, hydroxy, carboxy, $NR^{5G}R^{5H}$, (1-2C)alkoxy, or (1-2C)alkyl; wherein $R^{5G}$ and $R^{5H}$ are selected from hydrogen or (1-2C)alkyl;

or $R^{5C}$ and $Z^5$ can be linked such that, together with the nitrogen atom to which they are attached, they form a 4-7 membered heterocyclic ring, which is optionally substituted by oxo, halo, cyano, nitro, hydroxy, carboxy, $NR^{5E}R^{5F}$, (1-4C)alkoxy, (1-4C)alkyl, (1-4C)haloalkyl, (3-8C)cycloalkyl, (3-8C)cycloalkyl-(1-3C)alkyl, (1-4C)alkanoyl, (1-4C)alkylsulphonyl, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$.

2. A compound of Formula I according to claim 1, or a pharmaceutically acceptable salt or solvate thereof, for use in the treatment of a bacterial infection in combination with a beta-lactam antibiotic.

3. A compound according to claim 1, wherein $R_1$ is selected from hydrogen or (1-4C)alkyl which is optionally substituted by one or more substituent groups selected from oxo, halo, or (1-2C)alkoxy.

4. A compound according to claim 1, wherein $R_1$ is hydrogen.

5. A compound according to claim 1, wherein $R_2$ is selected from:
(i) —C(O)OH;
(ii) —C(O)$NR_{2B}R_{2C}$; wherein $R_{2B}$ and $R_{2C}$ are each independently selected from hydrogen, (1-6C)alkyl, (3-8C)cycloalkyl, aryl or heteroaryl, each of which is optionally substituted by one or more substituent groups $R^A$;
(iii) —C(O)$NR_{2D}NR_{2B}R_{2C}$; wherein $R_{2D}$ is selected from hydrogen or (1-2C)alkyl and $R_{2B}$ and $R_{2C}$ are as defined above;
(iv) tetrazolyl;
(v) —B($OR_{2F}$)($OR_{2G}$), wherein $R_{2F}$ and $R_{2G}$ are each independently selected from hydrogen, (1-4C)alkyl or $R_{2F}$ and $R_{2G}$ are linked such that, together with the B and O atoms, they form a 5 or 6-membered heterocyclic ring, which is optionally substituted by (1-2C)alkyl; or
(vi) cyano:
and wherein $R^A$ is selected from halo, cyano, or a group of the formula:

wherein
$X^2$ is absent or —C(O)—, —$SO_2$—; and
$Z^2$ is hydrogen, (1-6C)alkyl, aryl, or heteroaryl;
and wherein $Z^2$ is optionally further substituted by one or more substituent groups independently selected from halo, hydroxy, $NR^{A4}R^{A5}$, (1-4C)alkoxy or (1-4C)alkyl, wherein $R^{A4}$ and $R^{A5}$ are each independently selected from hydrogen, or (1-2C)alkyl.

6. A compound according to claim 1, wherein $R_2$ is —C(O)OH, —C(O)$NH_2$, tetrazolyl or cyano.

7. A compound according to claim 1, wherein $R_3$ is selected from halo, cyano, hydroxy, aryl, (1-6C)alkyl, (2-6C)alkenyl, heteroaryl or heterocyclyl, wherein said aryl, heteroaryl or heterocyclyl is optionally substituted by one or more $R^B$;

$R^B$ is halo, cyano, nitro, hydroxy or a group:

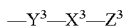

wherein
$Y^3$ is absent or a linker group of the formula —$[CR^{B1}R^{B2}]_n$— in which n is an integer selected from 1, 2, 3 or 4, and $R^{B1}$ and $R^{B2}$ are each independently selected from hydrogen or (1-2C)alkyl;
$X^3$ is absent or —O—, —C(O)—, —C(O)O—, —OC(O)—, —CH($OR^{B3}$)—, —N($R^{B3}$)—, N($R^{B4}$)—C(O)—, —N($R^{B4}$)—C(O)O—, —C(O)—N($R^{B3}$)—, —N($R^{B4}$)C(O)N($R^{B3}$)—, —S—, —SO—, —$SO_2$—, or —N($R^{B4}$)$SO_2$— wherein $R^{B3}$ and $R^{B4}$ are each independently selected from hydrogen or methyl; and
$Z^3$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
and wherein $Z^3$ is optionally further substituted by one or more substituent groups independently selected from oxo, halo, cyano, nitro, hydroxy, carboxy, $NR^{B5}R^{B6}$, (1-4C)alkoxy, (1-4C)alkyl, (1-4C)alkanoyl, (1-4C)alkylsulphonyl, $C(O)NR^{B5}R^{B6}$, $NR^{B5}C(O)R^{B6}$, $NR^{B5}S(O)_2R^{B6}$ and $S(O)_2NR^{B5}R^{B6}$; wherein $R^{B5}$ and $R^{B6}$ are each independently selected from hydrogen, (1-4C)alkyl or (3-6C)cycloalkyl or (3-6C)cycloalkyl(1-2C)alkyl.

8. A compound according to claim 1, wherein $R_3$ is selected from halo, aryl or 5- or 6-membered heteroaryl, wherein said aryl or heteroaryl is optionally substituted by one or more $R^B$;

$R^B$ is halo, cyano, nitro, hydroxy or a group:

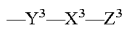

wherein
$Y^3$ is absent or a linker group of the formula —$[CR^{B1}R^{B2}]_n$— in which n is an integer selected from 1 or 2, and $R^{B1}$ and $R^{B2}$ are each independently selected from hydrogen or methyl;
$X^3$ is absent or —O—, —C(O)—, —C(O)O—, —N($R^{B3}$)—, —C(O)—N($R^{B3}$)—, —S—, —SO—, or —$SO_2$—, wherein $R^{B3}$ and $R^{B4}$ are each independently selected from hydrogen or methyl; and
$Z^3$ is hydrogen, (1-6C)alkyl, aryl or 5- or 6-membered heteroaryl;
and wherein $Z^3$ is optionally further substituted by one or more substituent groups independently selected from oxo, halo, cyano, nitro, hydroxy, carboxy, amino, (1-2C)alkoxy or (1-2C)alkyl.

9. A compound according to claim 1, wherein $X_1$ is C—$R_4$.

10. A compound according to claim 1, wherein $R_4$ is selected from halo, cyano, nitro, hydroxy or a group

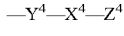

wherein:
$Y^4$ is absent or a linker group of the formula —$[CR^{4A}R^{4B}]_q$— in which q is an integer selected from 1 or 2 and $R^{4A}$ and $R^{4B}$ are each independently selected from hydrogen or methyl;
$X^4$ is absent or —O—, —C(O)—, —C(O)O—, —OC(O)—, —N($R^{4C}$)—, —N($R^{4D}$)—C(O)—, —C(O)—N($R^{4C}$)—, —S—, —SO— or —$SO_2$—, wherein $R^{4C}$ and $R^{4D}$ are each independently selected from hydrogen or (1-4C)alkyl; and
$Z^4$ is hydrogen or (1-4C)alkyl which is optionally further substituted by one or more substituent groups independently selected from oxo, halo, cyano, nitro, hydroxy, carboxy, amino or (1-2C)alkoxy.

11. A compound according to claim 1, wherein $R_4$ is selected from halo or (1-4C)alkyl.

12. A compound according to claim 1, wherein $R_5$ is selected from hydrogen, halo, cyano, nitro, hydroxy or a group of the formula:

$$-Y^5-X^5-Q^5-Z^5$$

wherein
  $Y^5$ is absent or a linker group of the formula $-[CR^{5A}R^{5B}]_p-$ in which p is an integer selected from 1 or 2, and $R^{5A}$ and $R^{5B}$ are each independently selected from hydrogen or (1-2C)alkyl;
  $X^5$ is absent or $-O-$, $-C(O)-$, $-C(O)O-$, $-OC(O)-$, $-N(R^{5C})-$, $-N(R^{5D})-C(O)-$, $-C(O)-N(R^{5C})-$, $-S-$, $-SO-$, $-SO_2-$, $-S(O)_2N(R^{5C})-$, or $-N(R^{5D})SO_2-$ wherein $R^{5C}$ and $R^{5D}$ are each independently selected from hydrogen or (1-6C)alkyl;
  $Q^5$ is absent or a (1-3C)alkylene optionally interrupted with one or more O atoms; and
  $Z^5$ is hydrogen, (1-6C)alkyl, (2-6C)alkenyl, (2-6C)alkynyl, aryl, (3-6C)cycloalkyl, (3-6C)cycloalkenyl, heteroaryl or heterocyclyl;
    and wherein $Z^5$ is optionally further substituted by one or more substituent groups independently selected from oxo, halo, cyano, nitro, hydroxy, carboxy, $NR^{5E}R^{5F}$, (1-4C)alkoxy, (1-4C)alkyl, (1-4C)haloalkyl, (1-4C)haloalkoxy, (3-8C)cycloalkyl, (3-8C)cycloalkyl-(1-3C)alkyl, (1-4C)alkanoyl, (1-4C)alkyl sulphonyl, aryl, aryloxy, aryl-(1-2C)alkyl, heterocyclyl, heterocyclyloxy, heterocyclyl-(1-2C)alkyl, heteroaryl, heteroaryloxy, heteroaryl-(1-2C)alkyl, $Si[(1-4C)alkyl]_3$, $C(O)R^{5E}$, $C(O)OR^{5E}$, $OC(O)R^{5E}$, $C(O)NR^{5E}R^{5F}$, $NR^{5E}C(O)R^{5F}$, $NR^{5E}S(O)_2R^{5F}$ and $S(O)_2NR^{5E}R^{5F}$; wherein $R^{5E}$ and $R^{5F}$ are each independently selected from hydrogen, (1-4C)alkyl, (1-4C)haloalkyl or (3-6C)cycloalkyl; or $R^{5E}$ and $R^{5F}$ can be linked such that, together with the nitrogen atom to which they are attached, they form a 4-7 membered heterocyclic ring;
    and wherein any alkyl, aryl, heterocyclyl or heteroaryl group present in a substituent group on $Z^5$ is optionally further substituted by halo, cyano, nitro, hydroxy, caboxy, $NR^{5G}R^{5H}$, (1-2C)alkoxy, or (1-2C)alkyl; wherein $R^{5G}$ and $R^{5H}$ are selected from hydrogen or (1-2C)alkyl;
  or $R^{5C}$ and $Z^5$ can be linked such that, together with the nitrogen atom to which they are attached, they form a 4-7 membered heterocyclic ring, which is optionally substituted by one or more substituent groups selected from oxo, halo, (1-2C)haloalkyl, cyano, nitro, hydroxy, carboxy, $NR^{5E}R^{5F}$, (1-4C)alkoxy, (1-4C)alkyl, (1-4C)haloalkyl, (3-8C)cycloalkyl, (1-4C)alkanoyl, (1-4C)alkyl sulphonyl, $C(O)R^{5E}$, $C(O)OR^{5E}$, $C(O)NR^{5E}R^{5F}$ or $NR^{5E}C(O)R^{5F}$; or
  $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5i}R^{5J}$, (1-4C)alkoxy, (1-4C)alkyl, (1-4C)haloalkyl, (3-8C)cycloalkyl, (1-4C)alkanoyl, (1-4C)alkylsulphonyl, $C(O)R^{5J}$, $C(O)OR^{5J}$, $OC(O)R^{5J}$, $C(O)NR^{5i}R^{5J}$, $NR^{5i}C(O)R^{5J}$, $NR^{5i}S(O)_2R^{5J}$ and $S(O)_2NR^{5i}R^{5J}$, wherein $R^{5i}$ and $R^{5j}$ are each independently selected from hydrogen, (1-4C)alkyl or (3-6C)cycloalkyl.

13. A compound according to claim 1, wherein $R_5$ is selected from hydrogen, halo, cyano, nitro, hydroxy or a group $$-X^5-Z^5$$

wherein
  $X^5$ is absent or $-N(R^{5C})-$, $-S(O)_2N(R^{5C})-$ or $-N(R^{5D})SO_2-$ wherein $R^{5C}$ is selected from hydrogen or (1-2C)alkyl; and
  $Z^5$ is hydrogen, (1-6C)alkyl, aryl, 5- or 6-membered heteroaryl or 5- or 6-membered heterocyclyl;
    and wherein $Z^5$ is optionally further substituted by one or more substituent groups independently selected from halo, cyano, nitro, hydroxy, carboxy, $NR^{5E}R^{5F}$, (1-4C)alkoxy, (1-4C)alkyl, (1-4C)haloalkyl, (1-4C)haloalkoxy, ((1-4C)alkylsulphonyl, aryl, 5- or 6-membered heterocyclyl, 5- or 6-membered heteroaryl, $C(O)R^{5E}$, $C(O)OR^{5E}$, $C(O)NR^{5E}R^{5F}$ or $NR^{5E}C(O)R^{5F}$; wherein $R^{5E}$ and $R^{5F}$ are each independently selected from hydrogen, (1-4C)alkyl or (1-4C)haloalkyl;
    and wherein any alkyl, aryl, heterocyclyl or heteroaryl group present in a substituent group on $Z^5$ is optionally further substituted by halo, cyano, nitro, hydroxy, amino, (1-2C)alkoxy or (1-2C)alkyl; or
  $R^4$ and $R^5$ may be linked such that, together with the carbon atoms to which they are attached, they form a fused 5, 6, 7 or 8-membered non-aromatic carbocyclic or heterocyclic ring, which is optionally substituted by one or more substituents selected from oxo, halo, cyano, nitro, hydroxy, carboxy, $NR^{5i}R^{5J}$, (1-4C)alkoxy, (1-4C)alkyl or (1-4C)haloalkyl, wherein $R^{5i}$ and $R^{5j}$ are each independently selected from hydrogen or (1-4C)alkyl.

14. A compound according to claim 1, wherein $R_5$ is selected from hydrogen, halo, cyano, nitro, hydroxy or a group $$-X^5-Z^5$$

wherein
  $X^5$ is absent or $-N(R^{5C})-$, $-S(O)_2N(R^{5C})-$ or $-N(R^{5D})SO_2-$ wherein $R^{5C}$ is selected from hydrogen or (1-2C)alkyl; and
  $Z^5$ is hydrogen, (1-6C)alkyl, aryl, 5- or 6-membered heteroaryl or 5- or 6-membered heterocyclyl;
    and wherein $Z^5$ is optionally further substituted by one or more substituent groups independently selected from halo, cyano, hydroxy, carboxy, amino, (1-2C)alkoxy, (1-2C)alkyl, (1-2C)haloalkyl, (1-2C)haloalkoxy, (1-2C)alkylsulphonyl, phenyl, $C(O)R^{5E}$, $C(O)OR^{5E}$, $C(O)NR^{5E}R^{5F}$ or $NR^{5E}C(O)R^{5F}$; wherein $R^{5E}$ and $R^{5F}$ are each independently selected from hydrogen, (1-2C)alkyl or (1-2C)haloalkyl;
    and wherein any alkyl or phenyl group present in a substituent group on $Z^5$ is optionally further substituted by halo, cyano, hydroxy, amino, (1-2C) alkoxy or (1-2C)alkyl.

15. A compound selected from any one of the following:
3-Phenyl-4,5,6,7-tetrahydro-1H-indole-2-carboxylic acid;
7-Methyl-3-phenyl-4,5,6,7-tetrahydro-1H-indole-2-carboxylic acid;
7,7-Dimethyl-3-phenyl-4,5,6,7-tetrahydro-1H-indole-2-carboxylic acid;

3,5,5-Trimethyl-4-oxo-4,5,6,7-tetrahydro-1H-indole-2-carboxylic acid;
3-(3,5-Dichlorophenyl)-5,5-dimethyl-4,5,6,7-tetrahydro-1H-4,6-methanoindole-2-carboxylic acid;
3-(3,5-Dichlorophenyl)-4-methyl-5-phenyl-1H-pyrrole-2-carboxylic acid;
5-(5-(3,5-Dichlorophenyl)furan-2-yl)-4-methyl-1H-pyrrole-2-carboxylic acid;
3-(3-Chloro-4-((methylsulfonyl)methyl)phenyl)-4-ethyl-5-(2-(trifluoromethyl)phenyl)-1H-pyrrole-2-carboxylic acid;
3-(3,5-Dichlorophenyl)-4-methyl-5-phenyl-1H-pyrrole-2-carboxamide;
3-(3,5-Dichlorophenyl)-4-methyl-5-phenyl-1H-pyrrole-2-carbonitrile;
5-(3-(3,5-Dichlorophenyl)-4-methyl-5-phenyl-1H-pyrrol-2-yl)-1H-tetrazole;
3-(3,5-Dichlorophenyl)-4-ethyl-5-phenyl-1H-pyrrole-2-carboxylic acid;
4-Ethyl-3-(4-fluorophenyl)-5-phenyl-1H-pyrrole-2-carboxylic acid;
3-(3-Chloro-4-((methylsulfonyl)methyl)phenyl)-4-ethyl-5-phenyl-1H-pyrrole-2-carboxylic acid;
4-Methyl-3-phenyl-5-(3-(2,2,2-trifluoroacetyl)phenyl)-1H-pyrrole-2-carboxylic acid;
3-(3,5-Dichlorophenyl)-4-methyl-5-(2-(2,2,2-trifluoroacetyl)phenyl)-1H-pyrrole-2-carboxylic acid;
3-(3,5-Dichlorophenyl)-4-methyl-5-(3-(2,2,2-trifluoroacetyl)phenyl)-1H-pyrrole-2-carboxylic acid;
3-(3,5-Dichlorophenyl)-4-methyl-5-(1,2,3,6-tetrahydropyridin-4-yl)-1H-pyrrole-2-carboxylic acid;
3-(3,5-Dichlorophenyl)-4-fluoro-5-phenyl-1H-pyrrole-2-carboxylic acid;
3-(3,5-Dichlorophenyl)-5-(thiophen-2-yl)-1H-pyrrole-2-carboxylic acid;
3-(4-Fluorophenyl)-5-(phenylsulfonamido)-1H-pyrrole-2-carboxylic acid;
5-(Diisopropylamino)-3-(4-fluorophenyl)-1H-pyrrole-2-carboxylic acid;
3-(4-Hydroxyphenyl)-4-methyl-5-phenyl-1H-pyrrole-2-carboxylic acid;
3-(4-Mercaptophenyl)-4-methyl-5-phenyl-1H-pyrrole-2-carboxylic acid;
3-(4-(Carboxymethyl)phenyl)-4-methyl-5-phenyl-1H-pyrrole-2-carboxylic acid;
3-(4-((N,N-Dimethylsulfamoyl)methyl)phenyl)-4-methyl-5-phenyl-1H-pyrrole-2-carboxylic acid;
5-Cyclopropyl-3-(3,5-dichlorophenyl)-4-methyl-1H-pyrrole-2-carboxylic acid;
4-Methyl-5-nitro-3-phenyl-1H-pyrrole-2-carboxylic acid;
5-Acetyl-4-methyl-3-phenyl-1H-pyrrole-2-carboxylic acid;
5-Acetyl-1,4-dimethyl-3-phenyl-1H-pyrrole-2-carboxylic acid;
4-Methyl-3-phenyl-5-(3-(2,2,2-trifluoro-1-hydroxyethyl)phenyl)-1H-pyrrole-2-carboxylic acid;
4-Methyl-3-phenyl-5-(2-(2,2,2-trifluoro-1-hydroxyethyl)phenyl)-1H-pyrrole-2-carboxylic acid;
3-Chloro-5-(2-phenoxyacetamido)-1H-pyrrole-2-carboxylic acid;
5-(2-Phenoxyacetamido)-3-phenyl-1H-pyrrole-2-carboxylic acid;
3-(4-Carboxyphenyl)-4-methyl-5-phenyl-1H-pyrrole-2-carboxylic acid; or
2,4-Bis(4-fluorophenyl)-1H-imidazole-5-carboxylic.

16. A pharmaceutical composition comprising a compound according to claim 1, or a pharmaceutically acceptable salt or solvate thereof, in admixture with a pharmaceutically acceptable diluent or carrier.

17. A pharmaceutical composition according to claim 16, for use in the treatment of a bacterial infection in combination with a beta-lactam antibiotic.

18. A method of treating a bacterial infection in a patient in need of such treatment, said method comprising administering to said patient a therapeutically effective amount of a compound according to claim 1, or a pharmaceutically acceptable salt or solvate thereof, or a pharmaceutical composition thereof in administration with a pharmaceutically acceptable diluent or carrier, in combination with a beta-lactam antibiotic.

19. A kit of parts comprising the following components:
(i) a compound of Formula I, according to claim 1, or a pharmaceutically-acceptable salt thereof, in association with a pharmaceutically acceptable adjuvant, diluent or carrier; and
(ii) a β-lactam antibiotic, or a pharmaceutically-acceptable salt thereof, in association with a pharmaceutically acceptable adjuvant, diluent or carrier,
wherein the components are provided in a form which is suitable for sequential, separate and/or simultaneous administration.

20. A kit according to claim 19, for use in the treatment of a bacterial infection.

* * * * *